(12) United States Patent
Heyduk

(10) Patent No.: US 7,172,865 B2
(45) Date of Patent: *Feb. 6, 2007

(54) RAPID AND SENSITIVE ASSAY FOR THE DETECTION AND QUANTIFICATION OF COREGULATORS OF NUCLEIC ACID BINDING FACTORS

(75) Inventor: Tomasz Heyduk, Ballwin, MO (US)

(73) Assignee: Saint Louis University, Saint Louis, MO (US)

( * ) Notice: Subject to any disclaimer, the term of this patent is extended or adjusted under 35 U.S.C. 154(b) by 20 days.

This patent is subject to a terminal disclaimer.

(21) Appl. No.: 10/062,064

(22) Filed: Jan. 31, 2002

(65) Prior Publication Data

US 2003/0124541 A1 Jul. 3, 2003

Related U.S. Application Data

(63) Continuation-in-part of application No. 09/928,385, filed on Aug. 13, 2001, now Pat. No. 6,544,746.

(51) Int. Cl.
C12Q 1/68 (2006.01)
C12N 15/11 (2006.01)
C07H 21/00 (2006.01)

(52) U.S. Cl. .......................................... 435/6; 536/23.1
(58) Field of Classification Search ...................... None
See application file for complete search history.

(56) References Cited

U.S. PATENT DOCUMENTS

| | | | |
|---|---|---|---|
| 5,763,181 A | 6/1998 | Han et al. | 435/6 |
| 6,171,779 B1 | 1/2001 | Chada et al. | 435/4 |
| 6,177,248 B1 * | 1/2001 | Oliner et al. | 435/6 |
| 6,210,896 B1 | 4/2001 | Chan | 435/6 |
| 6,214,552 B1 * | 4/2001 | Heroux et al. | 435/6 |
| 6,248,532 B1 | 6/2001 | Keegan | 435/6 |
| 6,265,213 B1 | 7/2001 | Morgan et al. | 435/320.1 |
| 6,297,059 B1 | 10/2001 | Song et al. | 436/501 |
| 6,312,896 B1 * | 11/2001 | Heroux et al. | 435/6 |
| 6,355,428 B1 | 3/2002 | Schroth et al. | 435/6 |
| 6,358,679 B1 | 3/2002 | Heid et al. | 435/5 |
| 6,544,746 B2 * | 4/2003 | Heyduk | 435/6 |

FOREIGN PATENT DOCUMENTS

WO WO00/40753 7/2000

OTHER PUBLICATIONS

Patent Cooperation Treaty, International Search Report dated Jul. 27, 2004.
Bailey et al., Biochemistry, vol. 34, *Interaction between the Escherichia coli Regulatory Protein TyrR and DNA: A Fluorescence Footprinting Study*, pp. 15802-15812, 1995.
Bjornson et al., Biochemistry, vol. 35, *Kinetic Mechanism of DNA Binding and DNA-Induced Dimerization of the Escherichia coli Rep Helicase*, pp. 2268-2282, 1996.
Campbell et al., Biochem. J., vol. 216, *A homogeneous immunoassay of cyclic nucleotides based on chemiluminescence energy transfer*, pp. 185-194, 1983.
Fried et al., Nucleic Acids Research, vol. 9, No. 23, *Equilibria and kinetics of lac repressor-operator interactions by polyacrylamide gel elctrophoresis*, pp. 6505-6525, 1981.
Galas et al., Nucleic Acids Research, vol. 5, No. 9, *DNAase footprinting: a simple method for the detection of protein-DNA binding specificity*pp. 3157-3170, Sep. 1978.
Gourves et al., Journal of Biol. Chem., vol. 275, No. 15, *Equilibrium Biding of Single-stranded DNA with Herpes Simplex Virus Type 1-coded single-stranded DNA binding Protein, ICP8*, pp. 10864-10869, Apr. 14, 2000.
Hey et al., Biochemistry, vol. 40, *Binding of XPA and ROA to Damaged DNA investigated by Fluorescence Anisotropy*, pp. 2901-2910, 2001.
Heyduk et al., Proc. Natl. Acad. Sci. USA, vol. 87, *Application of fluorescence energy transfer and polarization to monitor Escherichia coli camp receptor protein and lac promoter interaction*, pp. 1744-1748, Mar. 1980.
Hill et al., Methods in Enzymology, vol. 278, *Fluorescence Approaches to Study of Protein-Nucleic Acid Complexation*, pp. 390-416, 1997.
Lima et al., PNAS, vol. 97, No. 26, *DNA tightens the dimeric DNA-binding domain of human Papillomavirus E2 protein without changes in volume*, p. 14298-14294, Dec. 19, 2000.
Maiti et al., Proc. Natl. Acad. Sci. USA, vol. 94, *Fluorescence correlation spectroscopy: Diagnostics for sparse molecules*, pp. 111753-11757, Oct. 1997.
Mathis, Clin. Chem., vol. 41, No. 9, *Probing Molecular Interactions with Homogeneous Techniques Based on Rare Earth Cryptates and Fluorescence Energy Transfer*, pp. 1391-1397, 1995.
Ozers et al., J. of Biol. Chem., vol. 272, No. 48, *Equilibrium Binding of Estrogen: Receptor with DNA Using Fluorescence Anistropy*, pp. 30405-30411, Nov. 28, 1997.
Parkhurst et al., Biochemistry, vol. 35, *Simultaneous Binding and Bending of Promoter DNA by the TATA Binding Protein: Real Time Kinetic Measurements*, pp. 7459-7465, 1996.

(Continued)

Primary Examiner—James Martinell

(57) ABSTRACT

Biosensors and methods to determine the activity of any and all nucleic acid binding factors, proteins, cellular events, nucleic acid binding protein coregulators, or fragments thereof, based upon the stabilization of the interaction of two nucleic acid components, which together comprise a complete nucleic acid binding element, by the binding of a nucleic acid binding factor are provided. Preferably, a fluorescence donor is attached to a nucleic acid comprising one portion or component of a complete nucleic acid binding element and a fluorescence acceptor is attached to a nucleic acid comprising the other portion or component of the same complete binding element. Alternatively, a solid substrate is attached to a nucleic acid comprising one portion of a binding element and a detectable label is attached to a nucleic acid comprising the other portion of the same binding element. Binding of a nucleic acid binding factor to the nucleic acid components affects a change in luminescence or the association of the detectable label with the solid substrate. These biosensors and methods may also be used to detect mediating nucleic acid binding factor coregulators, post-translational modifications and cellular events, to diagnose diseases and/or screen for drugs or other ligands that mediate the activity of nucleic acid binding factors.

21 Claims, 24 Drawing Sheets

OTHER PUBLICATIONS

Reedstrom et al., J. Mol. Biol., vol. 273, *Affinity and Speficity of trp Repressor-DNA Interactions Studied with Fluorescent Oligonucleotides*, pp. 572-585, 1997.

Sha et al., J. of Biol. Chem., vol. 270, No. 33, *Anti-cooperative Biphasic Equilibrium Binding of Transcription Factor Upstream Stimulatory Factor to its Cognate DNA Monitored by Protein Fluorescence Changes*, pp. 19325-19329, Aug. 18, 1995.

Stryer et al., J. of Biol. Chem., vol. 47, *Fluorescence Energy Transfer as a Spectroscopic Ruler*, pp. 819-846, 1978.

Tyagi et al., Nature Biotechnology, vol. 16, *Multicolor molecular beacons for allele discrimination*, pp. 49-53, Jan. 1998.

Wang et al., Biochemistry, vol. 37, *Fluorescence Study of the Multiple Binding Equilibria of the Galactose Repressor*, p. 41-50, 1998.

Weiss, Science, vol. 283, Fluorescence Spectroscopy of Single Biomolecules, pp. 1676-1683, Mar. 12, 1999.

Xu, Proc. Natl. Sci. USA, vol. 96, A bioluminescence resonance energy transfer (BRET) system: Application to interacting circadian clock proteins, pp. 151-156, Jan. 1999.

* cited by examiner

SEQUENCE LISTING

<160> NUMBER OF SEQ ID NOS: 28

<210> SEQ ID NO 1

```
<211> LENGTH: 16
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.

<400> SEQUENCE: 1
aacgcaataa atgtga                                                        16

<210> SEQ ID NO 2
<211> LENGTH: 22
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.
<221> NAME/KEY: modified_base
<222> LOCATION: 3
<223> OTHER INFORMATION: n = t labeled with fluorescein

<400> SEQUENCE: 2
agnagatcac attttaggca cc                                                 22

<210> SEQ ID NO 3
<211> LENGTH: 16
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.

<400> SEQUENCE: 3
ggtgcctaaa atgtga                                                        16

<210> SEQ ID NO 4
<211> LENGTH: 22
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.
<221> NAME/KEY: modified_base
<222> LOCATION: 3
<223> OTHER INFORMATION: n = t labeled with dabcyl

<400> SEQUENCE: 4
tcnacttcac atttattgcg tt                                                 22

<210> SEQ ID NO 5
<211> LENGTH: 30
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.

<400> SEQUENCE: 5
cctaaaatgt gatctagatc acatttattg                                         30
```

<210> SEQ ID NO 6
<211> LENGTH: 30
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.

<400> SEQUENCE: 6
gcatcggtca ctgcagtctc gacagctacg                                      30

<210> SEQ ID NO 7
<211> LENGTH: 22
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.
<221> NAME/KEY: modified_base
<222> LOCATION: 3
<223> OTHER INFORMATION: n = amino modified thymine

<400> SEQUENCE: 7
agnagatcac attttaggca cc                                              22

<210> SEQ ID NO 8
<211> LENGTH: 22
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.
<221> NAME/KEY: modified_base
<222> LOCATION: 3
<223> OTHER INFORMATION: n = amino modified thymine

<400> SEQUENCE: 8
tcnacttcac atttattgcg tt                                              22

<210> SEQ ID NO 9
<211> LENGTH: 38
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.
<221> NAME/KEY: modified_base
<222> LOCATION: 2
<223> OTHER INFORMATION: n = fluorescein labeled thymine
<221> NAME/KEY: misc_feature
<222> LOCATION: 21...22
<223> OTHER INFORMATION: a non-nucleotide spacer element, 18-O-
      Dimethoxytritylhexaethyleneglycol,1-
      [(2-cyanoethyl)-(N,N-diisopropyl)]-phosphoramidite, is covalently
      inserted between nucleotides 21 and 22

<400> SEQUENCE: 9
cnagatcaca ttttaggcac caacgcaata aatgtgat                             38

<210> SEQ ID NO 10
<211> LENGTH: 21
<212> TYPE: DNA

```
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.
<221> NAME/KEY: modified_base
<222> LOCATION: 2
<223> OTHER INFORMATION: n = dabcyl labeled thymine

<400> SEQUENCE: 10
cnagatcaca tttattgcgt t                                            21

<210> SEQ ID NO 11
<211> LENGTH: 17
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.

<400> SEQUENCE: 11
ggtgcctaaa atgtgat                                                 17

<210> SEQ ID NO 12
<211> LENGTH: 17
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.

<400> SEQUENCE: 12
ggtgtgtgga attgtga                                                 17

<210> SEQ ID NO 13
<211> LENGTH: 22
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.
<221> NAME/KEY: modified_base
<222> LOCATION: 4
<223> OTHER INFORMATION: n = fluorescein labeled thymine

<400> SEQUENCE: 13
gcgnataaca atttcacaca gg                                           22

<210> SEQ ID NO 14
<211> LENGTH: 16
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.

<400> SEQUENCE: 14
cttgtgtgaa attgtt                                                  16

<210> SEQ ID NO 15
```

```
<211> LENGTH: 23
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.
<221> NAME/KEY: modified_base
<222> LOCATION: 2
<223> OTHER INFORMATION: n = dabcyl labeled thymine

<400> SEQUENCE: 15
anacgctcac aattccacac acc                                          23

<210> SEQ ID NO 16
<211> LENGTH: 16
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.

<400> SEQUENCE: 16
gagatctatc gaacta                                                  16

<210> SEQ ID NO 17
<211> LENGTH: 22
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.
<221> NAME/KEY: modified_base
<222> LOCATION: 2
<223> OTHER INFORMATION: n = fluorescein labeled thymine

<400> SEQUENCE: 17
gnaaactagt acgaaactag ag                                           22

<210> SEQ ID NO 18
<211> LENGTH: 16
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.

<400> SEQUENCE: 18
ctctagtttc gtacta                                                  16

<210> SEQ ID NO 19
<211> LENGTH: 22
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.
<221> NAME/KEY: modified_base
<222> LOCATION: 2
<223> OTHER INFORMATION: n = dabcyl labeled thymine

<400> SEQUENCE: 19
```

```
gnttactagt tcgatagatc tc                                          22
```

<210> SEQ ID NO 20
<211> LENGTH: 16
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.

<400> SEQUENCE: 20

```
gcatcggtca cagaca                                                 16
```

<210> SEQ ID NO 21
<211> LENGTH: 26
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.
<221> NAME/KEY: modified_base
<222> LOCATION: 5
<223> OTHER INFORMATION: n = fluorescein labeled thymine

<400> SEQUENCE: 21

```
tgccnagaca tgccttgcag tctcga                                      26
```

<210> SEQ ID NO 22
<211> LENGTH: 16
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.

<400> SEQUENCE: 22

```
tcgagactgc aaggca                                                 16
```

<210> SEQ ID NO 23
<211> LENGTH: 26
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.
<221> NAME/KEY: modified_base
<222> LOCATION: 5
<223> OTHER INFORMATION: n = dabcyl labeled thymine

<400> SEQUENCE: 23

```
tgtcnaggca tgtctgtgac cgatgc                                      26
```

<210> SEQ ID NO 24
<211> LENGTH: 10
<212> TYPE: DNA
<213> ORGANISM: Homo sapiens
<220> FEATURE:
<221> NAME/KEY:
<222> LOCATION:
<223> OTHER INFORMATION: These sequences were chemically synthesized,
      but may also be created via recombinant methods.

```
<400> SEQUENCE: 24 rrrcwwgyyy                                                              10

<210> SEQ ID NO 25
<211> LENGTH: 16
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.
<221> NAME/KEY: modified_base
<222> LOCATION: 1
<223> OTHER INFORMATION: n = amino labeled thymine

<400> SEQUENCE: 25
naacgcaata aatgtg                                                       16

<210> SEQ ID NO 26
<211> LENGTH: 23
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.

<400> SEQUENCE: 26
atctacttca catttattgc gtt                                               23

<210> SEQ ID NO 27
<211> LENGTH: 23
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.
<221> NAME/KEY: modified_base
<222> LOCATION: 3
<223> OTHER INFORMATION: n = biotin labeled cytosine

<400> SEQUENCE: 27
aagtagatca cattttaggc acn                                               23

<210> SEQ ID NO 28
<211> LENGTH: 15
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.

<400> SEQUENCE: 28
ggtgcctaaa atgtg                                                        15
```

RAPID AND SENSITIVE ASSAY FOR THE DETECTION AND QUANTIFICATION OF COREGULATORS OF NUCLEIC ACID BINDING FACTORS

CROSS REFERENCE TO RELATED APPLICATIONS

This application is a continuation-in-part of U.S. patent application Ser. No. 09/928,385, filed on Aug. 13, 2001 now U.S. Pat. No. 6,544,746, which is hereby incorporated herein in its entirety by reference.

GOVERNMENTAL SUPPORT

This work was supported by the U.S. Department of Health and Human Services/National Institutes of Health grant number GM50514. The U.S. Government has certain rights in this invention.

SEQUENCE LISTING

A paper copy of the sequence listing and a computer readable form of the same sequence listing are appended below and herein incorporated by reference. The information recorded in computer readable form is identical to the written sequence listing, according to 37 C.F.R. 1.821 (f).

BACKGROUND OF THE INVENTION

1. Field of the Invention

The invention relates generally to biosensors and methods of detecting and quantifying specific proteins, factors and chemical ligands, in particular sequence-specific nucleic acid binding factors and their coregulators, by changes in luminescence signal intensity or by detection of a detectable label. The invention is used in any application where the determination of the activity of a nucleic acid binding factor or of a coregulator thereof is desired.

2. Description of the Related Art

The ability to detect and quantify specific chemicals and chemical moieties, especially nucleic acid binding factors and their coregulators is of great importance in basic research and in clinical applications. Determination of the level of a specific protein or other biomolecule is one of the most useful and important experimental procedures in biomedical research and molecular diagnostics. Cellular levels of specific proteins or cofactors are commonly used as diagnostic markers for many diseases.

Protein-nucleic acid interactions are an extremely important and physiologically relevant type of macromolecular contact found in the cell. Many proteins that play an important role in regulating many processes in prokaryotic cells, eukaryotic cells, and viruses possess natural sequence-specific nucleic acid binding activity. These proteins include transcription factors, chromatin remodeling factors and DNA maintenance enzymes. For a review of nucleic acid binding factors, see Benjamin Lewin, *Genes VII*, Oxford University Press, New York, 2000, which is herein incorporated by reference.

Transcription factors bind to specific cognate nucleic acid elements, which include promoters, enhancers and silencer elements. They may be activators, repressors or both, depending on the cellular context, whose levels are important for regulation of gene expression. Thus, many of these proteins are important in disease development and disease diagnosis. For example, several transcription factors, which when overexpressed or inappropriately expressed, are oncogenes. These oncogenic transcription factors include myc, myb, fos, jun, rel and erb. Another cancer related transcription factor, p53, is involved in development of many cancers (Ko, L. L., and Prives, C. *Genes Dev.* 10, 1054–1072, 1996).

Chromatin remodeling factors are also important for the regulation of gene expression. Generally, regions of highly condensed chromatin, called heterochromatin, contain genes that are not actively transcribed, whereas regions of loose or non-condensed chromatin, called euchromatin, contain genes that are actively transcribed. During cellular differentiation, cancerous transformation and normal physiological homeostasis, chromatin may be remodeled. That is, some chromosomal regions become inaccessible to transcription factors and RNA polymerase, whereas other regions become accessible. Several nucleic acid binding factors are involved in this dynamic process including nucleosome proteins (e.g., histones), histone acetyltransferases, histone deacetylases, amino acid methyltransferases, DNA methyltransferases, nucleoplasmins, HMG proteins, repressor complex proteins, polycomb-related factors and trithorax-related factors.

DNA maintenance enzymes are nucleic acid binding factors necessary for the repair of damaged DNA, faithful replication of DNA and exchange of genetic information during recombination. Several types of cancer and other disease syndromes are the result of defective DNA maintenance enzymes. For example, Xeroderma pigmentosum, a horrific genetic disease whereby the sufferer is predisposed to skin cancer, is due to defective nucleotide-excision repair enzymes. Hereditary non-polyposis colorectal cancer is caused in large part by defective mismatch repair enzymes. Some forms of hereditary breast cancers are due to defective homologous recombination enzymes. For a review of genome maintenance systems and their role in cancer, see Hoeijmakers, J. H. J., *Nature* 411, 366–374, 2001, which is herein incorporated by reference. Thus, there is a significant interest in convenient and accurate methods for detecting, monitoring and/or quantifying nucleic acid binding activity of nucleic acid binding factors and their coregulators.

The most common approaches taken to detect proteins exhibiting sequence-specific nucleic acid binding activity are gel shift assays and various nucleic acid footprinting assays (Fried, M. G., and Crothers, D. M. *Nucleic Acids Res.* 9, 6505–6525, 1981; Galas, D. J., and Schmitz, A. *Nucleic Acid Res.* 5, 3157–3170, 1978). These methods are laborious and time-consuming procedures, which typically involve the use of dangerous and expensive radioisotopes. Furthermore, these methods are not generally adaptable to high-throughput assay formats. Different fluorescence based methodologies for detecting and studying nucleic acid binding factors have been developed to overcome the deficiencies of gel shift and nucleic acid footprinting assays.

Detection of molecules by fluorescence has several advantages compared to alternative detection methods. Fluorescence provides an unmatched sensitivity of detection, as demonstrated by the detection of single molecules using fluorescence (Weiss, S. *Science* 283, 1676–1683, 1999). Detection of fluorescence, changes in fluorescence intensity or changes in emission spectra can be easily achieved by the selection of specific wavelengths of excitation and emission. Fluorescence provides a real-time signal allowing real-time monitoring of processes and real-time cellular imaging by microscopy (see Lakowicz, J. R. *Principles of Fluorescence Spectroscopy*, Kluwer Academic/Plenum Press, New York, 1999, which is herein incorporated by reference). Additionally, well-established methods and instrumentation for high-throughput detection of fluorescence signals exist in the art.

Current methods for detecting nucleic acid binding factors in solution using fluorescence rely on one of the following phenomena: (i) a change in the fluorescence intensity of a fluorochrome (also called a fluorophore or a fluorescent probe or label), which is present either on the protein or on the nucleic acid, as a result of the perturbation of the microenvironment of the probe upon protein-nucleic acid complex formation; (ii) a change of fluorescence polarization of the fluorochrome, which is present either on the protein or on the nucleic acid, as a result of an increase in the molecular size of the protein-nucleic acid complex relative to the unbound nucleic acid or protein molecules; and (iii) resonance energy transfer between one fluorochrome present in nucleic acid and another fluorochrome or fluorescence quencher present in a protein as a result the proximity between nucleic acid and the protein in protein-nucleic acid complex. For a review on methods of detecting fluorescence signal detection, see Hill, J. J., and Royer, C. A. *Methods in Enzymol.* 278, 390–416 (1997), which is herein incorporated by reference. Examples of the application of a change in fluorescence intensity of a fluorchrome to the detection of protein-nucleic acid complexes using fluorochromes attached to the protein or the nucleic acid can be found in the following technical literature, which are herein incorporated by reference (Sha, M., Ferre-D'Amare, Burley, S. K., and Goss, D. J. *J. Biol. Chem.* 270, 19325–19329, 1995; Reedstrom, R. J., Brown, M. P., Grillo, A., Roen, D, and Royer, C. A. *J. Mol. Biol.* 273, 572–585, 1997; Erickson, G. H, and Daksis, J. WO 00/40753).

Another type of fluorescence-based detection assay, called fluorescence polarization, has also been used for the detection of protein-nucleic acid complex formation (see Heyduk, T., and Lee, J. C. *Proc. Natl. Acad. Sci USA* 87, 1744–1748, 1990, which is herein incorporated by reference). The physical basis of this approach is that the fluorescence polarization signal of a macromolecule labeled with a fluorochrome depends on the size of the macromolecule (Lakowicz, J. R. *Principles of Fluorescence Spectroscopy*, Kluwer Academic/Plenum Press, New York, 1999, herein incorporated by reference). Hence, upon the formation of a protein-nucleic acid complex from the protein and nucleic acid components, a larger molecular entity is created, which has an altered fluorescence signature. The use of fluorescence polarization to detect protein-nucleic acid complexes is described in Royer (1998, U.S. Pat. No. 5,756, 292), which is herein incorporated by reference.

A third fluorescence-based assay for the detection of the protein-nucleic acid complex formation is fluorescence resonance energy transfer (FRET) (Stryer, L. *Ann. Rev. Biochem.* 47, 819–846, 1978, which is herein incorporated by reference). FRET is based upon the transfer of emitted light energy from a fluorochrome (fluorescent donor) to an acceptor molecule (fluorescent acceptor), which may also be a fluorochrome. As used in the detection of nucleic acid-protein binding events, the FRET assay is based on the increased proximity between a fluorochrome attached to the DNA binding protein and the fluorochrome attached to the cognate DNA binding element when a binding event has occurred. Several published reports illustrate the use of this approach to detect and study protein-nucleic acid interactions (see Kane, S. A., Fleener, C. A., Zhang, Y. S., Davis, L. J., Musselman, A. L., and Huang, P. S. *Anal. Biochem.* 278, 29–39, 2000, which is herein incorporated by reference).

In summary, luminescence or fluorescence-based assay systems are attractive tools for detecting nucleic acid binding proteins. The inventor describes herein a general, inexpensive, simple, multicolor or single color fluorescence, luminescence, radiographic, gravimetric or colorimetric method for detecting sequence specific nucleic acid binding factors or coregulators thereof, which are compatible with high-throughput detection formats.

SUMMARY OF THE INVENTION

This invention is based upon the concept that a nucleic acid binding factor can stabilize the interaction between two or more nucleic acid binding element "half-sites" or components, wherein the two or more components together make up a complete binding site that is able to associate with a cognate nucleic acid binding factor. Thus, this invention may be used as a "biosensor" to assess the activity (i.e., detect the presence or quantity of) nucleic acid binding factors or coregulators of nucleic acid binding factors in a sample. To detect nucleic acid binding factors in a sample, the sample is simply mixed with or added to the nucleic acid components. To detect coregulators in a sample, the sample is mixed with or added to the nucleic acid components and the cognate nucleic acid binding factor, wherein the activity of the binding factor is mediated by the coregulators. The coregulator will activate or deactivate the binding factor, thereby indirectly mediating the association of the nucleic acid components into a complete binding site. Many different permutations or embodiments may be used in the operation of this invention (FIG. 1).

Any and all known methods of detection and detectable labels may be used to detect the association or disassociation of the nucleic acid components. At least four major modes of detection may be used in the operation of this invention, although the skilled artisan may reasonably expect any mode of detection to work in the practice of this invention. The first mode of detection is based upon proximity-based methods of detection, including for example fluorescence resonance energy transfer, fluorescence quenching, or the like (FIG. 1A, C and D). The second mode is based upon coincidence-based methods of detection, including for example fluorescence cross-correlation spectroscopy or the like (FIG. 1B). The third mode is based upon the capture of a detectable label to a solid support, including for example flow cytometry (wherein a nucleic acid component is attached to a bead or labeled nucleic acid components are placed inside of a cell), autoradiography or the like (FIG. 1E). The fourth mode is based upon methods of detecting changes in mass concentration that occurs on the surface of a sensor, including for example surface plasmon resonance detection or the like (FIG. 1F).

Disclosed are methods of detecting and quantifying nucleic acid binding factors and coregulators thereof based upon proximity-based luminescence transfer. In one embodiment of the invention, two double-stranded oligonucleotides are synthesized or isolated, such that, by combining the two double-stranded oligonucleotides, a complete nucleic acid element is formed across the juncture of the oligonucleotides (see FIG. 1A). The nucleic acid binding element comprises a cognate sequence for the binding of nucleic acid binding factors. The first oligonucleotide is labeled with a fluorochrome, which is hereafter referred to as the "fluorescent donor", and the second oligonucleotide is labeled with a fluorescent quenching molecule, which is hereafter referred to as "fluorescent acceptor", wherein said quenching molecule may be another fluorochrome of a lower excitation wavelength than the first fluorochrome. The fluorescent-labeled oligonucleotides are mixed with a sample, which may or may not contain a nucleic acid binding factor. Upon mixing, and if present, the nucleic acid binding factor associates with both components of its cognate nucleic acid element, thereby stabilizing the association of the two components. When the two components are in close proximity, the fluorescent donor of the first nucleic acid component transfers its emitted light energy to the fluorescent acceptor of the second nucleic acid component, resulting in the quenching of the emitted light from the fluorescent donor. Fluorescence is measured using standard spectrophotometric or fluorometric methods that are well known in the art. The quenching of the fluorescent signal correlates with the association of the nucleic acid binding factor to the cognate nucleic acid element.

Given that fluorescence and fluorescence quenching are routinely measured with accuracy and precision, the present invention may be used to quantify the amount or specific activity of a nucleic acid binding factor in a sample, quantify the dissociation constant or affinity of a nucleic acid binding factor to its cognate binding element, or detect the presence of a nucleic acid binding factor in a sample by measuring the change in fluorescence wavelength or intensity.

In another embodiment, the labeled nucleic acid components (or oligonucleotide "half-sites") that comprise a nucleic acid binding element are in solution and free to diffuse in all directions. In another embodiment, said nucleic acid components are affixed to a solid phase substrate, such as, for example, a multiwell plate, microarray slide, membrane, microsphere, or the tip of a light guide, optical fiber, conducting material or biosensor device. In another embodiment, each pair or set of matched oligonucleotides are connected via a linker molecule, wherein the first oligonucleotide is linked to the second oligonucleotide by way of a linker molecule attached to the end of each oligonucleotide, which end is distal to the nucleic acid binding element or fluorescently tagged end of each oligonucleotide. The linked oligonucleotide pairs (1) may be affixed to a solid phase substrate, such as a multiwell plate, membrane, microarray device, the tip of a light guide, optical fiber, conducting material or biosensor device, or microsphere, (2) may be free to diffuse in solution, or (3) may be delivered into a cell, wherein the cell may a prokaryotic cell or an eukaryotic cell.

In another embodiment, a single polynucleotide is labeled in two positions, with a fluorescent donor at the first position and with a fluorescent acceptor at the second position, wherein the fluorescent labels are at such a distance from one another so as not to interact spectroscopically in the absence of a bridging nucleic acid binding factor. In one aspect of this embodiment a portion (component) of a nucleic acid element is located near the first position and another portion (component) of the same nucleic acid element is located near the second position. Upon the binding of a nucleic acid binding factor to both portions of said nucleic acid element, the first position is brought into proximity to the second position, thereby facilitating or stabilizing the spectroscopic interaction between fluorescent donor and fluorescent acceptor. In another aspect of this embodiment, a first complete nucleic acid element is located at or near the first position and a second complete nucleic acid element is located at or near the second position. Upon the binding of a nucleic acid binding factor or complex assembly of nucleic acid binding factors (as in an enhanceosome, for example) to the first and second element, the first position is brought into proximity to the second position, thereby facilitating or stabilizing the spectroscopic interaction between fluorescent donor and fluorescent acceptor, resulting in a measurable change in fluorescence due to fluorescent energy transfer or quenching.

Any method of proximity-based or coincident-based luminescence detection may be used in the present invention. Embodiments include, but are not limited to, fluorescence energy transfer, luminescence resonance energy transfer, fluorescence cross-correlation spectroscopy, flow cytometry, direct quenching, ground-state complex formation, chemiluminescence energy transfer, bioluminescence energy transfer and excimer formation. It is understood that the skilled artisan, upon consideration or practice of this invention, will recognize alternative detection methods known in the art that may be applicable to the present invention and are thus included in this invention.

Any fluorochrome may be used as a fluorescent donor or acceptor in the present invention, however it is preferred that the acceptor excitation wavelength matches the emission wavelength of the donor. In another embodiment, a quencher molecule may be used as a fluorescence acceptor, wherein no light is emitted from the quencher upon excitation. Examples of fluorochromes and quenchers are included in the group consisting of Alexa Fluor® 350, Alexa Fluor® 430, Alexa Fluor® 488, Alexa Fluor® 532, Alexa Fluor® 546, Alexa Fluor® 568, Alexa Fluor® 594, Alexa Fluor® 633, Alexa Fluor® 647, Alexa Fluor® 660, Alexa Fluor® 680, 7-diethylaminocoumarin-3-carboxylic acid, Fluorescein, Oregon Green 488, Oregon Green 514, Tetramethylrhodamine, Rhodamine X, Texas Red dye, QSY 7, QSY33, Dabcyl, BODIPY FL, BODIPY 630/650, BODIPY 650/665, BODIPY TMR-X, BODIPY TR-X, Dialkylaminocoumarin, Cy5.5, Cy5, Cy3.5, Cy3, DTPA(Eu3+)-AMCA and TTHA (Eu3+)-AMCA. It is understood that the skilled artisan would recognize that any compatible fluorescence donor/acceptor pair will work in the present invention and that the aforementioned fluorochromes and quenchers are exemplary and not limiting.

In another embodiment, in addition to luminescence-based proximity assays, flow cytometry and calorimetric enzyme-based assays may be used to detect binding of a nucleic acid binding factor to a cognate nucleic acid element. In fluorescence assisted cell sorting, one nucleic acid component is coupled to a bead or microsphere and the other nucleic acid component is coupled to a luminescent molecule or fluorochrome.

In another embodiment, a labeled nucleic acid components may be inserted into a cell, such as a prokaryotic cell or an eukaryotic cell, wherein the cell comprises nucleic acid binding factors or coregulators thereof. Changes in a detectable signal emanating from said cell would indicate a nucleic acid binding event.

In another embodiment, the present invention is used to diagnose and or characterize disease states by profiling the activity of various diagnostic nucleic acid binding factors in a sample obtained from a patient. Some diseases involve the misexpression of nucleic acid binding factors. For example, some cancers involve the overexpression of transcription factors such as c-myc, c-fos, c-jun, rel or erbA (see Genes IV by Lewin, p. 890), while other cancers, for example some types of breast cancer or colorectal cancers, underexpress DNA repair enzymes. In this embodiment, biopsy samples are combined with labeled oligonucleotides or nucleic acid components, as herein described above, to assay for the presence, absence or specific activity of specific nucleic acid binding factors.

In another embodiment, the present invention is directed to a method of detecting and/or quantifying cell regulatory factors in a sample, wherein said cell regulatory factors act as coregulators that facilitate or abrogate the association of nucleic acid binding factors to cognate nucleic acid elements. A test sample that may contain a regulatory factor is combined with a mixture or kit comprising the labeled oligonucleotides or polynucleotides of the present invention and the cognate nucleic acid binding factor, wherein the nucleic acid binding activity of the nucleic acid binding factor depends fully or in part on the presence or absence of said coregulator. If the nucleic acid binding factor requires the presence of said coregulator in order to bind to the cognate nucleic acid element, fluorescence energy transfer or quenching will occur when the regulatory factor is present in the sample. Likewise, if said coregulator interferes with the binding of the nucleic acid binding factor to its cognate nucleic acid element, fluorescence energy transfer or quenching will not occur.

In another embodiment, the present invention is drawn to a method of identifying agents, drugs, contaminants or pollutants that affect the binding of nucleic acid binding factors to nucleic acid elements. These agents, drugs, contaminants or pollutants are also considered to be coregulators of nucleic acid binding factors. In a situation analogous to the method of detecting and/or quantifying cell regulatory factors or coregulators in a sample (supra), prospective agents, drugs, contaminants or pollutants are combined with various sets of nucleic acid binding factors and labeled oligonucleotides or nucleic acid components comprising cognate nucleic acid elements. In the event that the agent, drug, contaminant or pollutant inhibits or disrupts interaction of the nucleic acid binding factor with the complete nucleic acid element, no change in fluorescence would be measured. In the event that the agent, drug, contaminant or pollutant augments the binding of the nucleic acid binding factor to the complete nucleic acid element, an enhancement of the fluorescence energy transfer or change in fluorescence would be measured.

In another embodiment, the invention is drawn to an array device comprising multiple pairs of labeled oligonucleotides affixed to a solid matrix or suspended in solution in a linear or multidimensional format. Cognate pairs of labeled nuceic acid components, wherein each component comprises a portion of a complete nucleic acid element that is a binding site for a nucleic acid binding factor and the first label is a fluorescent donor molecule or a chemiluminescent or colorimetric substrate and the second label is a fluorescent acceptor or catalyst for the chemiluminescent or calorimetric substrate, are affixed to a specific position on a solid substrate or suspended within a specific well of a multiwell plate. The solid substrate may be a membrane, such as, for example nitrocellulose, nylon or polyvinyldifluoride ("PVDF"), a multiwell plate or another convenient substrate, such as the tip of a light guide, optical fiber, conducting material or biosensor device, that lends itself to this purpose. In another aspect of this embodiment, each cognate pair of components is linked together by way of a linker molecule affixed to the end of each oligonucleotide distal to the label. The linked oligonucleotide pairs are affixed to the solid matrix in a specific array format or are placed within specific wells of a multiwell plate. In another aspect of this embodiment, the array device comprises several nucleic acid components displayed in an array format, wherein each polynucleotide comprises one or several nucleic acid elements that are labeled, wherein the first label is a fluorescent donor molecule or a chemiluminescent or calorimetric substrate and the second label is a fluorescent acceptor or catalyst for the chemiluminescent or calorimetric substrate. Each specific polynucleotide is affixed to a specific position on a solid substrate or suspended within a specific well of a multi-well plate, as described for the oligonucleotide pairs (supra).

This invention is also drawn to biosensors for the detection of nucleic acid binding factors and coregulators thereof, and methods of detecting nucleic acid binding factors and coregulators thereof using non-proximity based detection methods. The inventor envisions that only one nucleic acid component is attached to a detectable label. That label may be any detectable label, for example a fluorochrome, chromophore, enzyme, linker molecule such as biotin, HRPO, or radionuclide. For example, in the case in which the detectable label is a fluorochrome, a binding event may be detected by fluorescence quenching or polarization, as discussed above. In the case in which the detectable label is biotin, a binding event may be detected by using an avidin-peroxidase development system. In an alternative embodiment, the first nucleic acid component is attached to a solid substrate, such as a bead, glass slide, membrane or multiwell plate, and the second nucleic acid component is attached to a detectable label. In a positive binding event, the labeled nucleic acid component becomes attached to the solid substrate, which can be subsequently subjected to colorimetric staining, fluorescence detection or autoradiography, depending upon the type of detectable label used.

It is further envisioned that the first nucleic acid component is attached to a biosensor surface such that the association of a binding factor to the complete binding element causes a change in the overall mass that is associated with the surface. The change in mass may be detected by changes in reflected light emanating from the surface of the biosensor, such as in surface plasmon resonance.

The above summary describes in brief the preferred embodiments of the present invention and is not intended to limit the scope of the invention to these described embodiments. The skilled artisan will recognize that there are other possible embodiments of this invention, which utilize the general principle of a nucleic acid binding factor facilitating the association of two nucleic acid components, wherein each component comprises a portion of a complete nucleic acid binding element.

DETAILED DESCRIPTION OF THE INVENTION

Definitions

Figure 1:
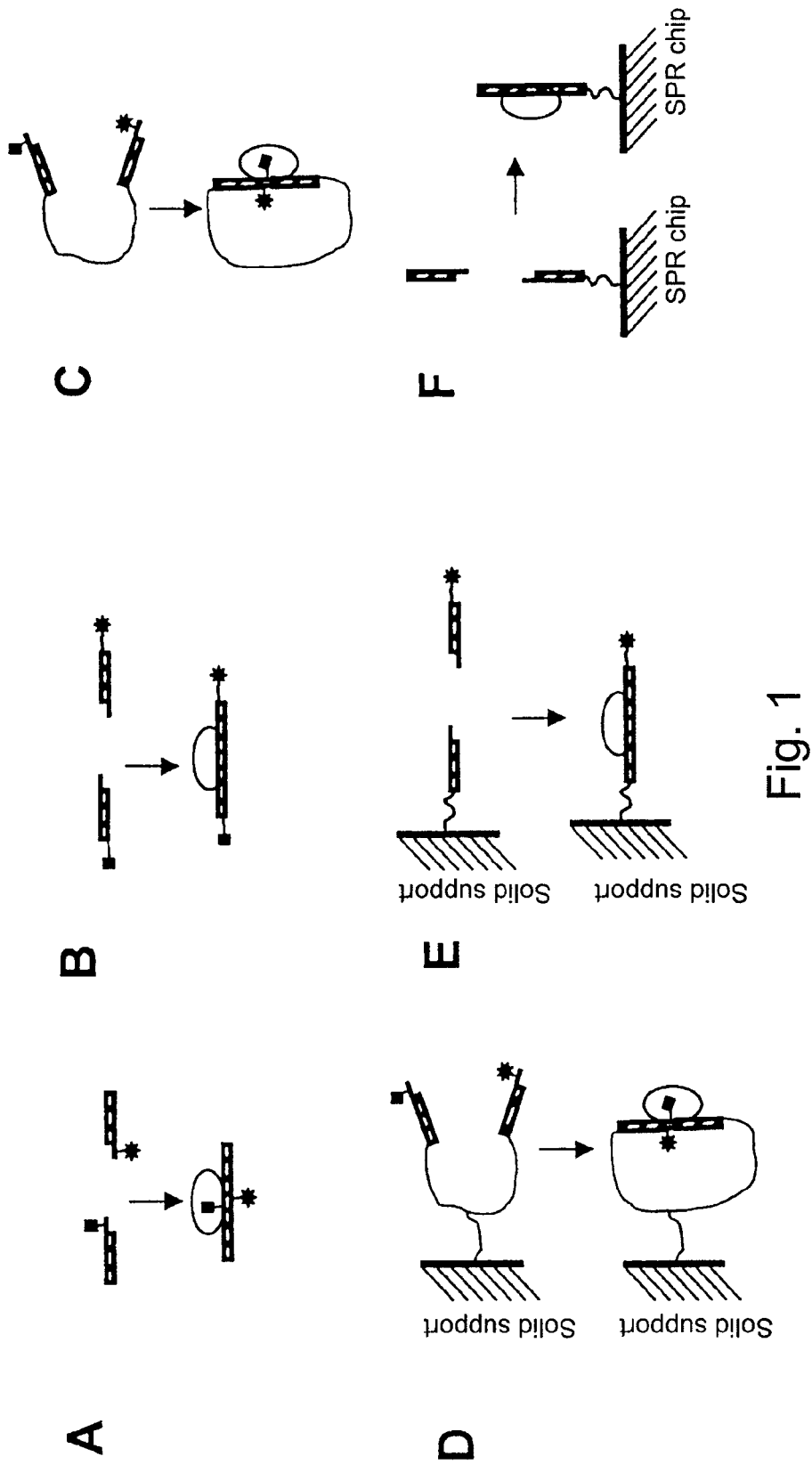
FIG. 1 depicts the overall design of the biosensor for nucleic acid binding factors or coregulators as herein described. 1A depicts the basic two-component system that relies on a proximity-based detection assay, wherein the first nucleic acid component is attached to an energy donor and the second component is attached to an energy acceptor. 1B depicts the basic two-component system that relies on a coincidence-based detection assay. 1C depicts a biosensor design wherein two nucleic acid components are joined together by way of a flexible linker molecule. 1D depicts a modified version of a linked two-component biosensor, wherein the linked components are attached to a solid support. 1E depicts a version of the biosensor wherein the first component is attached to a solid support and the second component is attached to a detectable label. 1F depicts a version of the biosensor wherein the first component is attached to a surface and the method of detection relies upon detecting a change in mass at the surface.

Although any methods or materials similar or equivalent to those described herein can be used in the practice or testing of the present invention, the preferred methods and materials are described. For the purposes of the present invention, the following terms are defined below.

As used herein, "label", "detectable label" or "probe" refers to any chemical moiety attached to a nucleotide, nucleotide polymer, or nucleic acid binding factor, wherein the attachment may be covalent or non-covalent. Preferably, the label is detectable and renders said nucleotide or nucleotide polymer detectable to the practitioner of the invention. Detectable labels include luminescent molecules, chemiluminescent molecules, fluorochromes, fluorescent quenching agents, colored molecules, radioisotopes or scintillants. Detectable labels also include any useful linker molecule (such as biotin, avidin, streptavidin, HRPO, protein A, protein G, antibodies or fragments thereof, Grb2, polyhistidine, $Ni^{2+}$, FLAG tags, myc tags), heavy metals, enzymes (examples include alkaline phosphatase, peroxidase and luciferase), electron donors/acceptors, acridinium esters, dyes and colorimetric substrates. It is also envisioned that a change in mass may be considered a detectable label, as is the case of surface plasmon resonance detection. The skilled artisan would readily recognize useful detectable labels that are not mentioned above, which may be employed in the operation of the present invention.

The phrase "detection method" or "method of detection" refers to the manner in which the association of a nucleic acid binding factor to a complete nucleic acid binding element is visualized. The detection method is inextricably linked to the nature of the detectable label. For example, if a second nucleic acid component is attached to a radionuclide such as $^{33}P$ and the first nucleic acid component is attached to a solid substrate such as a nylon membrane, then a detectable method may be beta particle detection via autoradiography or radioscintigraphy. If a first nucleic acid component is attached to the well of a multiwell plate, and the second nucleic acid is attached to a biotin, then a detectable method may be an avidin-peroxidase or avidin-alkaline phosphatase detection kit, which kits are commercially available and well known in the art. The multiwell plate may then be subjected to colorimetric analysis in a plate reader. If a first nucleic acid element is attached to a fluorescence donor and the second nucleic acid is attached to a fluorescence acceptor, then the detection method may be a proximity-based assay such as FRET. The method of detection may involve the detection of a change of mass, as in surface plasmon resonance. For example, one or all nucleic acid components may be attached to a sensor chip surface such that the association of a nucleic acid binding factor induces a change in the mass of the surface that results in a change in optical resonance of the sensor chip surface. Surface plasmon resonance is discussed in Abery, J., "Detecting the Molecular Ties that Bind," *Modern Drug Discovery* 4:34–36 (2001), and references therein, which are incorporated herein by reference. The aforementioned detection methods serve as illustrations only and do not limit the invention to only those detection methods. Other useful detection methods, which may be employed in the operation of this invention, are known to the skilled artisan.

As used herein, the term "luminescence" or "luminescent" means any process of light emission, including fluorescence, phosphorescence, scintillation, chemiluminescence and bioluminescence.

As used herein, "fluorochrome" refers to a fluorescent compound that emits light upon excitation by light of a shorter wavelength than the light that is emitted. The term "fluorescent donor" or "fluorescence donor" refers to a fluorochrome that emits light that is measured in the assays described in the present invention. More specifically, a fluorescent donor provides light that is absorbed by a fluorescence acceptor. The term "fluorescent acceptor" or "fluorescence acceptor" refers to either a second fluorochrome or a quenching molecule that absorbs light emitted from the fluorescence donor. The second fluorochrome absorbs the light that is emitted from the fluorescence donor and emits light of longer wavelength than the light emitted by the fluorescence donor. The quenching molecule absorbs light emitted by the fluorescence donor.

Any luminescent molecule, preferably a fluorochrome and/or fluorescent quencher may be used in the practice of this invention, including, for example, Alexa Fluor® 350, Alexa Fluor® 430, Alexa Fluor® 488, Alexa Fluor® 532, Alexa Fluor® 546, Alexa Fluor® 568, Alexa Fluor® 594, Alexa Fluor® 633, Alexa Fluor® 647, Alexa Fluor® 660, Alexa Fluor® 680, 7-diethylaminocoumarin-3-carboxylic acid, Fluorescein, Oregon Green 488, Oregon Green 514, Tetramethylrhodamine, Rhodamine X, Texas Red dye, QSY 7, QSY33, Dabcyl, BODIPY FL, BODIPY 630/650, BODIPY 650/665, BODIPY TMR-X, BODIPY TR-X, Dialkylaminocoumarin, Cy5.5, Cy5, Cy3.5, Cy3, DTPA (Eu3+)-AMCA and TTHA(Eu3+)-AMCA.

As used herein, the term "chemiluminescence", "chemiluminescent" or "chemiluminescent substrate" refers to a chemical that produces light as a result of a chemical reaction. Commonly used chemiluminescent substrates include, for example, luminol (5-amino-2,3-dihydro-1,4-phthalazinedione), lophine (2,4,5-triphenylimidazole), lucigenin (bis-N-methylacridinium), other acridinium esters and luciferin-luciferase. For example, in the art recognized ECL™ detection system of Amersham Co., an acridinium substrate is oxidized by horseradish peroxidase to produce acridinium esters, which react with excess peroxide at an alkaline pH to produce visible chemiluminescence at 430 nm.

As used herein, the term "calorimetric" or "colorimetric substrate" refers to a chemical that produces a change in the light absorbance properties as a result of a chemical reaction that produces a colored product. In one art recognized example, p-nitrophenyl phosphate when hydrolyzed in the presence of alkaline phosphatase produces p-nitrophenol, which absorbs light at 405 nm (yellow). In another example, p-phenylenediamine plus catechol in the presence of peroxidase and peroxide produces a brownish black product.

As used herein, the term "nucleic acid" refers to an oligonucleotide or polynucleotide, wherein said oligonucleotide or polynucleotide may be modified or may comprise modified bases. Oligonucleotides are single-stranded polymers of nucleotides comprising from 2 to 60 nucleotides. Polynucleotides are polymers of nucleotides comprising two or more nucleotides. Polynucleotides may be either double-stranded DNAs, including annealed oligonucleotides wherein the second strand is an oligonucleotide with the reverse complement sequence of the first oligonucleotide, single-stranded nucleic acid polymers comprising deoxythymidine, single-stranded RNAs, double stranded RNAs or RNA/DNA heteroduplexes.

"Nucleic acid component" as used herein generally refers to an annealed pair of complementary single-stranded oligonucleotides that comprise a portion of a nucleic acid binding element, wherein a complete nucleic acid binding element is formed as a result of the combination of two nucleic acid components. Nucleic acid component also refers to that portion of a polynucleotide that comprises a portion of a nucleic acid binding element, wherein a complete nucleic acid binding element is formed as a result of the combination of two nucleic acid components. Hence, single polynucleotide may comprise both a first and second nucleic acid component. A "set of nucleic acid components" as used herein means a matched set of a first nucleic acid component and a second nucleic acid component, which together comprise a complete nucleic acid binding element upon association of said first and second nucleic acid components. A set of nucleic acid components may comprise more than two components, as in the case for biosensors designed to detect DNA repair enzymes or RNA splicing factors, for example.

A "complete nucleic acid binding element" refers to a nucleic acid sequence of sufficient length and sequence to stably bind to a nucleic acid binding factor. In some embodiments of the invention, a nucleic acid component may comprise a single complete nucleic acid binding element, such that a set of nucleic acid components comprise two or more nucleic acid binding elements that function cooperatively. In such an embodiment, nucleic acid binding factors that bind one or more nucleic acid elements in the presence of transcription factors or other nucleic acid binding factors may be detected. Several sets of nucleic acid components may be combined to detect multiple different nucleic acid binding factors. Further, multiple sets of nucleic acid components may be assembled into an array, which may then be used to screen multiple different nucleic acid binding factors or nucleic acid binding protein coregulators. As used herein, the term "nucleic acid binding element" or "nucleic acid element" refers to a nucleotide sequence that binds to a protein or other moiety. Preferably, the nucleic acid element is a specific nucleotide sequence that binds to a cognate nucleic acid binding protein or factor. The term "cognate" implies a specific recognition between two chemical entities, e.g., a ligand and its cognate receptor or an enzyme and its cognate substrate. Examples of nucleic acid binding elements include promoters, operators, enhancers and silencers, and portions thereof.

As used herein, the term "array" means a linear, two-dimensional or three-dimensional display of unique first nucleic acid components or sets of nucleic acid components. An array may contain first nucleic acid components or sets of nucleic acid components attached to a solid substrate in a discrete pattern, wherein "solid substrate" means a solid, semi-solid or super-cooled liquid surface, substance or matrix. Examples of solid substrates include membranes, plastic multiwell plates, glass slides or fibers, chips, tips of light guides, optical fibers, conducting materials, biosensor devices, or microspheres. It is also envisioned that an array may contain sets of nucleic acid components in solution in discrete wells of a multiwell plate.

As used herein, the term "nucleic acid binding factor" refers to a chemical entity that binds to a nucleic acid. In a preferred embodiment, the nucleic acid binding factor is a protein, polypeptide or fragment of a polypeptide that binds to a cognate nucleic acid binding element, and is hence referred to as a "nucleic acid binding protein". In the most preferred embodiment, the nucleic acid binding factor is a sequence-specific nucleic acid binding protein capable of directly binding to a specific cognate DNA sequence. In other preferred embodiments, a nucleic acid binding protein or factor may be a protein, polypeptide, fragment of a polypeptide or other chemical structure capable of indirectly binding to a nucleic acid element or associating with other nucleic acid binding factors to facilitate or abrogate the function of said other nucleic acid binding factors. Transcription activators, transcription repressors, or other components of enhanceosomes, which do not bind directly to nucleic acids, but are capable of binding to other nucleic acid binding factors to effect gene activity, are included within this definition.

In another embodiment, nucleic acid binding factors and nucleic acid binding protein coregulators are contained within a sample taken from a subject. The subject is preferably a human patient suffering from a type of cancer or other disease of genome instability, wherein the reduction in the activity of DNA repair enzymes may contribute to the development of the disease. The subject may also be an animal, a plant, a microorganism or a cell. The sample is preferably an "extract of cellular materials," which contains nucleic acid binding factors and is preferably devoid of interfering or competing nucleic acid binding elements.

Nucleic acid binding factors may include transcription factors, chromatin remodeling factors and genome maintenance enzymes, among others. A short list and description of the several types of nucleic acid binding factors is described in Benjamin Lewin, *Genes VII*, Oxford University Press, New York, 2000, which is herein incorporated in its entirety by reference.

Transcription factors bind to specific cognate nucleic acid elements such as promoters, enhancers and silencer elements, and are responsible for regulating gene expression. Transcription factors may be activators of transcription, repressors of transcription or both, depending on the cellular context. Transcription factors include, for example, p53, c-myc, c-jun, c-myb, c-fos, c-rel, c-erbA, E2F, β-catenin, cAMP receptor protein ("CAP"), Lac repressor ("LacR"), steroid receptors, homeodomain proteins, POU domain proteins, helix-turn-helix transcription factors, basic helix-loop-helix transcription factors ("bHLH"), basic leucine zipper transcription factors ("bZip"), zinc finger transcription factors and nuclear hormone receptors.

Components of enhanceosomes comprise a subset of transcription factors. As used herein, the term "enhanceosome" refers to a large nucleoprotein complex assembled from several transcription factors cooperatively bound to multiple binding sites in an enhancer. An important component of enhanceosomes is HMG-1, a nucleic acid binding factor that binds to the minor groove of DNA and facilitates bending of the DNA. Enhanceosome proteins include, for example, DNA-bending proteins, HMG box-containing proteins, SRY, LEF-1, HMG-1, HMG-2, transcription factors and basal transcription factors.

As used herein, "basal transcription factors" refer to RNA polymerase II and its associated factors, which are generally known in the art. Basal transcription factors include RNA polymerase II, TFIID, TFIIA, TATA-binding protein, TFIIB, TFIIF, TFIIE, TATA-binding protein-associated factors, NTF-1 and Sp1.

Chromatin-remodeling factors are involved in the maintenance of heterochromatin (or other regions of transcriptionally inactive genes) and euchromatin (or other regions of transcriptionally active genes). They are also involved in the global silencing of stretches of chromosomes and phenomena such as genetic imprinting. Chromatin-remodeling proteins include, e.g., nucleosome proteins (e.g., histones), histone acetyltransferases ("HATs"), histone deacetylases ("HDACs"), amino acid methyltransferases (e.g. arginine methyltransferases), DNA methyltransferases, nucleoplasmins, high mobility group (HMG) proteins, repressor complex proteins, polycomb-related factors and trithorax-related factors, components of the SWI/SNF complex, components of the Sin3 repressor complex, components of the RSC complex, components of the NURF complex, components of the Pc-G complex, components of the trxG complex, CpG methylases, MeCP1 and MeCP2.

Genome-maintenance enzymes are nucleic acid binding factors and other proteins useful in the repair of damaged DNA, faithful replication of DNA or exchange of genetic information during recombination. They include, for example, DNA polymerases, RNA polymerases, base-excision repair enzymes, nucleotide-excision repair enzymes, homologous recombination enzymes, end joining enzymes, mismatch repair enzymes, exonucleases, endonucleases, double-strand break repair enzymes, single-strand break repair enzymes, transcription-coupled repair enzymes, ligation enzymes, translesion synthesis enzymes and enzymes involved in telomere metabolism. For the purposes of this invention, p53 is considered to be a genome-maintenance enzyme as well as a transcription factor, due to its role as a cell cycle check point gene product.

As used herein, the term "activity of a nucleic acid binding factor" is meant to include the specific activity, quantity or affinity for a complete nucleic acid binding element of the nucleic acid binding factor in a sample, and the modulation of the association of pairs of nucleic acid components that comprise a set of nucleic acid components or complete nucleic acid binding element.

As used herein, the term "linker" or "linker molecule" refers to any polymer attached to a set of nucleic acid components, wherein the set of nucleic acid components comprise a complete nucleic acid binding element and wherein the attachment may be covalent or non-covalent. The linker may be a polymer of amino acids, nucleotides, or the like. A preferred linker molecule is flexible and does not interfere with the binding of a nucleic acid binding factor to the set of nucleic acid components. A preferred linker molecule is comprised of 12 moieties of the Spacer 18 phosphoramidate (Glen Research, Sterling, Va.), the structure of which is shown in FIG. 11B.

As used herein, the term "nucleic acid binding protein coregulator" refers generally to a small regulatory compound (ligand), drug, pollutant, heavy metal, contaminant, toxin, any chemical moiety (which may be an ion or molecular compound), cellular event, such as a post-translational modification, or amino acid polymer, i.e. essentially anything that is capable of mediating the association of a nucleic acid binding factor to a nucleic acid element. Nucleic acid binding protein coregulators also include but are not limited to secondary messenger molecules such as, for example, calcium ion, cAMP, nitric oxide (NO) and IP3. Other examples of nucleic acid binding protein coregulators include antibiotics and other drugs, S-adenosylmethionine, steroids, retinoic acid compounds, thyroid hormones, Vitamin D, arsenite and transcriptional coregulators. For further examples of nucleic acid binding protein coregulators, see Clackson, T., "Controlling mammalian gene expression with small molecules," *Curr. Opin. Chem. Biol.* 1:210–218 (1997), Mannervik et al., "Transcriptional coregulators in development," *Science* 284:606–609 (1999) and "Genes VII," Benjamin Lewin, Oxford University Press, which are all incorporated herein by reference. Nucleic acid binding protein coregulators also include cellular events, such as, phosphorylation, lipidation or other post-translational modifications, association with or dissociation from adapter molecules, or proteolysis events that affect or mediate the binding of nucleic acid binding factors to nucleic acid elements. Nucleic acid binding protein coregulator includes those enzymes and moieties that effect cellular events. Nucleic acid binding protein coregulator also refers to any drug, agent, reagent, prospective drug, prospective agent or prospective reagent which mediates the association of a nucleic acid binding factor to a nucleic acid element. "Mediation" or "mediation of association" means the disruption of binding, either partial or full, or facilitation of binding, either partial or full, of a nucleic acid binding factor to a cognate nucleic acid element. For example, a coregulator is said to mediate the activity of a nucleic acid binding factor or to mediate the association of a nucleic acid binding factor to its cognate nucleic acid element if said coregulator causes the nucleic acid binding factor to either (1) bind to its cognate binding element, wherein the binding factor does not bind to its cognate element in the absence of said coregulator, or (2) to disassociate from its cognate binding element, wherein the binding factor will bind to its cognate element in the absence of said coregulator.

As used herein, the term "activity of a nucleic acid binding protein coregulator" includes the specific activity or quantity of the coregulator in a sample, wherein the "activity" may include the increase of the affinity of the nucleic acid binding factor for a cognate nucleic acid binding element, the facilitation of binding of the nucleic acid binding factor for a cognate nucleic acid binding element, the decrease of the affinity of the nucleic acid binding factor for a cognate nucleic acid binding element, or the abrogation of binding of the nucleic acid binding factor for a cognate nucleic acid binding element.

As used herein, the term "biosensor" or "biosensor assay" refers to any device or composition that is based upon biomolecules such as nucleic acids, polypeptides, carbohydrates, lipids, steroids or the like, which are used to detect, quantify, or determine the activity of nucleic acid binding elements or fragments thereof, nucleic acid binding factors or nucleic acid binding protein coregulators, including cellular events and post-translational modifications that effect the activity of nucleic acid binding factors.

Description of the Embodiments of the Invention

Novel biosensors and methods for the determination of the activity of nucleic acid binding factors and coregulators thereof are disclosed. The novel biosensors and methods herein described have distinct advantages and benefits over existing technology. Those benefits include among others high sensitivity, low signal to noise ratio, and multiple detection formats that enable practitioners of the invention to employ a customized detection formats that can be integrated into their current screening systems. Germane to the invention is the idea of preparing two nucleic acid molecules such that the sequence corresponding to a cognate protein-binding site is split between these two nucleic acid molecules. The two nucleic acid molecules (referred to herein as nucleic acid components) may also contain short complementary overhangs such that the nucleic acid components have some propensity to associate but this propensity is designed to be low so that in the absence of the protein very little association between the nucleic acid components occurs. The association between the two nucleic acid components re-creates the cognate binding site for the protein so that in the presence of the protein, the affinity of the protein to its cognate nucleic acid binding site will drive the association of the two nucleic acid components to completion. Detection of nucleic acid-protein complex formation is accomplished by labeling each of the two nucleic acid components with luminescent probes, fluorochromes, chemiluminescent substrates or colorimetric substrates. The physical proximity between the two nucleic acid fragments in a nucleic acid-protein complex provides the mechanism for a change in fluorescence signal or formation of a colorimetric/chemiluminescent product associated with nucleic acid-protein complex formation. Also, more than two nucleic acid components may be used in a single biosensor, especially when the invention is applied to the determination of the activity of DNA repair enzymes.

In another embodiment of the invention, one of the nucleic acid components may be attached to a solid substrate bead (microsphere) and the other nucleic acid component may be labeled with a detectable label, such as a luminescent or fluorescent probe. In the presence of a cognate nucleic acid binding factor, a nucleic acid-protein complex forms, such that the bead or microsphere is labeled with the detectable label. The labeled bead or microsphere may be detected using art recognized technology, such as fluorescence activated cell sorting or flow cytometric devices. This embodiment represents a coincidence-based luminescence signal detection method.

It should be apparent to the skilled artisan upon practicing the instant invention that the nucleic acid components, one or more of which may be attached to a detectable label, can be placed within prokaryotic or eukaryotic cells. Methods of transferring nucleic acids and other biomolecules into cells are well known in the art, including such methods as electroporation, cationic lipid based transfection, and the like. It is envisioned that cells may naturally express, or may be modified to express nucleic acid binding factors or coregulators thereof. Nucleic acid binding events may be assessed by measuring changes in cellular luminescence.

Any proximity-based or coincidence-based luminescence signal detection method such as FRET (Stryer, L. *Ann. Rev. Biochem.* 47, 819–846, 1978), fluorescence cross-correlation spectroscopy ("FCCS") (Maiti et al., *Proc. Nat'l Acad Sci USA* 94, 11753–11757, 1997), flow cytometry (Nolan and Sklar, *Nature Biotechnology* 16:633–638, 1998), scintillation proximity ("SPA") (Hart and Greenwald, *Molecular Immunology* 16:265–267, 1979; U.S. Pat. No. 4,658,649), luminescence resonance energy transfer (LRET) (Mathis, G. *Clin. Chem.* 41, 1391–1397, 1995), direct quenching (Tyagi et al., *Nature Biotechnology* 16, 49–53, 1998), ground-state complex formation (Packard, B. Z., Toptygin, D. D., Komoriya, A., and Brand, L. *Biophys. Chem.* 67, 167–176, 1997), chemiluminescence energy transfer (CRET) (Campbell, A. K., and Patel, A. *Biochem. J.* 216, 185–194, 1983), bioluminescence resonance energy transfer (BRET) (Xu, Y., Piston D. W., Johnson, *Proc. Natl. Acad. Sci.*, 96, 151–156, 1999), or excimer formation (Lakowicz, J. R. *Principles of Fluorescence Spectroscopy*, Kluwer Academic/Plenum Press, New York, 1999) is compatible with the design of the assay. Furthermore, it is envisioned that any chemiluminescent or colorimetric assay, such as, for example, the art recognized alkaline phosphatase-NBT/BCIP system, may be used in the present invention. The invention is applicable to any nucleic acid binding protein, since the invention is based on the general property of all such nucleic acid binding factors rather than on a feature specific to a given protein. The invention offers great flexibility of signal detection mode and nature of the fluorescence probe used. Multicolor detection is readily possible.

According to the invention described above, FCCS detection involves measuring the fluctuation of the fluorescence intensity signal in a sample containing the two nucleic acid components, wherein each nucleic acid component is labeled with a fluorochrome with a different emission wavelength. The association of the two fluorochrome-labeled nucleic acid components in the presence of a cognate nucleic acid binding factor protein may be measured by detecting the cross-correlation between each of the signals corresponding to the two fluorochromes. The use of FCCS for detection of association between two macromolecules labeled with two different fluorochromes is described in Rippe, K., "Simultaneous Binding of Two DNA duplexes to the NtrC-Enhancer complex Studied by Two-Color Fluorescence Cross-Correlation Spectroscopy," *Biochemistry* 39, 2131–2139, 2000, which is incorporated herein by reference.

According to the invention described above, flow cytometry may be used to detect the association of a luminescent or fluorescent-labeled nucleic acid component to a the "target" nucleic acid component, which is immobilized on a surface of microsphere. The use of flow cytometry in a similar situation is described in Nolan, J. P., and Sklar, L. A., "The emergence of flow cytometry for sensitive, real-time measurements of molecular interactions," *Nature Biotechnology* 16, 633–638, 1998, which is incorporated herein by reference. In one embodiment, one nucleic acid component is attached to a microsphere, wherein said nucleic acid component may or may not be labeled with one fluorochrome and wherein the microsphere is preferably several microns in diameter. The second nucleic acid component may be labeled with a fluorochrome, which is of a different color if the microsphere-attached nucleic acid component was also labeled. The association between the two nucleic acid components in the presence of a cognate nucleic acid binding factor may be measured using flow cytometry as a change in particle fluorescence or the ratio between fluorescence at two different colors if both nucleic acid components were labeled with fluorochromes.

According to the invention described above, a scintillation proximity assay ("SPA") may be employed to determine nucleic acid binding factor activity. In one embodiment, one nucleic acid component is attached to a microsphere that contains a solid scintillant and the other nucleic acid component is labeled with a radioisotope, preferably tritium. In the presence of the cognate nucleic acid binding factor, the radioisotope label is brought into close proximity of the microsphere containing the scintillant, thereby inducing the emission of light from the scintillant. The light may be detected by art recognized means of scintillation detection. The method of SPA is described in Hart and Greenwald, *Molecular Immunology* 16:265–267, 1979 and U.S. Pat. No. 4,658,649, which are both incorporated herein by reference.

In other embodiments, the invention provides means for rapidly determining the physical parameters of the nucleic acid-protein complex formation such as dissociation constants. The invention also provides a means for determining the affinity of a nucleic acid binding factor for variant nucleic acid binding elements. In this embodiment, nucleic acids comprising variant nucleic acid binding elements are combined with a nucleic acid binding factor and its cognate labeled nucleic acid components. Those variant nucleic acid binding elements that compete for the nucleic acid binding factor will affect the luminescence signal output compared to controls.

Furthermore, given that the nucleic acid binding activity of many proteins is regulated by other molecules or nucleic acid binding protein coregulators, such as cAMP or IP3, for example, the invention can detect these other molecules or nucleic acid binding protein coregulators. Likewise, the invention may also be used as a platform to identify novel agents, other nucleic acid binding protein coregulators and molecules, or drugs that mediate nucleic acid-protein interactions. The invention may further be used to identify proteins comprising an enhanceosome or supernumerary chromatin structure, wherein the proteins do not directly bind to DNA but rather bind directly or indirectly to other nucleic acid binding factors.

FIG. 1A illustrates the basic idea for detecting sequence-specific nucleic acid binding factors as described in this invention. In a preferred embodiment of the invention, two nucleic acid components are prepared wherein each component contains a portion of a nucleic acid sequence corresponding to a cognate binding site for a protein. The skilled artisan will recognize in the practice of the instant invention that there are several different possibilities of designing such nucleic acid components. In one aspect of the invention, the two nucleic acid components contain short complementary overhangs, which provide some affinity for the two components to anneal. In an alternative aspect of the invention, which is envisioned to be useful for proteins that can bind efficiently to a short DNA sequence, i.e., equal to or less than 10 base pairs (bp), the two nucleic acid components correspond to the two single-stranded components of the nucleic acid duplex. The length of the "single-stranded" overhang determines the propensity of the two nucleic acid components to associate in the absence of the cognate protein and is chosen such that at the concentrations of the nucleic acid components used in the assay the efficiency of spontaneous re-annealing is very low. Thus, in the absence of the cognate protein very little association between the two nucleic acid molecules occurs. In the presence of the cognate protein, the affinity of the protein for the nucleic acid drives the annealing of the two nucleic acid components and a specific nucleic acid-protein complex is formed. Re-annealing of nucleic acid components will bring the two labels or fluorochromes into close proximity and this protein-induced close proximity is utilized to generate a change in luminescence signal or production of a colored product, which thereby indicates the formation of a nucleic acid-protein complex.

The physical basis of the preferred embodiment of the invention is a fundamental relationship between the free energy ($\Delta G^0$) for the formation of nucleic acid-protein complex and the equilibrium binding constant (K) describing the amount of nucleic acid-protein complex formed at any given concentration of protein and nucleic acid:

$$\Delta G^0 = -RT\ln K \qquad (\text{eq.1})$$

If the free energy for binding of the protein to its cognate nucleic acid site is $\Delta G^0$, splitting the cognate binding site into two "half-sites" in two separate nucleic acid components, as illustrated in FIG. 1A, will result in the free energy of binding to a half-site being roughly ½ of $\Delta G$. Since the equilibrium constant (K) and free energy ($\Delta G^0$) are related by a logarithmic relationship (eq. 1), reducing the binding free energy by two-fold will result in a decrease in the binding constant by several orders of magnitude. Thus, under conditions where efficient binding of a protein to its cognate full-site occurs, no detectable binding of the protein to the half-site should occur. This large difference in the affinity of the protein to the full-site compared to the half-site is the driving force for the re-annealing of the two nucleic acid half-sites in the presence of the protein.

Whereas this invention is not bound by theoretical considerations, the following reaction scheme describes the behavior of the detection system depicted in FIG. 1:

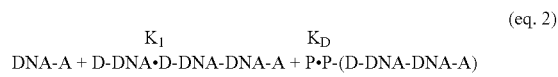

Figure 2:
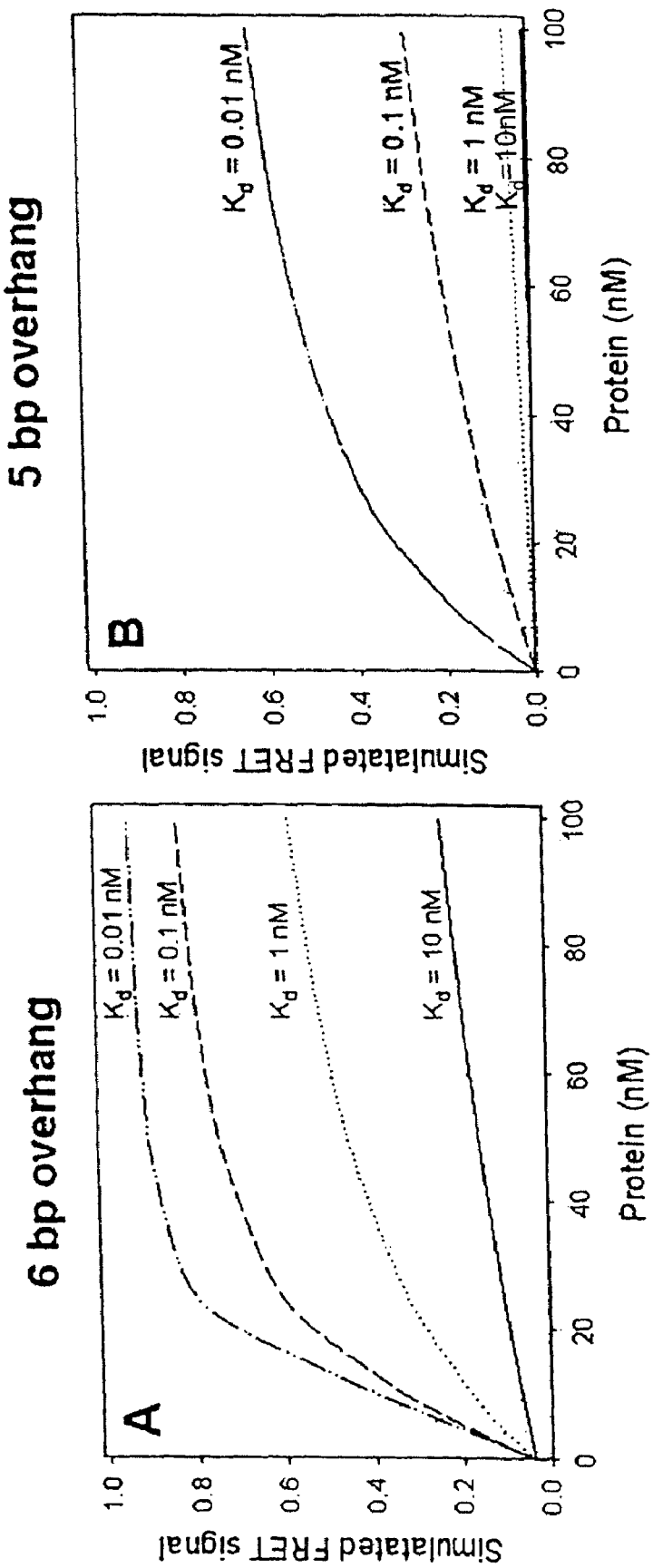
FIG. 2 shows theoretical simulations of the expected fluorescence signal change in the presence of nucleic acid binding factor for the design illustrated in FIG. 1. The results of calculations for two different lengths of complementary overhangs. 6 bp (panel A) and 5 bp (panel B), are shown in FIG. 2, where the length of the overhang affects the value of $K_d$.

(eq. 2)

where DNA-A is the acceptor-labeled DNA half-site, DNA-D is the donor-labeled DNA half-site, P is the nucleic acid binding factor, $K_1$ is the equilibrium constant for the annealing of DNA-A and D-DNA components, and $K_D$ is the equilibrium constant for binding of protein P to its cognate nucleic acid binding site. The results of the calculations for two different lengths of the complementary overhangs are shown in FIG. 2, wherein the length of the overhang determines the value of $K_1$. These simulations demonstrate the feasibility of the basic design of the invention described herein and depicted in FIG. 1, and that easily measurable changes in an observable signal, whether that change in signal is due to fluorescence energy transfer or production of a chemiluminescent or colored product, will be detected with a wide range of equilibrium constants typically observed for nucleic acid binding factors. Thus, the general applicability of this invention to any nucleic acid binding factor is a result of it being based on the general property of all nucleic acid binding factors, that general property being the high affinity for binding to a complete cognate binding site, and on the general thermodynamic logarithmic relationship between the free energy of the interaction and the equilibrium binding constant.

The present invention offers extensive flexibility in the use of a variety of luminescent or colorimetric probes, in the selection of sites for attachment of said probes within the nucleic acid molecules, and in the selection of a particular method of signal generation and detection. Commercially available reagents allow the incorporation of a variety of probes into the 5' end, 3' end or internal positions of the oligonucleotides during automated oligonucleotide synthesis. Thus probes may be incorporated during oligonucleotide synthesis or attached to the oligonucleotides via post-synthetic modification of oligonucleotides derivatized with reactive amino or thiol groups. The present invention does not impose any restrictions regarding the nature and the position of the probe so long as the probe does not interfere with the formation of protein-nucleic acid complex. Several alternative embodiments of labeled nucleic acid components are possible. For example, for some proteins it may not be possible to use the design in which the probes are located within the binding site for the protein and thus could potentially interfere with protein binding. In such a case, one alternative will be to use a design in which the probes are located outside the protein binding site.

In another embodiment, oligonucleotides can be labeled with essentially any amino-or thiol reactive luminescent probe of any emission spectra, and thus the color of the luminescence or fluorescence signal in the assay can be selected according to the specific needs of the application. As a result of this capability, it is possible to simultaneously detect two or more proteins within one assay kit using a mixture of nucleic acid components or constructs designed to recognize different proteins and labeled with luminescent probes exhibiting different emission spectra.

The sensitivity of the detection of nucleic acid binding factors using this invention is affected by at least two factors:

the sensitivity of luminescence signal detection and the affinity of the protein to its nucleic acid binding site. Detection sensitivity of the invention will not likely be limited by the sensitivity of signal detection since, especially in the case of fluorescence detection, commercial instrumentation can routinely detect fluorescence at picomolar fluorochrome concentrations. Also, recent advances in signal detection have resulted in sensitivities sufficient to detect single fluorochrome molecules. Hence, it is more likely that the sensitivity of detection will be determined by the affinity of the protein to its nucleic acid binding site. Therefore, the range of detection of nucleic acid binding factors will be in the range of the affinity of nucleic acid binding factors to their cognate nucleic acid binding sites, which is typically from low picomolar to high nanomolar protein concentrations.

The present invention also offers great flexibility in designing the nucleic acid molecules to be used in the detection assay. For example, the length of the nucleic acid molecules is not limited and additional elements may be incorporated into the nucleic acid molecules. In one embodiment, an alternate binding site for a second protein may be incorporated into one of the nucleic acid components, wherein the second protein cooperates in binding to the nucleic acid with the protein being assayed. The assay may then be performed in the presence of this second protein, or the assay may be performed in the presence and absence of this second protein to detect differences in the activity of the studied protein induced by the presence of the second protein.

In another embodiment, the nucleic acid components used in the assay are attached to a surface of a solid support. Methods for attaching nucleic acids to solid support are well known in the art and described in the literature (see Rogers, Y. H., et al., Anal. Biochem. 266, 23–30, 1999; Joos, B., et al., Anal. Biochem. 247, 96–101, 1997; Running J A, and Urdea M S, BioTechniques, 8:276277, 1990; which are herein incorporated by reference). Detection of the protein is thus accomplished by monitoring the signal emanating from the surface of solid support. Multiple DNA constructs designed to recognize different proteins may be attached to the solid surface resulting in an array capable of simultaneous detection of many nucleic acid binding factors. Solid supports may be membranes, such as nitrocellulose, PVDF or nylon, tips of light guides, optical fibers, conducting materials or biosensor devices, plastic tissue culture dishes, or multiwell plates.

In another embodiment, the nucleic acid components used in the assay may comprise a single nucleic acid molecule, wherein each nucleic acid component is separated by a length of nucleic acid which allows for bending of the entire nucleic acid such that the nucleic acid components may be brought into close proximity. Such a format may be used to detect or identify nucleic acid binding factors that are involved in higher order chromatin structure or enhanceosome structure, for example.

In another embodiment, the nucleic acid components used in the assay may be linked together via a flexible linker molecule. The linkage of the nucleic acid components will facilitate the interaction of the protein and the cognate nucleic acid binding site and allow for faster interaction kinetics. Preferred flexible linker molecules are polymers of spacer-18-phosphoramidate moieties, as herein described.

A particular strength of the present invention is that it is simple to operate, requiring only mixing of the assay solution, which comprises the nucleic acid components, with a test solution, which comprises a nucleic acid binding factor, nucleic acid binding protein coregulator or other protein component involved in chromatin or enhanceosome structure, followed by a short incubation and signal detection. The signal may be enhanced via methods known in the art, e.g., phosphorescence, scintillation or the like.

In another embodiment, the invention is directed to a method of diagnosing a disease in a patient or subject, wherein the disease is mediated by a nucleic acid binding factor or by a mutation in a cognate nucleic acid binding element. The patient or subject may be a human or other animal. The disease may be due to altered nucleic acid binding factors, such as, for example breast cancer, which results from alterations in the activity of the DNA repair enzymes BRCA1 or BRCA2. Other examples of diseases and their molecular bases are described in Table 1 (see Hoeijmakers, J. H. J., Nature 411:366–374, 2001, which is herein incorporated by reference). The diseases and syndromes presented in Table 1 represent a small subset of diseases which may be diagnosed using the present invention. The information presented in Table 1 is for exemplary purposes and therefore can not be construed as limiting.

TABLE 1

Diseases associated with nucleic acid binding factor abnormalities

| DISEASE OR SYNDROME | AFFECTED MOLECULAR MECHANISM |
|---|---|
| ataxia telangectasia (AT) | double-strand break repair |
| AT-like disorder | double-strand break repair |
| Bloom syndrome | homologous repair |
| breast cancer | homologous recombination |
| cancers recalcitrant to radiation therapy | p53 (transcription factor) |
| cockayne syndrome | transcription coupled repair (TCR) |
| hereditary nonpolyposis colorectal cancer | mismatch repair |
| Ligase IV deficiency | end joining |
| Nijmegen breakage disorder | double-strand break repair |
| Rothmund-Thomson syndrome | homologous repair |
| trichothiodystrophy | NER and TCR |
| Werner syndrome | homologous recombination/translesion repair |
| xeroderma pigmentosum | nucleotide excision repair (NER) |
| xeroderma pigmentosum variant | translesion synthesis |

Proteins or other nucleic acid binding protein coregulators may be extracted from a sample obtained from the patient using standard extraction protocols, which are well known in the art. Samples may be obtained from biopsied tissue, blood cells, skin cells, hair follicle cells, tissue plugs, epithelial cells obtained from the buccal cavity or other tissue sources. Samples may also include plant tissue, cultures of microorganisms or eukaryotic cells. The extracted samples are then mixed with the nucleic acid components of the invention, as herein described, and assayed for nucleic acid binding activity, facilitation of nucleic acid binding activity or abrogation of nucleic acid binding activity.

The invention may be used to identify agents, drugs, ligands, contaminants, pollutants or other nucleic acid binding protein coregulators which mediate the binding of abnormal nucleic acid binding factors to cognate nucleic acid elements, or conversely, to mediate the binding of normal nucleic acid binding factors to abnormal nucleic acid elements. In another embodiment, the invention is used to identify agents, drugs, ligands, contaminants, pollutants or other nucleic acid binding protein coregulators which disrupt the binding of abnormal nucleic acid binding factors to cognate nucleic acid elements, or conversely, to disrupt the binding of normal nucleic acid binding factors to abnormal nucleic acid elements. The term "abnormal" refers to aberrant or mutated forms of the nucleic acid or protein found within a patient, which is no longer able to bind to their respective partner in a physiologically normal manner.

In another embodiment, the invention is drawn to detecting, quantitating or determining the activity of nucleic acid binding factors or nucleic acid binding protein coregulators in a sample, wherein the first nucleic acid component is attached to a solid substrate and the second nucleic acid component is attached to a detectable label. Examples of solid substrates include tips of light guides, optical fibers, conducting materials or biosensor probes, glass plates, dishes, slides or beads; beads of any sort such as polystyrene, acrylamide, agarose or the like; membranes such as polyvinyldifluoride, nylon, nitrocellulose or the like; and tissue culture style plates, multiwell plates, or the like. The inventor envisions that the first nucleic acid component/solid substrate portion is mixed with the second nucleic acid component, which is attached to a detectable label, and either (1) a cognate nucleic acid binding factor and a sample comprising a nucleic acid binding protein coregulator, or (2) a sample comprising a nucleic acid binding factor. A positive interaction between the nucleic acid binding factor and the first and second nucleic acid components, which together comprise a nucleic acid binding element, results in the detectable label being attached to the solid substrate. A detectable signal on the solid substrate would be interpreted as indicating positive interaction between the nucleic acid binding factor and the nucleic acid binding element. According to this embodiment, the detectable signal may not necessarily involve a proximity-based detection assay such as FRET as described supra, but may also involve a single detectable label.

Biosensor for Nucleic Acid Binding Protein Coregulators

In addition to the proximity-based method of determining the activity of a nucleic acid binding protein coregulator as described herein above, the instant invention comprises a broader embodiment of a biosensor for nucleic acid binding coregulators or cellular events that affect nucleic acid binding factor activity, such as post-translational modifications and the effective enzymes. A biosensor for nucleic acid binding protein coregulators would utilize the "split" nucleic acid binding element-plus-nucleic acid binding factor technology as herein described above. However, the method of detecting said coregulators is not limited to proximity-based detection methods, but may also employ any and all molecular detection methods.

The "molecular detection methods" include, for example, fluorescence, fluorescence polarization, fluorescence quenching, radioactivity detection, radioscintigraphy, phosphorescence, electrochemical changes, redox potential changes, chemiluminescence, calorimetric substrate detection and other methods known in the art. Molecular detection methods are generally discussed in "Methods in Non-radioactive Detection in Biological System," by Gary C. Howard, Appleton & Lange, 1993, which is incorporated herein by reference. For example, a common application is where only one of the nucleic acid component is labeled, wherein the label can be any useful detectable marker such as, for example, a fluorescent molecule, radionuclide, any useful linker molecule (such as biotin, avidin, streptavidin, protein A, protein G, antibodies or fragments thereof, Grb2, polyhistidine, HRPO, $Ni^{2+}$, FLAG tags, myc tags), heavy metals, enzymes (examples include alkaline phosphatase, peroxidase and luciferase), electron donors/acceptors, acridinium esters, and calorimetric substrates. The skilled artisan would readily recognize useful detectable labels not mentioned above, which can be employed in the operation of the present invention.

While one nucleic acid component is attached to a detectable label, the other nucleic acid component may be fixed to a solid substrate, such as a bead, membrane, slide, plate, light guide, optical fiber, conducting material, biosensor chip, probe or the like. However, to successfully operate this invention, none of the nucleic acids needs to be attached to a solid substrate.

To determine the activity of a nucleic acid binding protein coregulator in a sample, the sample is mixed with one or more nucleic acid binding factors, a first nucleic acid component and a second nucleic acid component. The ability of the nucleic acid binding factor to bind to the cognate nucleic acid binding element should be mediated by the activity of a nucleic acid binding protein coregulator, wherein the term "mediated" is defined herein as the disruption of binding, either partial or full, or facilitation of binding, either partial or full, of a nucleic acid binding factor to a cognate nucleic acid element.

According to the scenario wherein the first nucleic acid component is attached to a solid substrate and the second nucleic acid component is attached to a detectable label, if the sample comprises a nucleic acid binding protein coregulator that directly or indirectly activates a nucleic acid binding factor, the activated nucleic acid binding factor will stabilize the interaction between each of the nucleic acid components. Accordingly, the labeled nucleic acid component becomes attached to the solid substrate and the detectable label becomes likewise attached to the solid substrate and may then be detected. The inventor also envisions that the nucleic acid binding factor may be fixed to a solid substrate and the first and second nucleic acids are not attached to a solid substrate. In that embodiment, one or both of the nucleic acid components may be attached to a detectable label.

In yet another embodiment, the first nucleic acid component or the nucleic acid binding factor is not attached to a solid substrate and the second nucleic acid component or the nucleic acid binding factor is attached with a detectable label (which, for the sake of argument in this illustration, may be a fluorochrome; see FIG. 1A, B or C). A positive interaction between an activated nucleic acid binding factor and a "complete" cognate nucleic acid binding element would result in a detectable event (such as a fluorescence polarization or quenching event in the scenario in which the detectable label is a fluorochrome).

As discussed above, many of the nucleic acid binding factors that play a central role in regulating cellular processes in both prokaryotes and eukaryotic cells possess ligand-dependent sequence-specific nucleic acid binding activity. (The term ligand-dependent is used interchangeably with the term coregulator-dependent; the term "ligand" as used herein is for all intents and purposes equivalent to the term "coregulator".) An important feature of these nucleic acid binding factors is that many of them have specifically evolved to regulate gene expression in response to specific chemicals present in their environment. An illustrative example of this ability is taught in a recent paper (Bresler et al., *Applied and Environ. Microbiol.* 66:904–908, 2000), which describes the development of a strain of bacteria, which was found in the soil surrounding plants that produce cocaine, that can metabolize cocaine. This strain appears to have developed a set of proteins that allow for the metabolism of cocaine, wherein the set of proteins may include ligand-dependent nucleic acid binding factors. Hence, any and all molecules, including toxins, drugs, alkaloids, pollutants and the like can function as coregulators of nucleic acid binding proteins, and thus are detectable using the instant biosensor.

The biosensors and methods of determining the activity of nucleic acid binding protein coregulators can be applied to the detection or quantification of coregulator molecules for which natural nucleic acid binding factors do not exist. Artificial or engineered factors can be made that recognize such coregulator molecules. The inventor envisions that nucleic acid binding factors can be engineered to be capable of being regulated by any chemical ligand of choice, i.e. nucleic acid binding factors can be created to respond to any and all chemicals for which a biosensor is desired. Thus, the invention is directed to biosensors and methods of detecting any and all chemical ligands for which there currently are no known naturally occurring receptors. The skilled artisan would expect that said embodiment can be successfully operated, given the high level of skill in the art. For example, engineered ligand-dependent nucleic acid binding factors can be generated by fusing modified ligand-binding domains to transcriptional activation domains. See Beerli et al., "Chemically regulated zinc finger transcription factors," *J. Biol. Chem.* 275:32617–32627 (2000) and references cited therein, which are incorporated herein by reference. Engineered ligand-dependent nucleic acid binding factors can also be generated by employing in vitro enzyme evolution methods followed by screening for specific ligand binding activity. See Cohen et al., "In vitro enzyme evolution: the screening challenge of isolating the one in a million," *TRENDS in Biotechnology*, 19:507–512 (2001) and references cited therein, which are incorporated herein by reference. Additionally, since bacteria exhibit the remarkable ability to adapt to the environment and to deal with new chemicals present in their environment, engineered ligand-dependent nucleic acid binding factors can also be generated by selecting for bacteria that are resistant to ligands of interest. Ligand-specific ligand-dependent nucleic acid binding factors and cognate nucleic acid elements could then be isolated from those ligand-resistant strains of bacteria and used in ligand-specific biosensors. See Bresler et al., *Applied and Environ. Microbiol.* 66:904–908 (2000), which is incorporated herein by reference, and which describes the isolation of cocaine-resistant bacteria that produce receptors for cocaine that are likely to be nucleic acid binding factors. The "ligands" discussed herein are for the purposes of this invention equivalent to "coregulators" of nucleic acid binding proteins.

Preferred methods of operating the instant nucleic acid binding factor-based biosensor to detect nucleic acid binding protein coregulators are detailed in Examples 9 and 10, which demonstrate the use of a proximity-based fluorescence assay, wherein both nucleic acid components are attached to fluorescent labels, a fluorescence polarization assay, wherein only one nucleic acid component is attached with a fluorochrome, and a calorimetric assay, wherein the first nucleic acid component is attached to a solid substrate and the second nucleic acid component is attached to a useful linker molecule.

The above disclosure describes several preferred embodiments of the invention, which do not limit the scope of the invention. The skilled artisan in the practice of this invention will recognize other embodiments of this invention that are not overtly disclosed herein. The invention is further illustrated by the examples described below. These examples are meant to illustrate the invention and are not to be interpreted as limiting the scope of the invention.

EXAMPLE 1

Detection of cAMP Receptor Protein (CAP), a Sequence-specific Nucleic Acid Binding Protein From *E. coli*.

Figure 3:
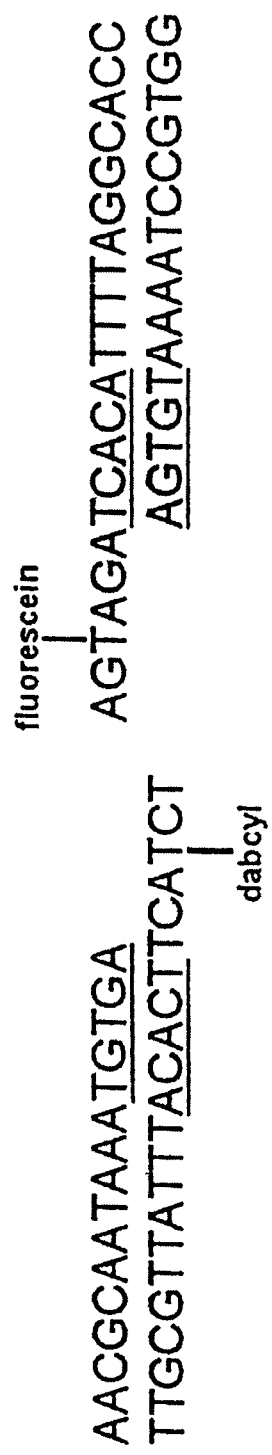
FIG. 3 depicts the fluorochrome-labeled oligonucleotides used for the detection of CAP protein. The first nucleic acid component (left) comprises SEQ ID NO:1 (top) and SEQ ID NO:4 (bottom). The second nucleic acid component (right) comprises SEQ ID NO:2 (top) and SEQ ID NO:3 (bottom).
Figure 3:
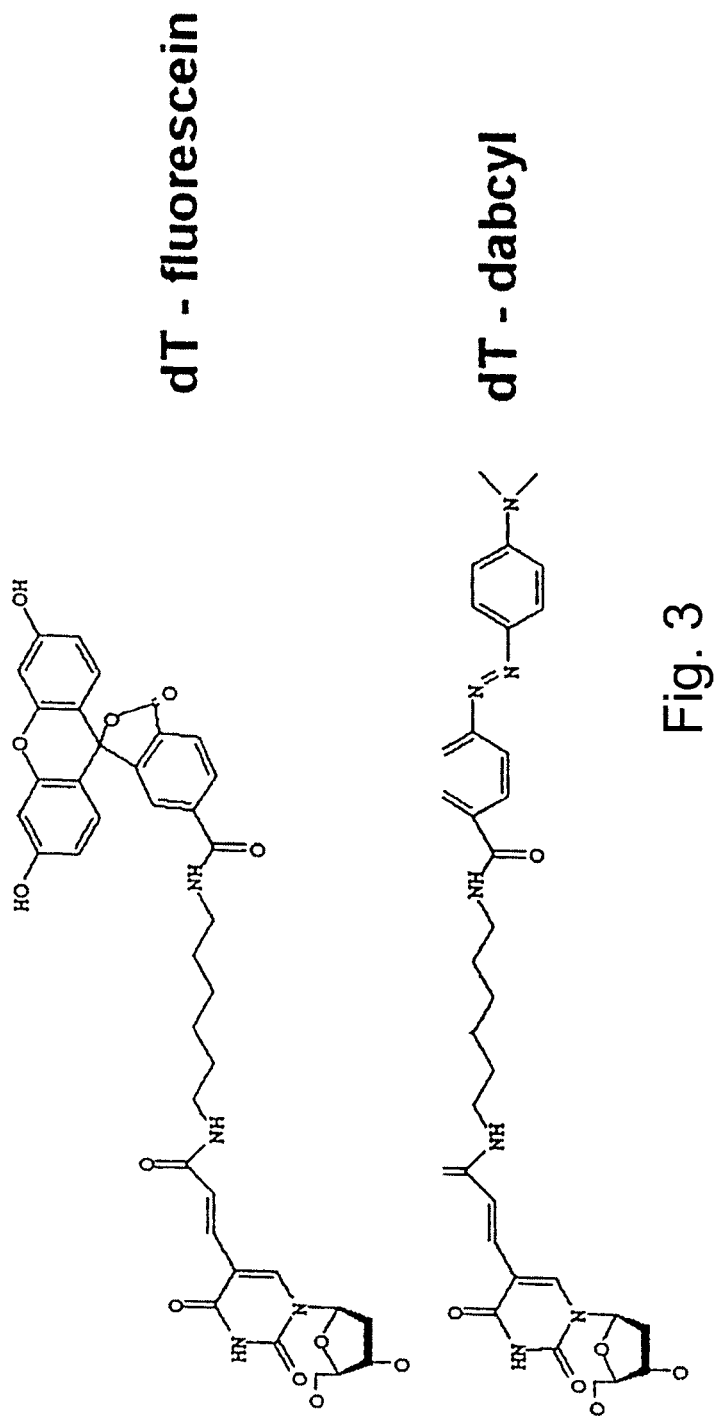

CAP is a bacterial transcription activator which binds DNA at a $K_d$=~0.1 nM in a sequence specific manner (Busby, S., and Ebright, R. H. *J. Mol. Biol.* 293, 199–213, 1999). A 38 bp DNA sequence corresponding to a consensus CAP site (Ebright, R. H., Ebright, Y. W. & Gunasakera, A. *Nucleic Acids Res.* 17, 10295–10305, 1989) was used as a basis for designing oligonucleotides necessary for preparing the CAP assay reagents according to the scheme illustrated in FIG. 1A. FIG. 3 illustrates the details of the design used. The following four oligonucleotides were synthesized using standard phosphoramidate automated oligonucleotide synthesis (F=dT-fluorescein; D=dT-dabcyl):

| | |
|---|---|
| 5'-AACGCAATAAATGTGA | (CAP1; SEQ ID NO:1) |
| 5'-AGFAGATCACATTTTAGGCACC 3' | (CAP2; SEQ ID NO:2) |
| 5'-GGTGCCTAAAATGTGA | (CAP3; SEQ ID NO:3) |
| 5'-TCDACTTCACATTTATTGCGTT | (CAP4; SEQ ID NO:4) |

The fluorescence donor (fluorescein) and the fluorescence acceptor (dabcyl) were introduced into DNA fragments using commercially available dT-fluorescein and dT-dabcyl (Glen Research, Sterling, Va.), wherein dT stands for deoxythymidine. The oligonucleotides were purified using reverse phase chromatography on a RPC column (Pharmacia) as previously described (Heyduk, E., and Heyduk, T. *Anal. Biochem.* 248, 216–227, 1997). The fractions containing the oligonucleotides were dried in a vacuum centrifuge concentrator and subsequently dissolved in 50 µl of water. The concentration of the stock solutions of oligonucleotides was determined by recording the UV-VIS absorption spectrum of a small aliquot of the stock solution diluted to 400 µl. The CAP1 oligonucleotide (SEQ ID NO:1) was hybridized with CAP4 oligonucleotide (SEQ ID NO:4) to generate the CAP1/CAP4 duplex and CAP2 oligonucleotide (SEQ ID NO:2) was hybridized with CAP3 oligonucleotide (SEQ ID NO:3) to generate the CAP2/CAP3 duplex. For the hybridization appropriate oligonucleotides were mixed at 10 µM concentration in 100 µl of 50-mM Tris/HCl (pH 8.0), 100 mM NaCl, 1 mM EDTA, heated for 1 min at 95° C. and then cooled to 25° C. for 1 hr. All subsequent fluorescence measurements were performed at 25° C. in 50-mM Tris/HCl (pH 8.0), 100 mM NaCl (or 50 mM NaCl where indicated), 1 mM EDTA, 0.1 mg/ml BSA, and 200 µM cAMP in 200 µl quartz cuvette using Aminco-Bowman Series 2 spectrofluorometer. The excitation wavelength was at 490 nm and the emission was recorded from 500 to 650 nm.

Figure 4:
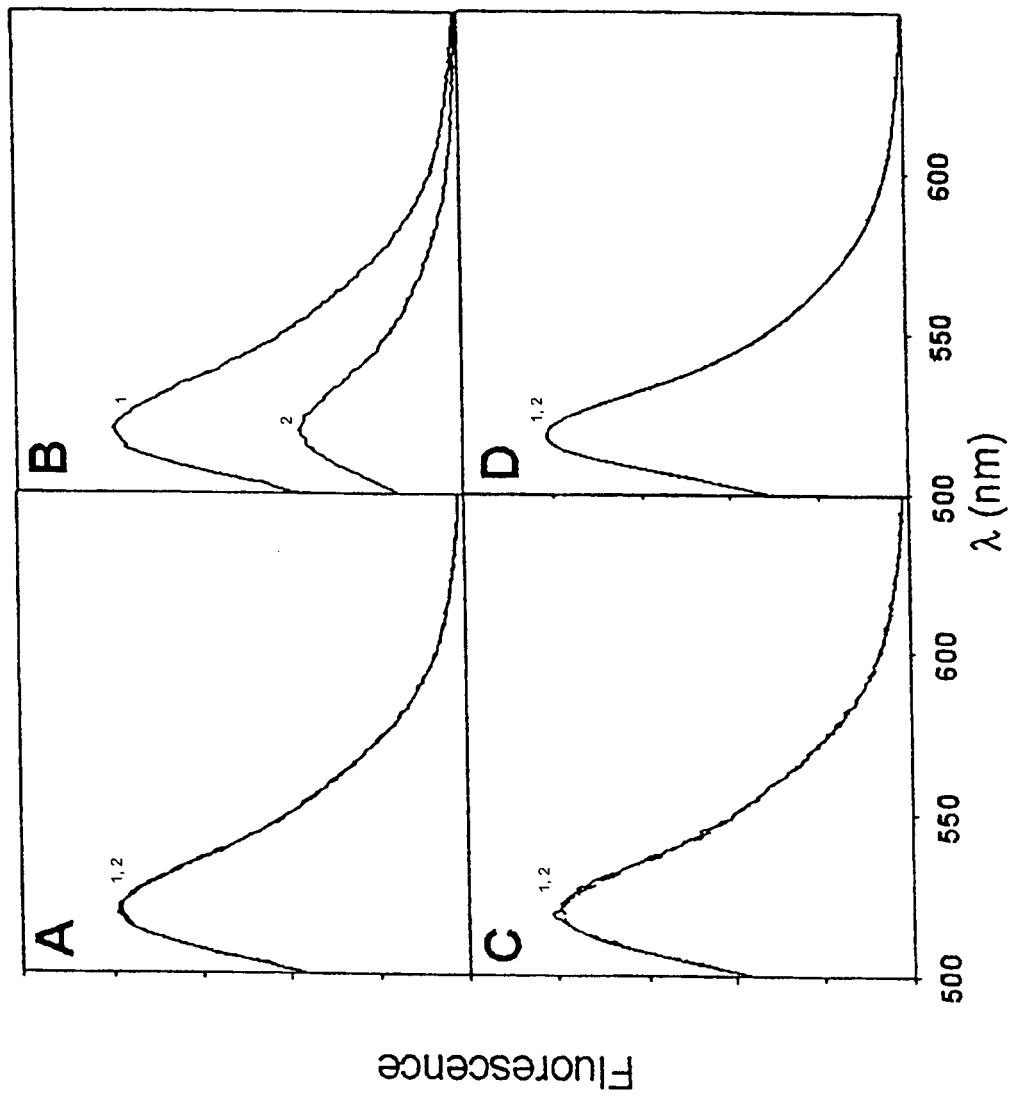
FIG. 4 shows fluorescence spectra of nucleic acid molecules shown in FIG. 3 in the presence of CAP and cAMP (panel B, curve 2), in the absence of CAP (panel A), in the presence of CAP without cAMP (panel C) and in the presence of Trp repressor protein (panel D).

FIG. 4A shows the spectrum of 50 nM of the CAP2/CAP3 duplex (curve 1) and the spectrum of 50 nM of the CAP2/CAP3 duplex in the presence of 50 nM CAP1/CAP4 duplex (curve 2). No significant change of the fluorescence of the CAP2/CAP3 duplex in the presence of the CAP1/CAP4 duplex was observed, indicating that in the absence of CAP protein there is very little association between the CAP2/CAP3 and CAP1/CAP4 duplexes. FIG. 4B illustrates changes in fluorescence observed upon the addition of CAP protein. The spectrum of 50 nM of the CAP1/CAP4 duplex and 50 nM of the CAP2/CAP3 duplex was recorded (curve 1). CAP protein was added at 75 nM and after 15 minutes of incubation the spectrum was recorded (curve 2). A major quenching of fluorescence of approximately 50% of the control signal intensity was observed, which is consistent with the prediction that in the presence of CAP protein the association between the CAP1/CAP4 and CAP2/CAP3 duplexes is facilitated and that the fluorescein (fluorescent donor) present in the CAP2/CAP3 duplex is brought into close proximity to the dabcyl (fluorescent acceptor) present in the CAP1/CAP4 duplex, which results in the quenching of fluorescence emission due to FRET between the fluorescein and dabcyl.

To test the specificity of the fluorescence quenching observed, the experiment illustrated in FIG. 4B was repeated in the absence of cAMP. Sequence-specific binding of CAP requires the presence of cAMP and in the absence of cAMP only non-specific low affinity nucleic acid binding is observed. No change in fluorescence upon addition of CAP in the absence of cAMP was observed (FIG. 4C), further demonstrating the specificity of the assay. Also, no change in fluorescence was observed when an unrelated nucleic acid binding protein, i.e., Trp repressor ("TrpR"), was added at high concentration (400 nM) (FIG. 4D).

Figure 5:
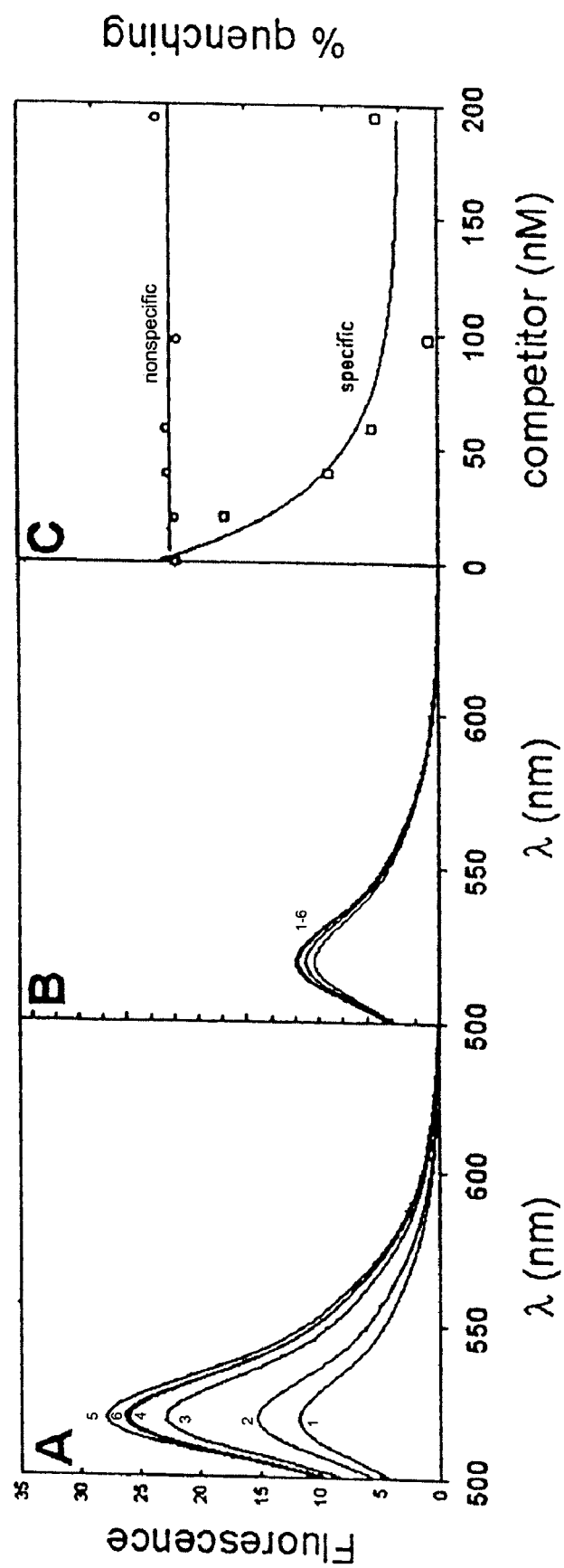
FIG. 5 depicts control experiments in which an unlabeled DNA fragment containing the CAP binding site blocks the change in fluorescence signal observed in the presence of CAP (panel A), whereas a nonspecific DNA fragment does not affect a change in fluorescence signal (panel B). Panel C plots the fluorescence quenching observed under each condition.

FIG. 5 illustrates the experiments in which the effect of the addition of unlabeled DNA duplex on the assay was tested. Two 30 bp unlabeled DNA duplexes were prepared using the following oligonucleotides:

```
                                    (SP1; SEQ ID NO:5)
5'-CCTAAAATGTGATCTAGATCACATTTATTG-3'

(NSP1; SEQ ID NO:6)
5'-GCATCGGTCACTGCAGTCTCGACAGCTACG-3'
```

To prepare 30 bp duplexes, SP1 and NSP1 oligonucleotides were hybridized with their respective complementary single-stranded oligonucleotides as described above for the CAP oligonucleotides. The SP1 DNA (SEQ ID NO:5) contains the consensus binding site for the CAP protein whereas the NSP1 DNA (SEQ ID NO:6) represents a random DNA sequence. First, the spectrum of 50 nM CAP2/CAP3 and 50 nM CAP2/CAP3 in the presence of 50 nM CAP in 50 mM Tris/HCl (pH 8.0), 50 mM NaCl, 1 mM EDTA, 0.1 mg/ml BSA, and 200 µM cAMP was recorded (curve 1, FIG. 5A and 5B). The measurements were then repeated in the presence of increasing concentrations of either the SP1 duplex (FIG. 5A) or the NSP1 duplex (FIG. 5B). The following concentrations of the respective duplexes were used: 19. 6 nM (curve 2), 39.1 nM (curve 3), 58.7 nM (curve 4), 97.6 nM (curve 5), and 194.2 nM (curve 6). The fluorescence quenching observed at each of these conditions is plotted in FIG. 5C. The DNA duplex containing the CAP binding site was able to efficiently block detection of CPA protein whereas the duplex containing the random sequence had no effect on CAP detection. Thus, the results shown in FIG. 5 provide additional evidence for the specificity of detection of CAP and also show that such competition assays may be used in the assessment of the relative binding affinities of proteins to various nucleic acid molecules.

Figure 6:
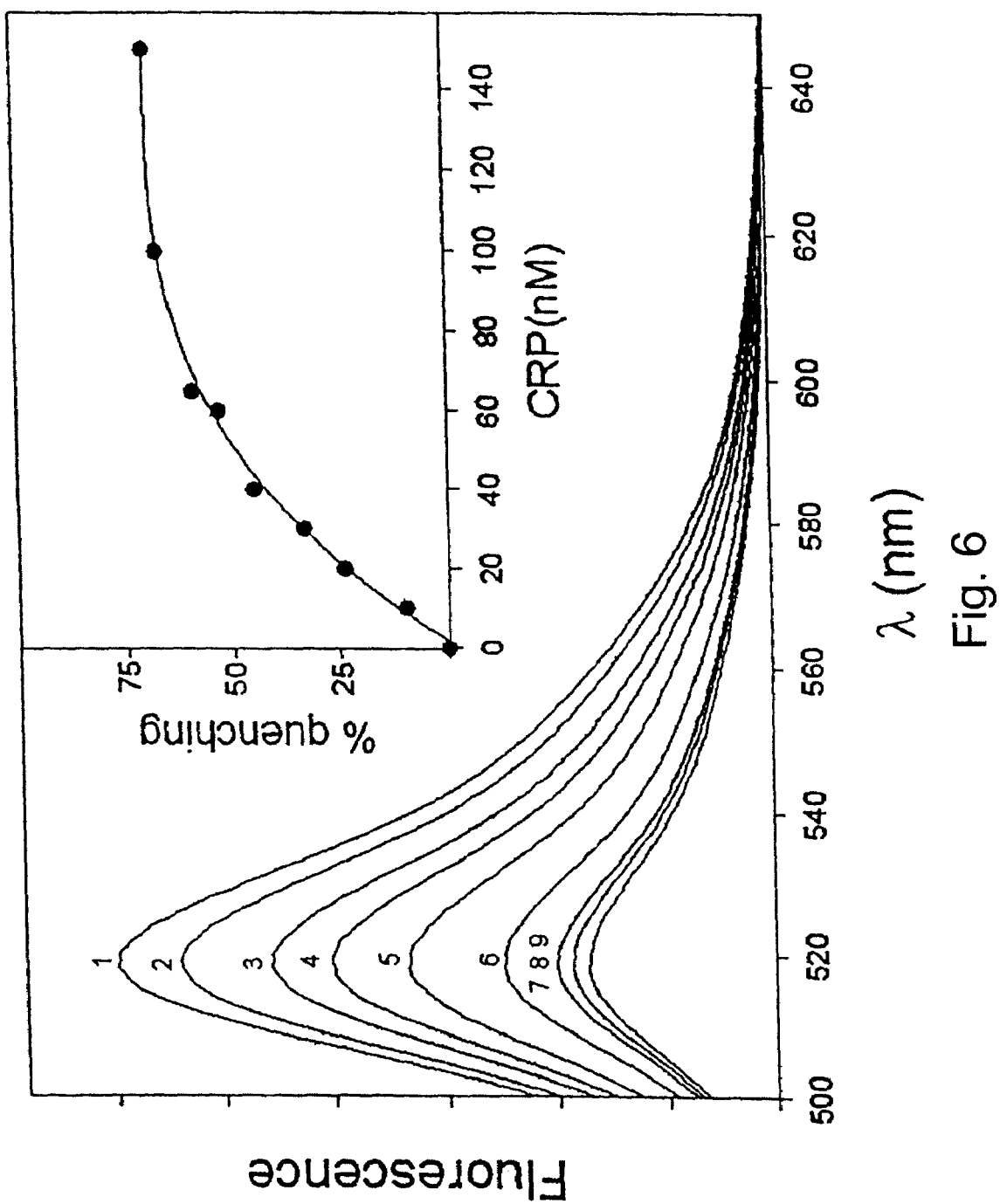
FIG. 6 depicts the dependence of the degree of change in fluorescence signal on the concentration of CAP protein.

FIG. 6 illustrates the change in fluorescence observed upon addition of increasing amounts of CAP protein in the assay. The experiments were performed under the same conditions as those for the experiment described above and in FIG. 4. Fluorescence quenching increased proportionally with the increase of CAP concentration until a saturation of the signal occurred at ~150 nM protein. This result suggests that the assay may be used for the determination of nucleic acid binding protein concentrations in samples.

Figure 7:
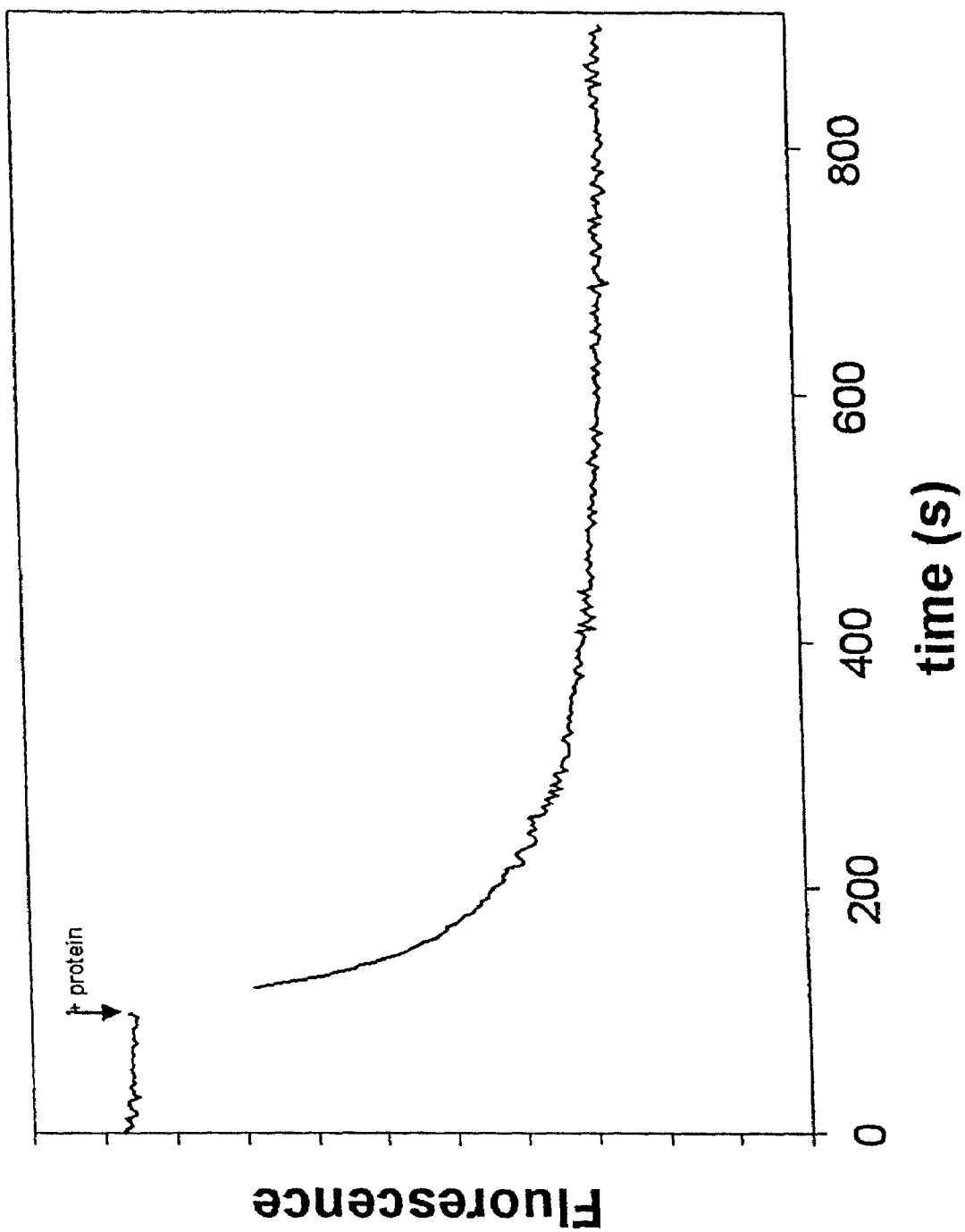
FIG. 7 shows the time dependence of fluorescence signal change in the presence of CAP.

The kinetics of CAP induced fluorescence quenching was also studied to determine the time required for completion of the assay (FIG. 7). In this experiment the fluorescence intensity of 50 nM CAP2/CAP3 and 50 nM CAP2/CAP3 was monitored as a function of time at 520 nm with the excitation wavelength set at 490 nm. At the time indicated by the arrow in FIG. 7, 100 nM CAP protein was added and monitoring of the fluorescence signal was resumed. According to the data, the reaction goes to completion in approximately 15 minutes suggesting that a 15–30 minute incubation time is sufficient for completion of this assay.

EXAMPLE 2

Demonstration of the Use of Fluorochromes with Different Emission Spectra and Different Modes of Fluorescence Signal Detection.

The following oligonucleotides, which have identical sequences to CAP2 and CAP4, respectively, were synthesized using standard phosphoramidate automated oligonucleotide synthesis, wherein X represents amino-dT:

```
5'-AGXAGATCACATTTTAGGCACC-3'    (CAP5; SEQ ID NO:7)

5'-TCXACTTCACATTTATTGCGTT-3'    (CAP6; SEQ ID NO:8)
```

Amino-Modifier C2 dT (Glen Research, Sterling, Va.) was incorporated into positions that are equivalent to the positions at which fluorescein-dT and dabcyl-dT has been used previously in CAP2 and CAP4 oligonucleotides, respectively. Amino-Modifier C2 dT contains a reactive aliphatic amino group that can be used to covalently attach any amino-reactive fluorescence probe. CAP5 (SEQ ID NO:7) and CAP6 (SEQ ID NO:8) oligonucleotides were modified with 7-diethylaminocoumarin-3-carboxylic acid, succinimidyl ester. This fluorochrome is excited at 433 nm and the maximum emission occurs at 475 nm providing the possibility of testing the assay with different emission colors. To modify the fluorochrome, ~20 nmoles of the oligonucleotides were dissolved in 50 µl of 50 mM NaHCO$_3$ (pH 8.3) and 50 nmoles of dry 7-diethylaminocoumarin-3-carboxylic acid, succinimidyl ester (Molecular Probes, Eugene, Oreg.) were added. The reaction mixture was incubated overnight at room temperature. The excess uncoupled dye was removed on a G-25 spin column (Amersham Pharmacia Biotech, Piscataway, N.J.) and the labeled oligonucleotides were further purified by reverse phase chromatography as previously described. The fractions containing the fluorochrome-labeled oligonucleotides were dried in Vacuum centrifuge concentrator and were dissolved in 50 µl of water. The concentrations of the stock solutions of the oligonucleotides were determined by recording the UV-VIS absorption spectrum of a small aliquot of the stock solution diluted to 400 µl. The 7-diethylaminocoumarin-3-carboxylic acid labeled CAP5 oligonucleotide was hybridized with CAP3 oligonucleotide to generate the CAP5/CAP3 duplex. The 7-diethylaminocoumarin-3-carboxylic acid labeled CAP6 oligonucleotide was hybridized with CAP1 oligonucleotide to generate the CAP6/CAP1 duplex. For the hybridization, the appropriate oligonucleotides were mixed at 10 µM concentration in 100 µl of 50 mM Tris/HCl (pH 8.0), 100 mM NaCl, 1 mM EDTA, heated for 1 min at 95° C. and then cooled to 25° C. for 1 hr.

Figure 8:
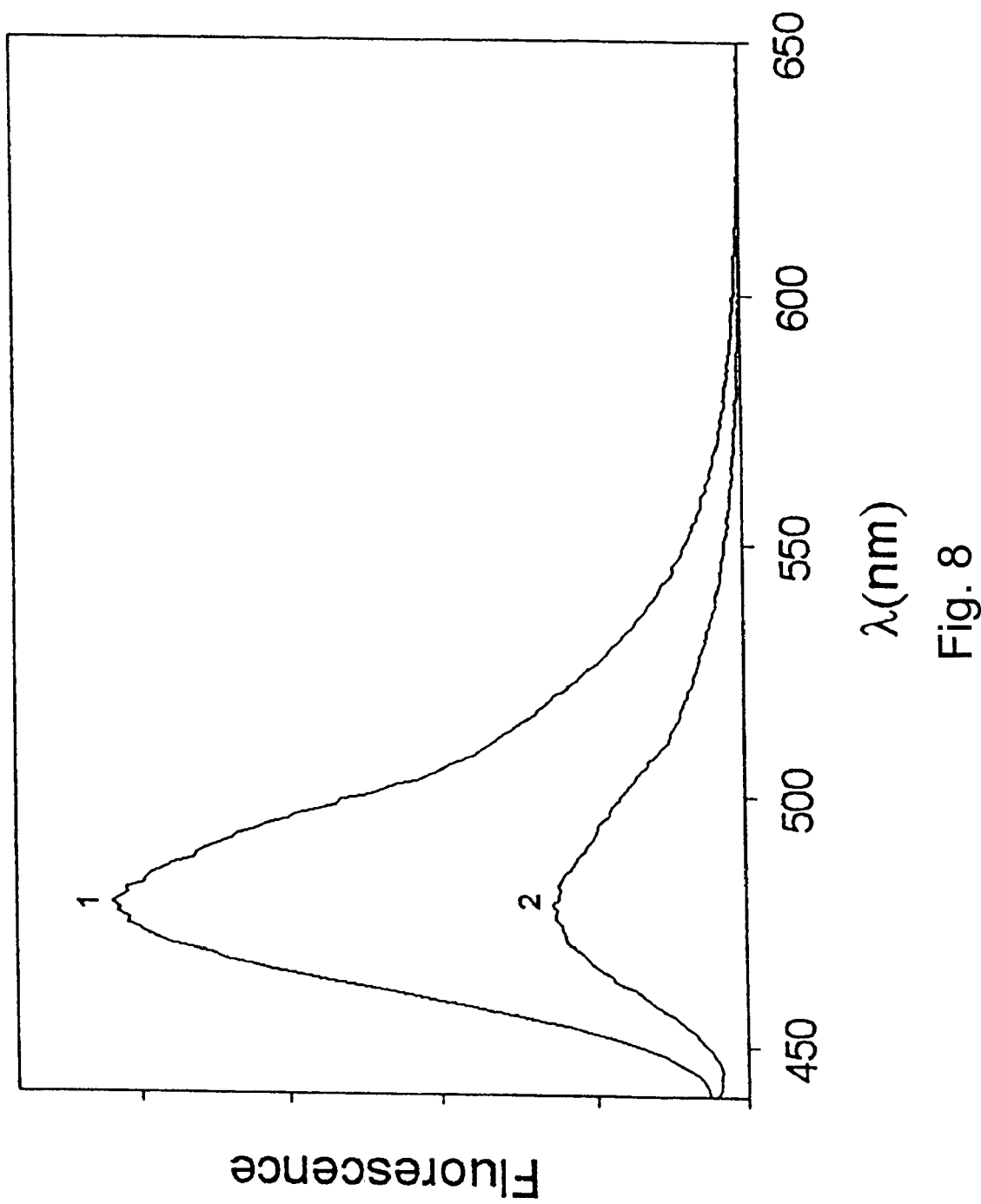
FIG. 8 illustrates the use of 7-diethylaminocoumarin-3-carboxylic acid for the detection of CAP protein. Curve 1 represents no CAP present. Curve 2 represents the presence of 100 nM CAP.

In the first experiment (FIG. 8), the pair of CAP5/CAP3 and CAP4/CAP1 nucleic acid duplexes were tested in the CAP assay. In this format, the 7-diethylaminocoumarin-3-carboxylic acid label present in the CAP5/CAP3 duplex functions as the fluorescence donor and the dabcyl label present in the CAP4/CAP1 duplex functions as a fluorescence acceptor. The experiment was performed at 25° C. in 50 mM Tris/HCl (pH 8.0), 100 mM NaCl, 1 mM EDTA, 0.1 mg/ml BSA, and 200 µM cAMP. Curve 1 of FIG. 8 shows the fluorescence spectrum of a 50 nM solution of CAP5/CAP3 plus CAP4/CAP1 in the absence of CAP protein. Addition of 100 nM of CAP resulted in the dramatic quenching (~70%) of the fluorescence signal as expected (FIG. 8, curve 2).

Figure 9:
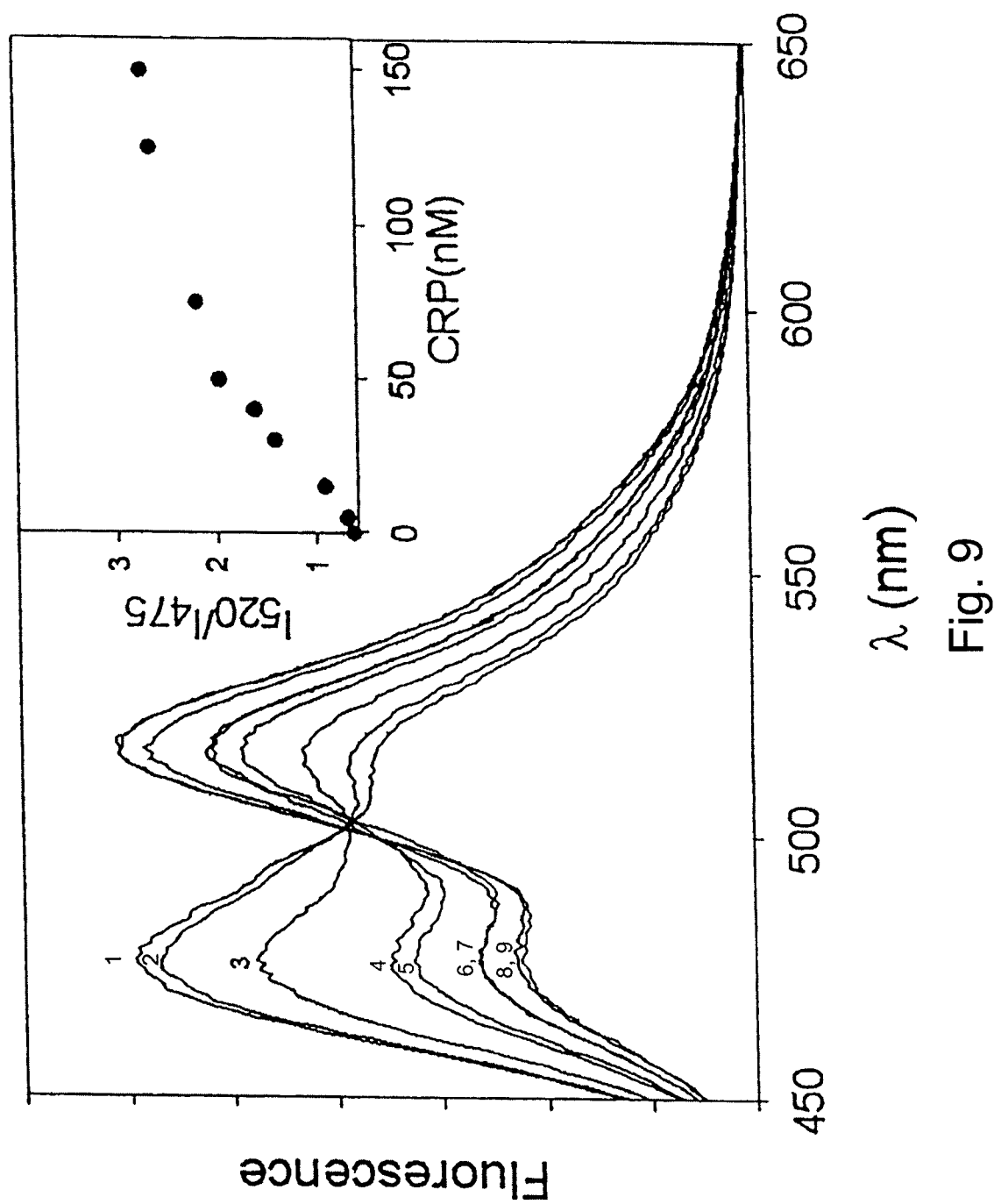
FIG. 9 depicts the use of the ratio of fluorescence at different wavelengths for the detection of CAP protein. Curves 1–9 represent increasing amounts of CAP, from 0 to 150 nM, respectively.

In a second experiment (FIG. 9), the pair of CAP6/CAP1 and CAP2/CAP3 nucleic acid duplexes were tested for the performance in CAP assay. In this assay format, the 7-diethylaminocoumarin-3-carboxylic acid present in the CAP6/CAP1 duplex functioned as a fluorescence donor and the fluorescein present in the CAP2/CAP3 duplex functioned as an acceptor. In this case, both the donor as well as the acceptor are fluorescent. The experiment was performed at 25° C. in 50 mM Tris/HCl (pH 8.0), 100 mM NaCl, 1 mM EDTA, 0.1 mg/ml BSA, and 200 µM cAMP. Curve 1 of FIG. 9 shows the fluorescence spectrum of 50 nM solution of CAP6/CAP1 plus CAP2/CAP3. The excitation wavelength was at 433 nm, therefore the major emission peak was observed at 475 nm, which is the emission maximum for 7-diethylaminocoumarin-3-carboxylic acid. The shoulder observed at about 520 nm is due to the residual emission of fluorescein, which is also to a small extent excited at 433 nm. Upon addition of varying amounts of CAP in a range from 0 to 150 nM (curves 2–9), a pronounced quenching of the peak at 475 nm and a pronounced enhancement of the peak at 520 nm is observed. Recall that the emission maximum of fluorescein is 520 nm. This data shows that the detection of the CAP protein, or any cognate nucleic acid binding protein, may be accomplished either by quenching of fluorescence at 475 nm or by enhancement of fluorescence at 520 nm. Also, as shown in the inset of FIG. 9, the ratio between the fluorescence intensities at 520 nm and 475 nm may be used to determine the concentration of nucleic acid binding proteins. This ratiometric mode of signal detection could be particularly useful since it would be less prone to trivial errors (such as pipeting errors, general quenching by some unrelated compounds present in the assayed sample). Taken together, the data presented in this example show that the assay method described in this invention provides a great flexibility in terms of the nature of the fluorescent probe used, the emission spectrum of the probe, and the mode of fluorescence signal detection.

EXAMPLE 3

The Detection of Nucleic Acid Binding Protein Coregulators, for Example cAMP

The activity of many nucleic acid binding proteins is regulated by small molecules, other proteins or cellular events (e.g., phosphorylation). Hence, the present invention may be used to identify or detect these regulatory molecules or regulatory cellular events.

CAP protein binds both cAMP and cGMP with micromolar affinity (Takahashi, M., Blazy, B., and Baudras, A. *Biochemistry* 19, 5124–30). Thus, CAP protein, by itself, is a poor reagent for specifically detecting cAMP. However, the high affinity of CAP for its cognate nucleic acid binding sequence is selectively dependent on cAMP, but not cGMP. Since only cAMP is thermodynamically linked to sequence-specific nucleic acid binding, in the presence of DNA containing a CAP binding site, the affinity of CAP for cAMP is increased about 1000-fold, whereas the affinity for cGMP remains unchanged. Thus, in the presence of DNA containing a CAP binding site, CAP becomes a sensitive and selective sensor of cAMP.

Figure 10:
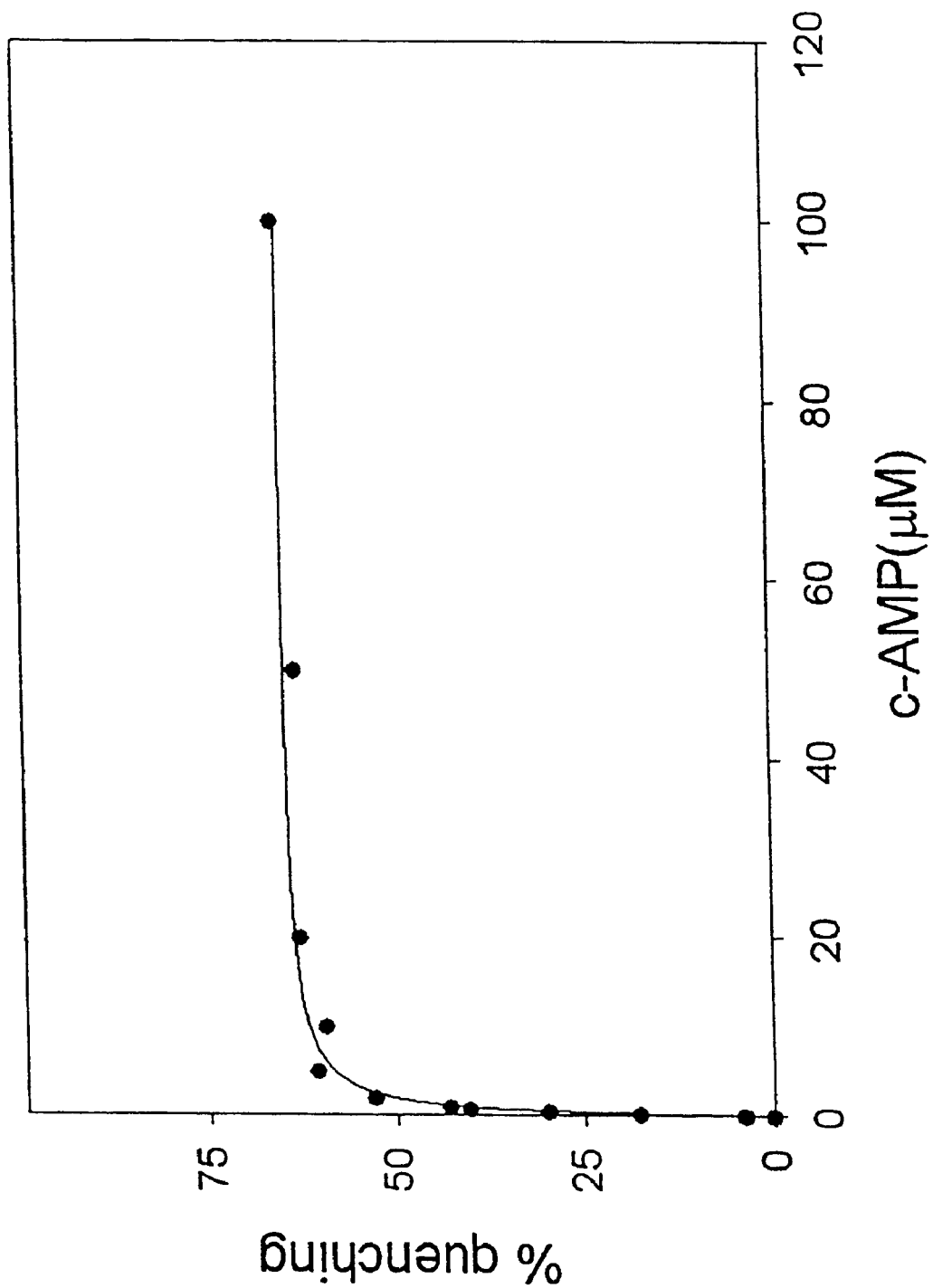
FIG. 10 depicts the effect of the nucleic acid binding factor coregulator cAMP upon CAP binding to the CAP1/CAP4 and CAP2/CAP3 DNA duplex. No detectable binding occurs in the absence of cAMP.

As already demonstrated in FIG. 4C, in the absence of cAMP, CAP protein does not produce a change in fluorescence signal intensity. To demonstrate the detection of cAMP using CAP the assay, the fluorescence intensity of 50 nM solution of CAP1/CAP4 plus CAP2/CAP3 in 50 mM Tris/HCl (pH 8.0), 50 mM NaCl, 1 mM EDTA, 0.1 mg/ml BSA containing 75 nM CAP was measured at different concentrations of cAMP ranging form 0 to 100 mM. FIG. 10 shows that, as expected, a fluorescence quenching proportional to the concentration of cAMP was observed with a saturation of the signal occurring a approximately 5 µM cAMP. Thus, the present invention may be used as a sensitive detector for cAMP or any other agent or event that potentiates nucleic acid binding.

The flexibility of the assay design, which is a particular strength of the present invention, allows for the optimization of the assay in terms of sensitivity, color of fluorescence emission, and/or mode of fluorescence signal detection. While this example illustrates the use of the invention to detect cAMP, it is envisioned that the invention is not limited to cAMP detection. Any molecule, whose presence could be linked to changes in the affinity for DNA by a nucleic acid binding protein, may be detected using this invention. More generally, any process which affects the affinity of a nucleic acid binding protein to a DNA may also be assayed using this invention.

EXAMPLE 4

Assay Variant With the DNA Linked by a Long Flexible Linker.

Figure 11:
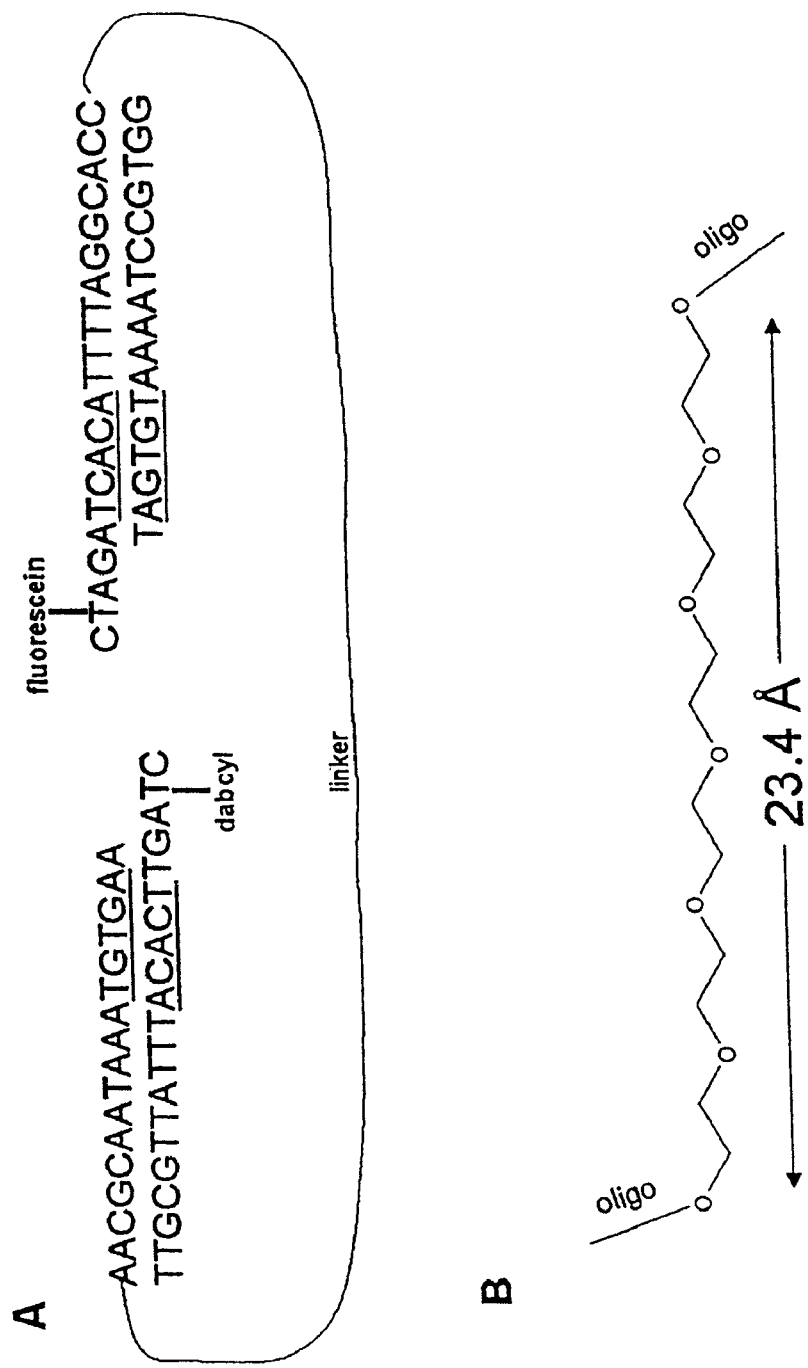
FIG. 11 illustrates the design of an assay in which the two nucleic acid components are covalently linked by a long flexible linker to remove dependency of the assay on DNA concentration and to reduce the time necessary to perform the assay. Panel A depicts the two linked nucleic acid components: the sequence containing the linker corresponds to SEQ ID NO:9, and the complementary, unlinked sequences correspond to SEQ ID NO:10 (right) and SEQ ID NO:11 (left). Panel B depicts one unit of a spacer-18-phosphoramidate moiety.

The properties of the assay illustrated in FIG. 1 depend upon the total concentration of the nucleic acid components. By covalently linking the two DNA duplexes—i.e., the components of the assay—by a long flexible linker, the assay becomes independent of DNA concentration, within a range of detectability of fluorescence signal and within a range of concentration required for efficient protein binding. FIG. 11 illustrates the design this variant of the assay for CAP detection. The nucleic acid components of the assay were covalently linked during oligonucleotide synthesis by introducing 12 moieties of the Spacer 18 phosphoramidate (Glen Research, Sterling, Va.), the structure of which is shown in FIG. 11B. The addition of 12 units of Spacer 18 results in a distance of ~270 Å between the linked oligonucleotides. The following oligonucleotides were prepared (F=dT-fluorescein, D =dT-dabcyl, X=Spacer 18):

```
CFA GAT CAC ATT TTA GGC ACC XXX XXX XXX XXX AAC GCA ATA AAT GTG AT   (CAP7; SEQ ID NO:9)

CDA GAT CAC ATT TAT TGC GTT                                          (CAP8; SEQ ID NO:10)

GGT GCC TAA AAT GTG AT                                               (CAP9; SEQ ID NO:11)
```

The oligonucleotides were purified using reverse phase chromatography on a RPC column (Amersham Pharmacia Biotech, Piscataway, N.J.) as previously described (Heyduk, E., and Heyduk, T. Anal. Biochem. 248, 216–227, 1997). The fractions containing the oligonucleotides were dried in a Vacuum centrifuge concentrator and then dissolved in 50 µl of water. The concentration of the stock solutions of oligonucleotides was determined by recording the UV-VIS absorption spectrum of a small aliquot of the stock solution diluted to 400 µl. To generate the CAP7/CAP8/CAP9 duplex (FIG. 11A), the CAP7, CAP8, and CAP9 oligonucleotides (SEQ ID NOS:9, 10 and 11, respectively) were mixed at 10 µM concentration in 100 µl of 50 mM Tris/HCl (pH 8.0), 100 mM NaCl, 1 mM EDTA, heated for 1 min at 95° C. and then cooled to 25° C. in 1 hr.

An additional advantage of this embodiment of the invention is that the incubation time necessary for the development of the signal is shortened, because when the nucleic acid components are linked, as shown in FIG. 11A, the rate of association reaction between the nucleic acid components is increased due to the relatively close proximity of each component. This variation of the invention is preferred if the attachment of the nucleic acid components to a solid support is desired. It is envisioned that a reactive amino group may be included in the linker, which would be used for the attachment of the entire nucleic acid construct to the solid support.

Figure 12:
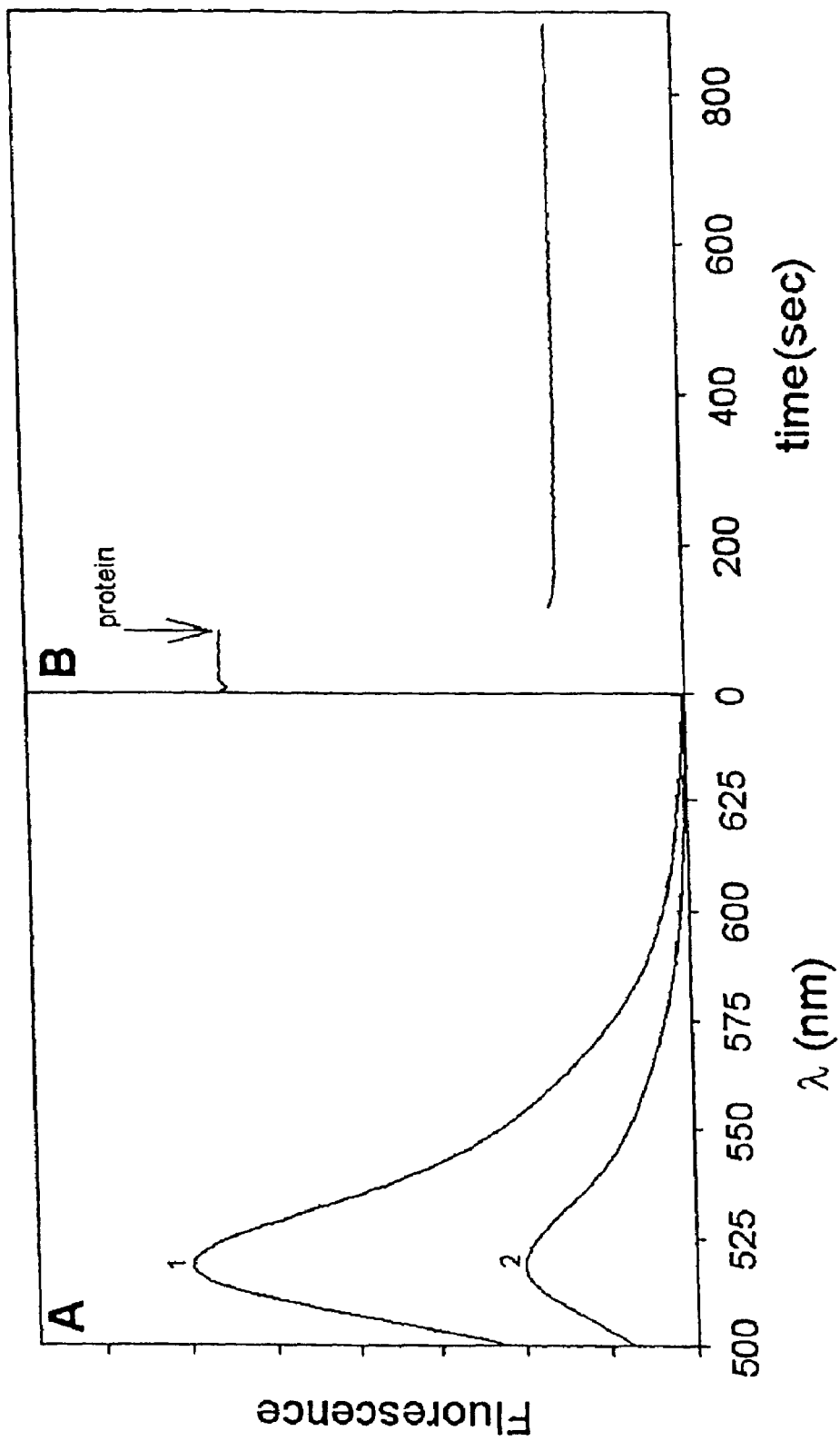
FIG. 12 depicts the fluorescence signal change observed in the presence of CAP using the covalently linked design depicted in FIG. 11 (panel A). Panel B depicts the response time of quenching using the flexible-linker construct.

FIG. 12 illustrates the enhanced performance of the variation of the invention depicted in FIG. 11. Curve 1 of FIG. 12A shows the spectrum of 50 nM of the CAP7/CAP8/CAP9 construct in 50 mM Tris/HCl (pH 8.0), 50 mM NaCl, 1 mM EDTA, 0.1 mg/ml BSA, and 200 µM cAMP. The addition of 75 nM CAP protein resulted in ~70% quenching of the fluorescence signal, demonstrating that a nucleic acid binding protein may be readily detected by this assay format. The kinetics of CAP induced fluorescence quenching was also studied to determine the incubation time necessary for the completion of the assay (FIG. 12B). In this experiment, the fluorescence intensity of 50 nM of the CAP7/CAP8/CAP9 construct was monitored as a function of time at 520 nm with the excitation wavelength set at 490 nm. At the time indicated by the arrow in FIG. 12B, 75 nM CAP protein was added and the monitoring of the fluorescence signal was resumed. The reaction was essentially completed within the time it took to add the CAP protein (within approximately 20 sec). Thus, the linking of the nucleic acid components resulted in a dramatic decrease in the time necessary for a change in the fluorescence signal to occur.

EXAMPLE 5

The Detection of the Lac Repressor Protein (LacR)

To illustrate the universal capability of the invention to detect, identify or quantify any nucleic acid binding protein, the following oligonucleotides, which comprise Lac repressor binding elements, were synthesized (F=dT-fluorescein, D=dT-dabcyl):

```
GGTGTGTGGAATTGTGA         (LAC1; SEQ ID NO:12)
GCGFATAACAATTTCACACAGG    (LAC2; SEQ ID NO:13)
CTTGTGTGAAATTGTT          (LAC3; SEQ ID NO:14)
ADACGCTCACAATTCCACACACC   (LAC4; SEQ ID NO:15)
```

Figure 13:
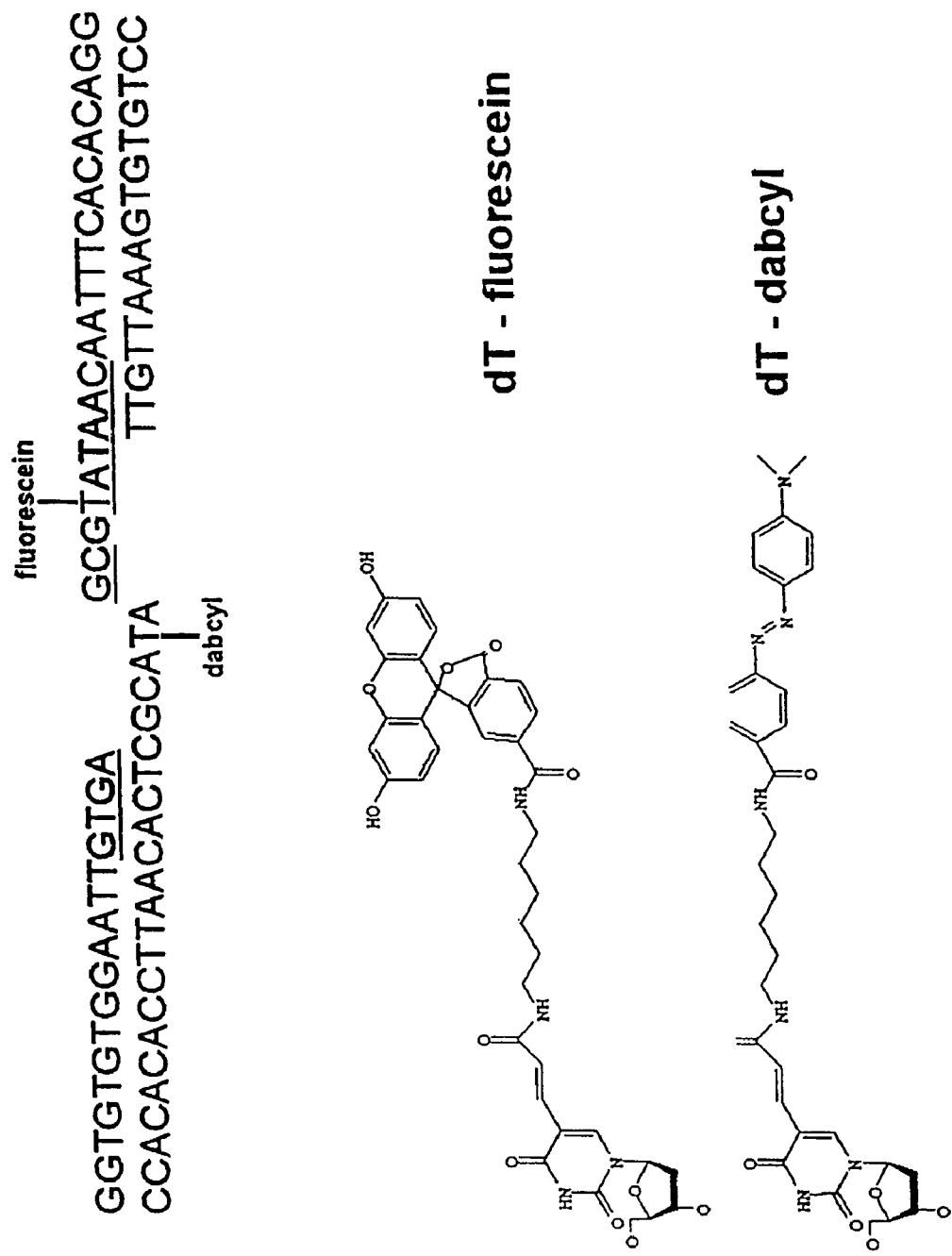
FIG. 13 depicts the fluorochrome-labeled oligonucleotides used for the detection of the LacR protein. The first nucleic acid component (left) comprises SEQ ID NO:12 (top) and SEQ ID NO:15 (bottom). The second nucleic acid component (right) comprises SEQ ID NO:13 (top) and SEQ ID NO:14 (bottom).

The oligonucleotides were purified using reverse phase chromatography on RPC column (Amersham Pharmacia Biotech, Piscataway, N.J.) as previously described (Heyduk, E., and Heyduk, T. Anal. Biochem. 248, 216–227, 1997). The fractions containing the oligonucleotides were dried in Vacuum centrifuge concentrator and were dissolved in 50 µl of water. The concentration of the stock solutions of oligonucleotides was determined by recording the UV-VIS absorption spectrum of a small aliquot of the stock solution diluted to 400 µl. The LAC1 oligonucleotide (SEQ ID NO:12) was hybridized with the LAC4 oligonucleotide (SEQ ID NO:15) to generate the LAC1/LAC4 construct and the LAC2 oligonucleotide (SEQ ID NO:13) was hybridized with the LAC3 oligonucleotide (SEQ ID NO:14) to generate the LAC2/LAC3 construct. For the hybridization, the appropriate oligonucleotides were mixed at 10 µM concentration in 100 µl of 50 mM Tris/HCl (pH 8.0), 100 mM NaCl, 1 mM EDTA, heated for 1 min at 95° C. and then cooled to 25° C. for 1 hr. All subsequent fluorescence measurements were performed at 25° C. in 50 mM Tris/HCl (pH 8.0), 100 mM NaCl, 1 mM EDTA, and 0.1 mg/ml BSA. The double stranded nucleic acid constructs obtained upon hybridization are illustrated in FIG. 13. The duplexes contain a LacR binding site (underlined sequence) derived from the Lac operon sequence split between each of the two double stranded constructs.

Figure 14:
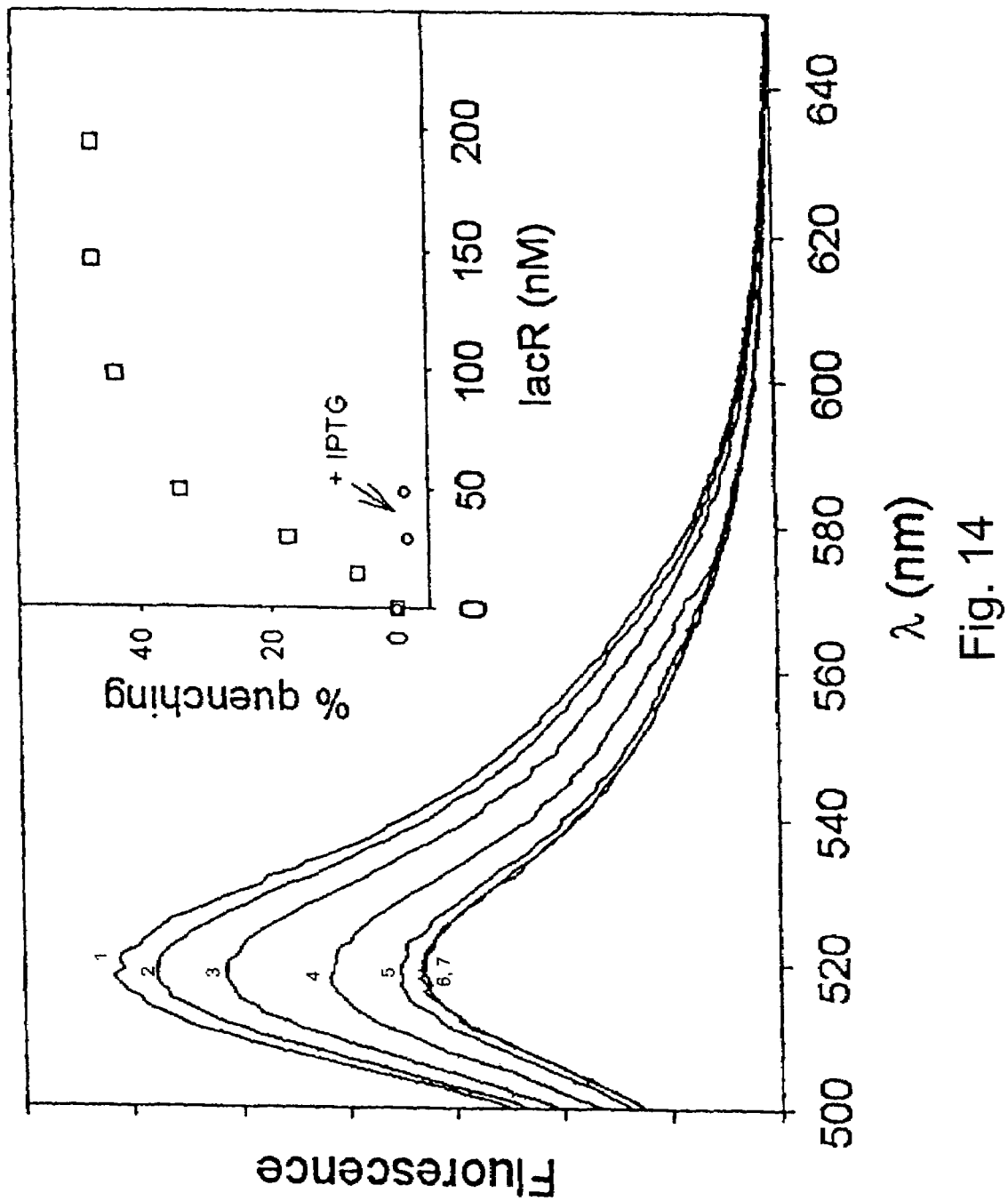
FIG. 14 depicts fluorescent quenching due to the binding of LacR protein to the cognate DNA sequences. Curves 1–7 represent increasing amounts of LacR protein, from 0 to 200 nM, respectively.

The fluorescence spectra of 50 nM of LAC1/LAC4 plus LAC2/LAC3 were recorded in the absence of LacR (FIG. 14, curve 1) and in the presence of varying amounts of LacR in a range from 0–200 nM (FIG. 14, curves 2–7). Fluorescence signal quenching was proportional to the amount of LacR added to the reaction mixture, with saturation occurring at approximately 150 nM of LacR (FIG. 14, inset). Thr specificity of LacR detection was confirmed by adding 5 mM IPTG to the assay mixture, which selectively binds to LacR and reduces its nucleic acid binding activity.

EXAMPLE 6

The Detection of the Trp Repressor Protein (TrpR)

To further illustrate the universal capability of the present invention to detect any and all nucleic acid binding proteins, the following oligonucleotides, which comprise a Trp repressor binding element, were synthesized (F=dT-fluorescein, D=dT-dabcyl):

```
GAGATCTATCGAACTA              (TRP1; SEQ ID NO:16)
GFA AAC TAG TAC GAA ACT AGA G (TRP2; SEQ ID NO:17)
```

-continued

CTC TAG TTT CGT ACT A           (TRP3; SEQ ID NO:18)

GDT TAC TAG TTC GAT AGA TCT C (TRP4; SEQ ID NO:19)

Figure 15:
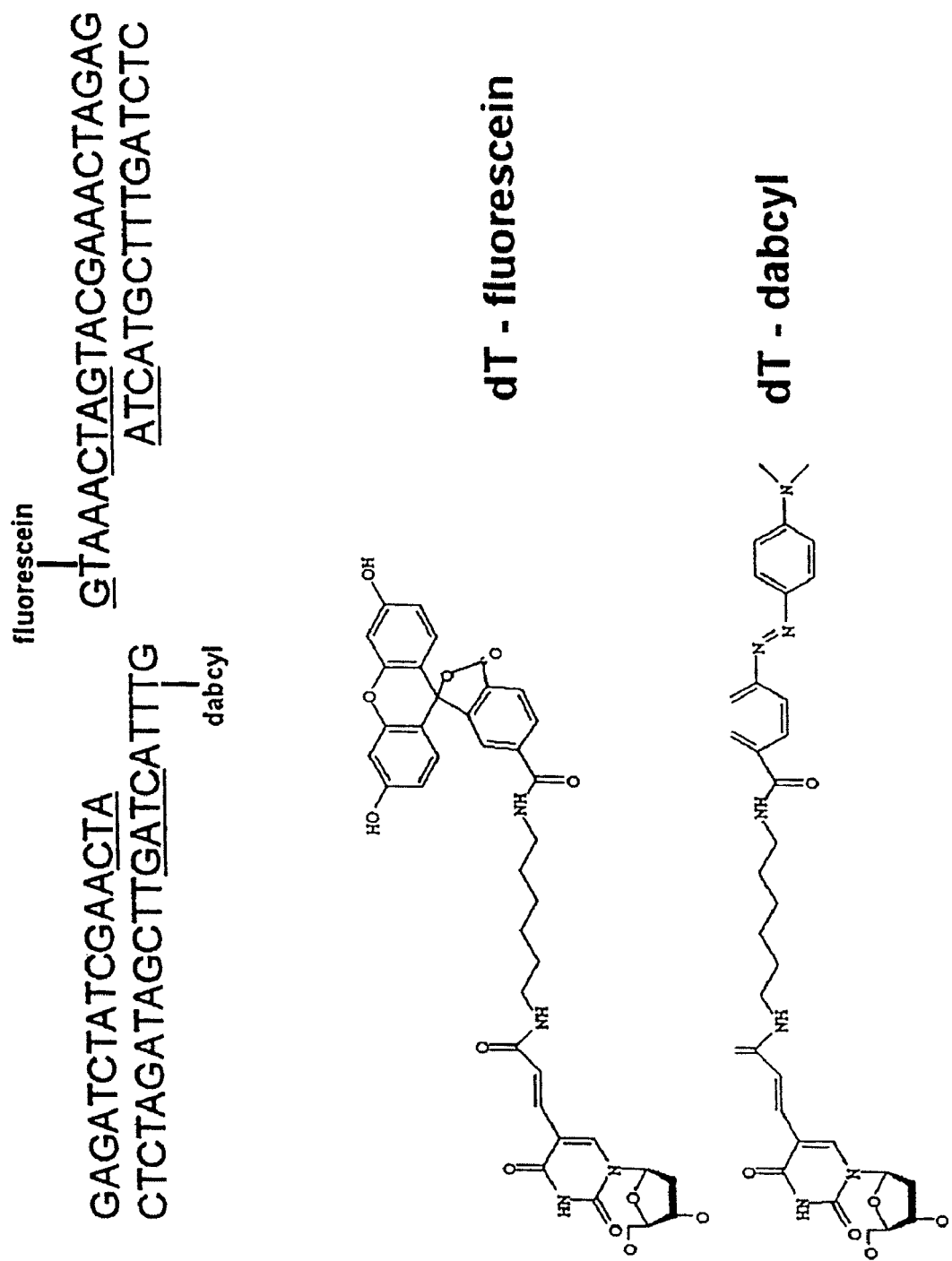
FIG. 15 depicts nucleic acid duplexes containing portions of the TrpR protein binding sites. The first nucleic acid component (left) comprises SEQ ID NO:16 (top) and SEQ ID NO:19 (bottom). The second nucleic acid component (right) comprises SEQ ID NO:17 (top) and SEQ ID NO:18 (bottom).

The oligonucleotides were purified using reverse phase chromatography on RPC column (Amersham Pharmacia Biotech, Piscataway, N.J.) as previously described (Heyduk, E., and Heyduk, T. *Anal. Biochem.* 248, 216–227, 1997). The fractions containing the oligonucleotides were dried in Vacuum centrifuge concentrator and were dissolved in 50 µl of water. The concentration of the stock solutions of oligonucleotides was determined by recording the UV-VIS absorption spectrum of a small aliquot of the stock solution diluted to 400 µl. The TRP1 oligonucleotide (SEQ ID NO:16) was hybridized with the TRP4 oligonucleotide (SEQ ID NO:19) to generate the TRP1/TRP4 construct and the TRP2 oligonucleotide (SEQ ID NO:17) was hybridized with the TRP3 oligonucleotide (SEQ ID NO:18) to generate the TRP2/TRP3 construct. For the hybridization, the appropriate oligonucleotides were mixed at 10 µM concentration in 100 µl of 50 mM Tris/HCl (pH 8.0), 100 mM NaCl, 1 mM EDTA, heated for 1 min at 95° C. and then cooled to 25° C. for 1 hr. All subsequent fluorescence measurements were performed at 15° C. in 10 mM potassium phosphate (pH 7.6), 50 mM NaCl, 0.1 mM EDTA, 4mM tryptophan, 10% glycerol, 0.01% sodium azide and 1.0 mg/ml BSA. The double stranded nucleic acid constructs obtained upon hybridization are illustrated in FIG. 15. The duplexes contain a TrpR binding site (underlined sequence) split between each of the two double stranded constructs.

Figure 16:
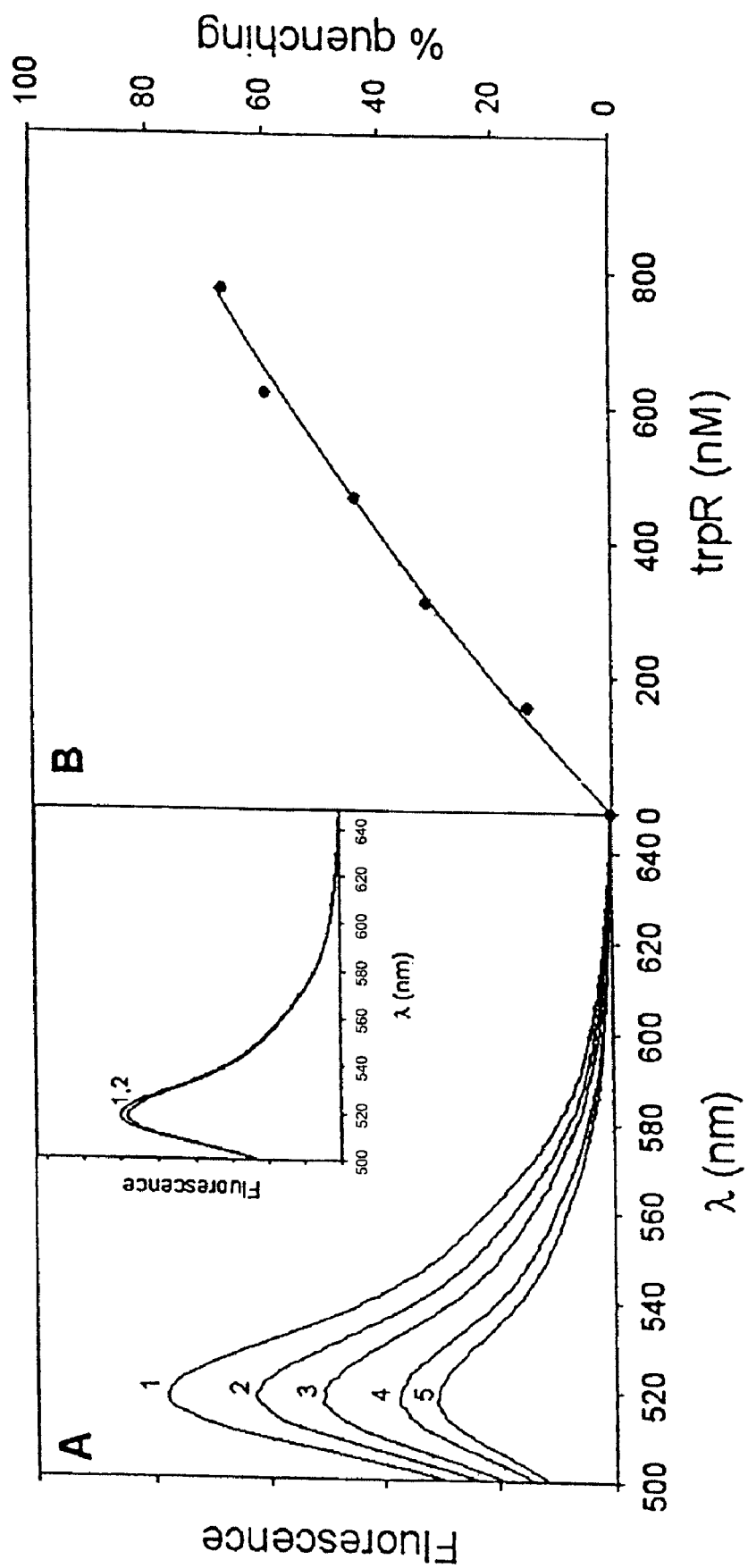
FIG. 16 depicts fluorescent quenching due to the binding of TrpR protein to the cognate DNA sequences. Curves 1–5 represent increasing amounts of TrpR protein, from 0 to 800 nM, respectively (panel A). Panel B plots fluorescence quenching as a function of the concentration of TrpR protein.

The fluorescence spectra of 250 nM TRP1/TRP4 and 300 nM TRP2/TRP3 were recorded in the absence of TrpR (FIG. 16A, curve 1) and in the presence of varying amounts of TrpR in a range from 0–800 nM (FIG. 16A, curves 2–5). Fluorescence signal quenching was proportional to the amount of TrpR added to the reaction mixture, with saturation occurring at approximately 150 nM of LacR (FIG. 16B). The specificity of TrpR detection was confirmed by the addition of TrpR to a reaction mixture containing the nucleic acid components used for detecting LacR protein (FIG. 16A, inset, curves 1 and 2).

EXAMPLE 7

The Simultaneous Detection of Two Proteins Using a Two-color Detection Protocol

The compatibility of the assays described in the instant invention with a variety of fluorescence probes emitting at different wavelengths allows for the designing of variations in which two or more proteins may be detected simultaneously. Nucleic acid constructs specific for each of the proteins to be detected may be labeled with probes that emit light at different wavelengths. In this example, the reaction mixture contained nucleic acid constructs labeled with 7-diethylaminocoumarin-3-carboxylic acid for detecting CAP protein (described in EXAMPLE 2) and nucleic acid constructs labeled with fluorescein for detecting TrpR protein (described in EXAMPLE 6). Specifically, 100 nM CAP5/CAP3, 120 nM CAP1/CAP4, 100 nM TRP2/TRP3, and 120 nM TRP1/TRP4 duplexes were present in the reaction mixture.

Figure 17:
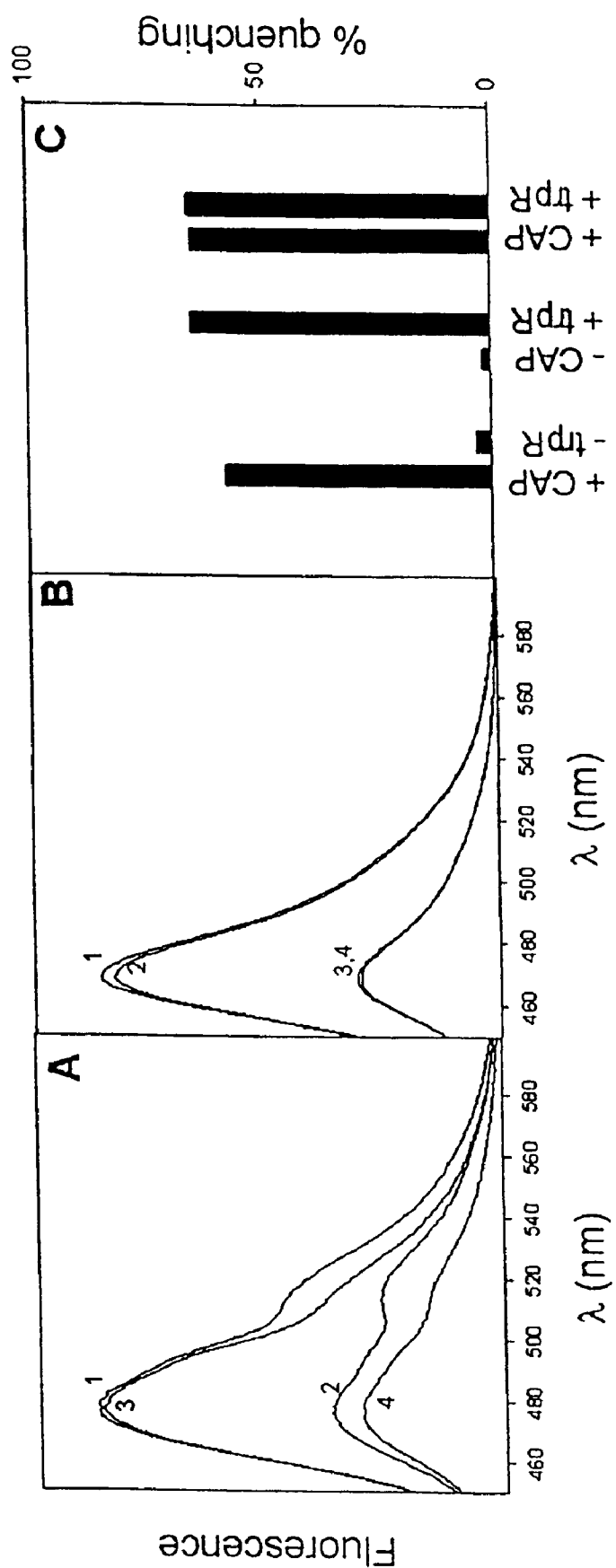
FIG. 17 depicts the simultaneous two-color detection of two proteins, CAP and TrpR. Panel A depicts the fluorescence spectra obtained at 433 nm excitation wavelength and panel B depicts the fluorescence spectra obtained at 490 nm excitation wavelength. Curve 1 is in the absence of both proteins; curve 2 in the presence of CAP only; curve 3 in the presence of TrpR only; and curve 4 in the presence of both CAP and TrpR. Panel C summarizes the results from panels A and B.

FIG. 17 shows the results of the experiment illustrating this capability. All measurements were performed at 15° C. in 10 mM potassium phosphate (pH 7.6), 50 mM NaCl, 0.1 mM EDTA, 4 mM tryptophan, 200 µM cAMP, 10% glycerol, 0.01% sodium azide and 1.0 mg/ml BSA. The fluorescence spectra with the excitation at 433 nm (excitation of 7-diethylaminocoumarin-3-carbo acid, FIG. 17A) and with the excitation at 490 nm (excitation of fluorescein, FIG. 17B) were recorded in the absence of the proteins (curves 1), in the presence of CAP only (curves 2), in the presence of TrpR only (curves 3), and in the presence of both CAP and TrpR (curves 4). In the presence of only CAP there was no change in the fluorescein signal (FIG. 17B, curve 2) whereas about 60% quenching of the 7-diethylaminocoumarin-3-carbox acid signal was observed (FIG. 17A, curve 2). In the presence of only TrpR there was no change in the 7-diethylaminocoumarin-3-carboxylic acid signal (FIG. 17A, curve 3) whereas about 60% quenching of the fluorescein signal was observed (FIG. 17B, curve 3). Finally, when both CAP and TrpR were present the quenching of both emission spectra was observed (FIG. 17A & B, curves 4). FIG. 17C summarizes these results in a form of a bar plot in which the dark bars correspond to the quenching observed at the color for CAP detection, and shaded bars correspond to the quenching at the color for detection of TrpR. It is evident from the data presented in this example that simultaneous multi-color detection of two or more nucleic acid binding protein coregulators may also be achieved using the assay described in the present invention.

EXAMPLE 8

The Detection of p53 Protein

Mutations in the p53 protein are crucial to the development of many tumors, wherein a majority of tumors contain mutations in this protein (Ko, L. L., and Prives, C. *Genes Dev.* 10, 1054–1072, 1996). Furthermore, tumors that lack functional p53 protein are recalcitrant to radiation therapy. The p53 protein binds double-stranded DNA in a sequence specific manner and its nucleic acid binding activity is essential for its function. The majority of mutant p53s isolated from human tumors are deficient in nucleic acid binding activity. Therefore, functional assays directed to the presence of and specific activity of p53 will provide an important diagnostic tool to be used in cancer identification and treatment.

To illustrate the capability of the assay for the detection of p53 protein, the following oligonucleotides, which comprise a cognate p53 binding element, were synthesized (F=dT-fluorescein, D=dT-dabcyl):

```
                           (P1; SEQ ID NO:20)
    GCA TCG GTC ACA GAC A (P2; SEQ ID NO:21)
    TGC CFA GAC ATG CCT TGC AGT CTC GA (P3; SEQ ID NO:22)
    TCG AGA CTG CAA GGC A (P4; SEQ ID NO:23)
    TGT CDA GGC ATG TCT GTG ACC GAT GC
```

Figure 18:
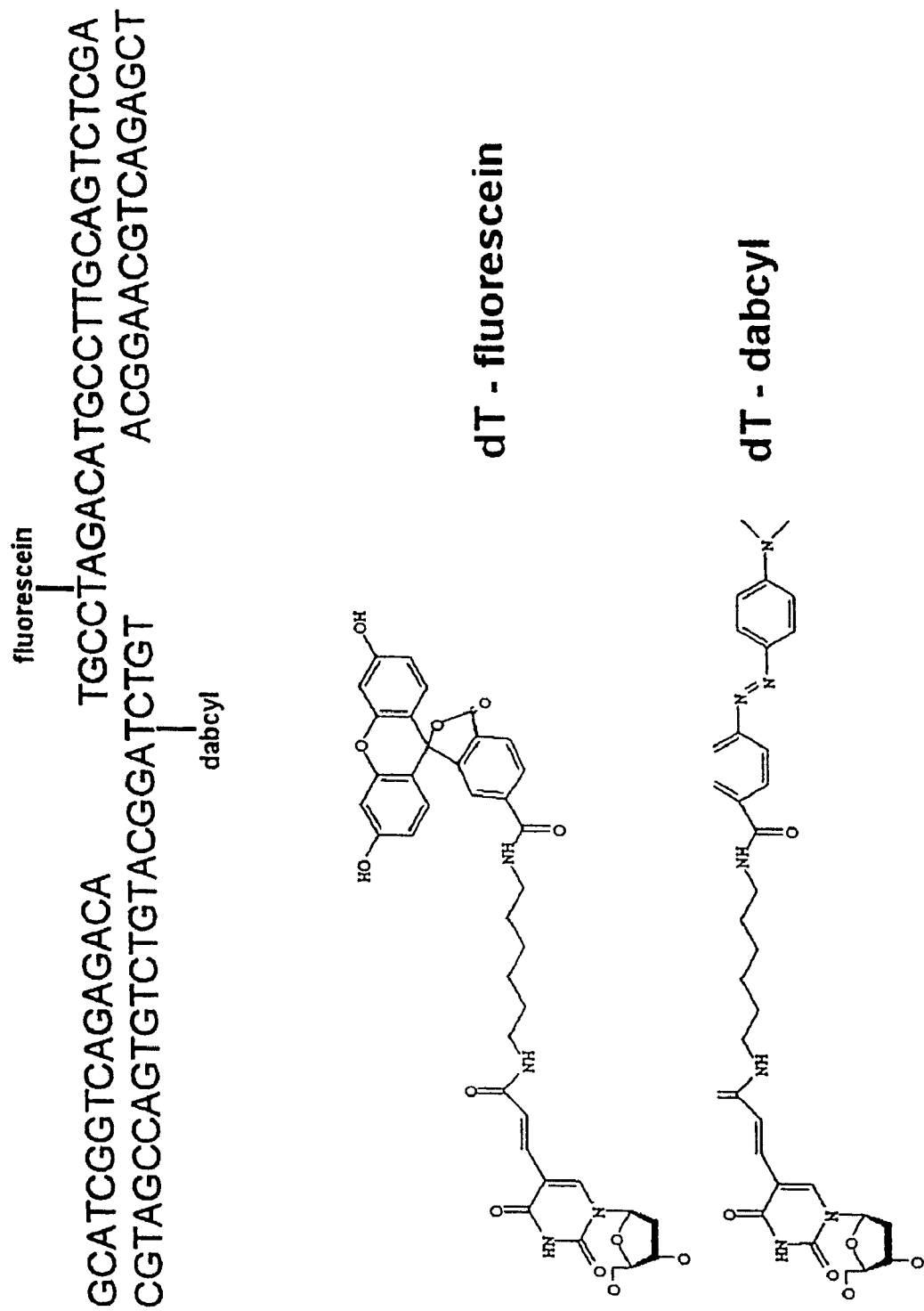
FIG. 18 depicts the nucleic acid duplexes containing portions of the p53 protein nucleic acid binding element. The first nucleic acid component (left) comprises SEQ ID NO:20 (top) and SEQ ID NO:23 (bottom). The second nucleic acid component (right) comprises SEQ ID NO:21 (top) and SEQ ID NO:22 (bottom).

The oligonucleotides were purified using reverse phase chromatography on a RPC column as described previously (Heyduk, E., and Heyduk, supra). The fractions containing the oligonucleotides were dried in Vacuum centrifuge concentrator and were dissolved in 50 µl of water. The concentrations of the stock solutions of oligonucleotides were determined by recording the UV-VIS absorption spectrum of a small aliquot of the stock solution diluted to 400 µl. The P1 oligonucleotide (SEQ ID NO:20) was hybridized with the P4 oligonucleotide (SEQ ID NO:23) to generate the P1/P4 duplex construct and the P2 oligonucleotide (SEQ ID NO:21) was hybridized with the P3 (SEQ ID NO:22) oligonucleotide to generate the P2/P3 duplex construct. For the hybridization, the appropriate oligonucleotides were mixed at 10 µM concentration in 100 µl of 50 mM Tris/HCl (pH 8.0), 100 mM NaCl, 1 mM EDTA, heated for 1 min at 95° C. and then cooled to 25° C. for 1 hr. All subsequent fluorescence measurements were performed at 25° C. in 50-mM potassium phosphate (pH 7.5), 50 mM NaCl, and 0.5 mg/ml BSA containing also 100 nM of a nonspecific 30-bp DNA duplex. The DNA duplexes obtained upon hybridization are illustrated in FIG. 18. The duplexes contain a repeat of 10 bp PuPuPuC(A/T)(T/A)GPyPyPy (SEQ ID NO:24) motif split between the two DNA duplexes. This sequence (SEQ ID NO:24) has been identified as a consensus p53 recognition sequence (El-Deiry, W. S., Kern, S. E., Pietenpol, J. A., Kinzler, K. W., and Vogelstein, B. *Nature Genetics,* 1, 45–49, 1992). The p53 protein used in this assay was a human recombinant full-length protein expressed in bacteria (a gift from Dr. Kathleen S. Matthews; Nichols, N. M., and Matthews, K. S. *Biochemistry* 40, 3847–3858, 2001, which is herein incorporated by reference).

Figure 19:
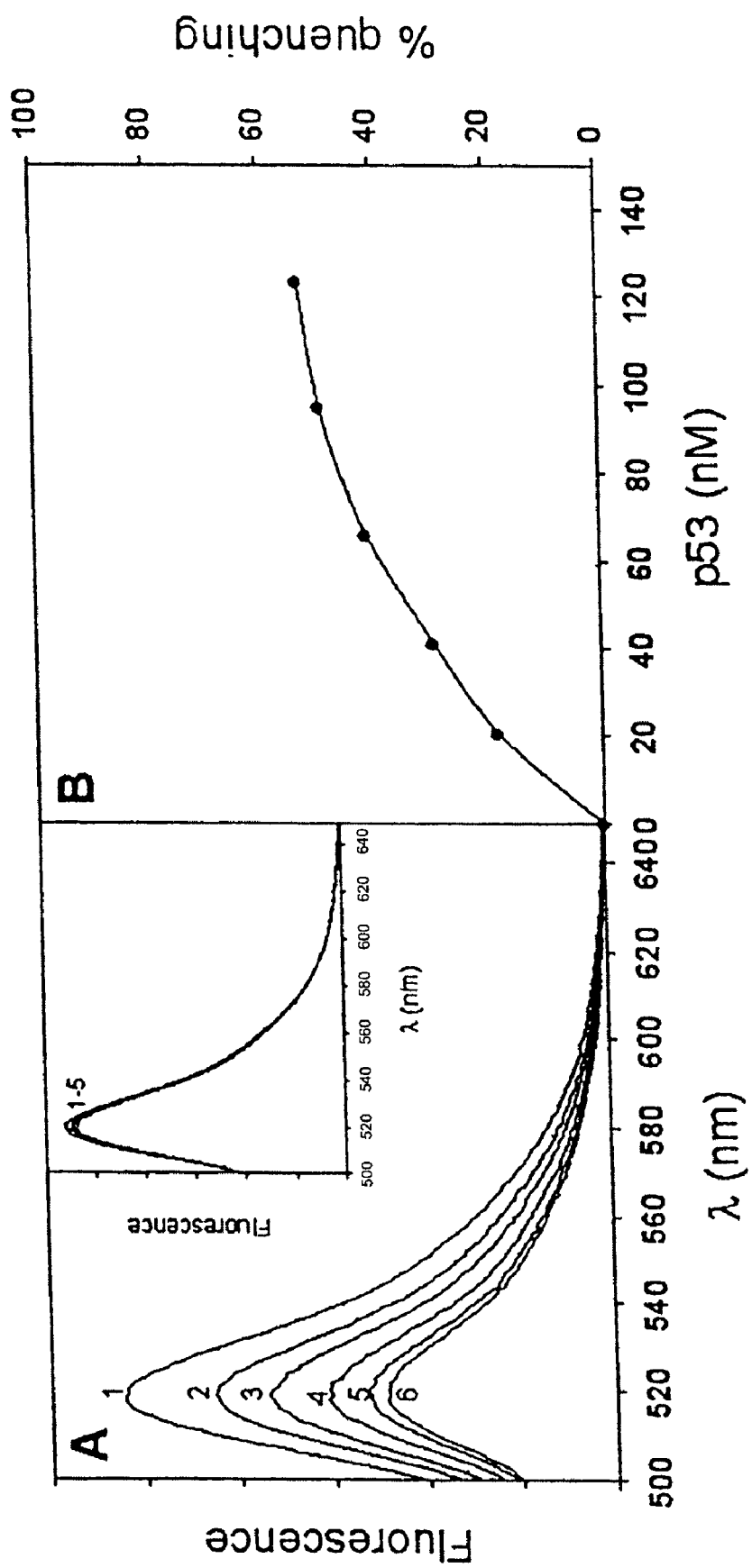
FIG. 19 depicts fluorescence quenching due to the binding of p53 protein to the cognate nucleic acid binding element sequences. Curves 1–6 represent increasing amounts of p53 protein, from 0 to 130 nM, respectively (panel A). Panel B plots fluorescence quenching as a function of the concentration of p53 protein.

The fluorescence spectra of 25 nM P1/P4 plus 30 nM P2/P3 were recorded in the absence of p53 protein (FIG. 19A, curve 1) and in the presence of varying amounts of p53 in a range from 0–130 nM (FIG. 19A, curves 2–6). The observed quenching of the fluorescence signal was proportional to the amount of p53 protein added to the assay mixture (FIG. 19B). The specificity of this particular assay for p53 detection was confirmed, by the demonstrating a lack of fluorescence quenching upon addition of p53 protein to a reaction mixture containing the nucleic acid constructs CAP1/CAP4 plus CAP2/CAP3 (FIG. 19A, inset, curve 1 corresponds to the signal in the absence of p53 whereas curves 4–5 correspond to the signal observed upon adding 1–90 nM p53). Taken together, this example demonstrates that the present invention is universally applicable to any and all nucleic acid binding proteins, including important mammalian tumor suppressor proteins, e.g., p53.

EXAMPLE 9

The Detection of Nucleic Acid Binding Protein Coregulators Using Both Proximity-based and Non-proximity-based Detection Methods A large number of sequence-specific nucleic acid binding factors has evolved in living organisms to regulate gene expression in response to environmental stimuli. The nucleic acid binding activity of many of these factors is mediated via the direct or indirect interaction of the nucleic acid binding factor with a small coregulator or post-translational modification. Many of these coregulators are of interest due to their role in environmental science (common pollutants), forensic science and toxicology. Many of these coregulators are cellular metabolites or molecules playing signaling or regulatory roles in cells. Thus, their detection is of interest in clinical chemistry and medical diagnosis.

A large number of coregulator-regulated nucleic acid binding factors exist in nature for which there is a need for tools and methods to determine the activity of their respective coregulators. Examples of such coregulators and their corresponding nucleic acid binding factors whose nucleic acid binding activity is regulated by these coregulators include cAMP and cAMP receptor protein (Busby, S. & Ebright, R. H., *J. Mol. Biol.* 293, 199–213 [1999]), S-adenosylmethionine (SAM) and MetJ protein (Philllips, K., and Phillips, S. E. V., *Structure* 2, 309–316 [1994]), or arsenite and ArsR protein (Wu, J., and Rosen, B. P., *J. Biol. Chem.* 268, 52–58 [1992]). cAMP is one of the central signaling molecules in eukaryotic cells. There are more then 20 hormones which activate or inhibit adenylate cyclase thereby affecting cellular levels of cAMP. Due to its central role in cellular signaling, there is a continuing interest in the measurement of cAMP levels in tissues and cells. SAM is a donor of the methyl group in the cell, serving to donate methyl groups to a variety of targets including DNA, phospholipids, and proteins. Due to the importance of SAM in tissue function, there is a continuing interest in the measurement of its levels in tissues and cells. Arsenite is a common toxic impurity and thus the determination of its level in water, soil, and food, among others, is important. These examples represent only a small fraction of coregulator-regulated nucleic acid binding factors which could be found in bacteria and other microorganisms. There are hundreds of known coregulator-regulated nucleic acid binding factors and hundreds more yet to be discovered.

Figure 20:
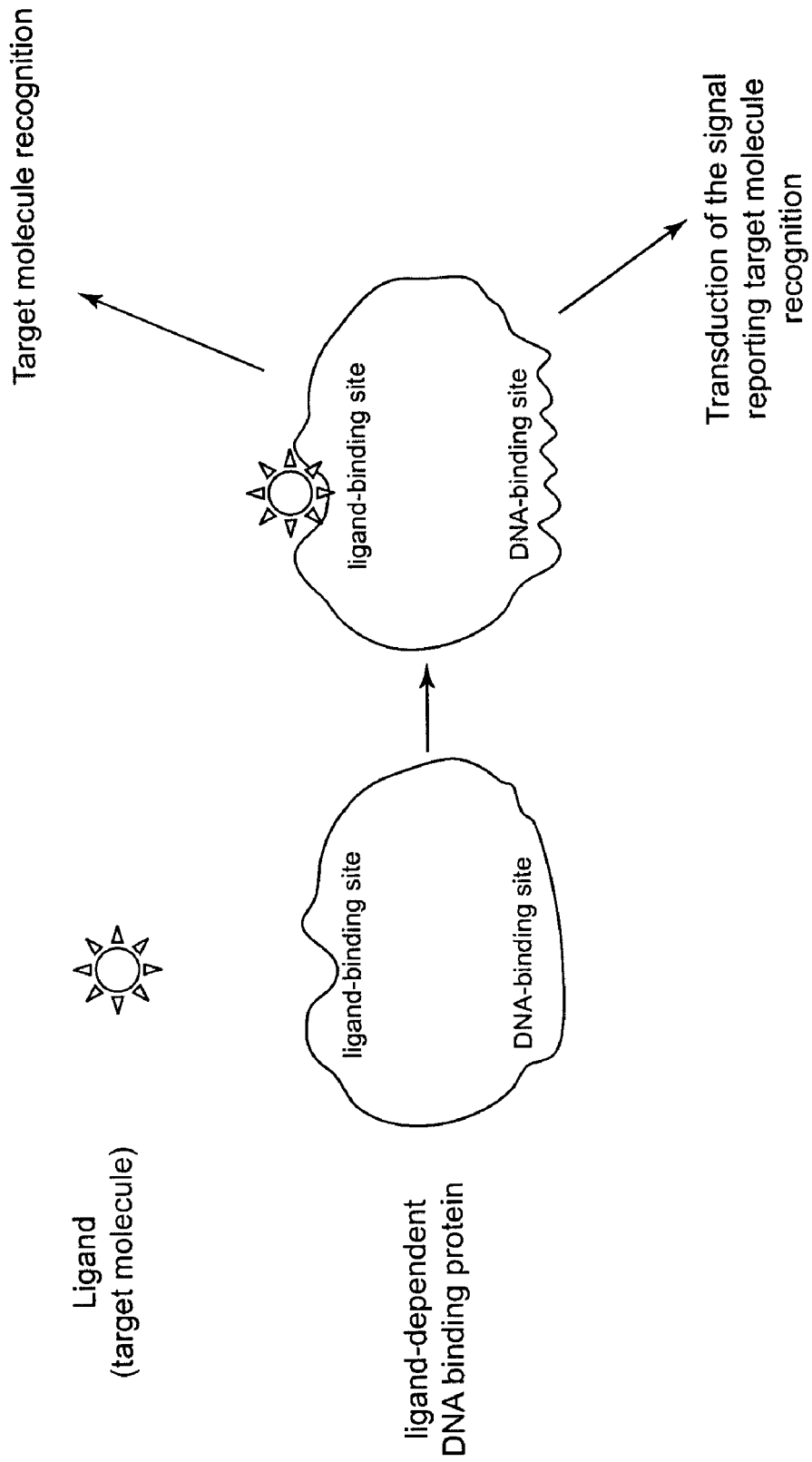
FIG. 20 depicts the use of a ligand-dependent DNA binding protein in a biosensor to determine the activity of a ligand (target molecule). Target molecule (ligand) recognition will be provided by the ligand binding site of the ligand-dependent DNA binding protein. The binding of the ligand to the protein induces a change in the DNA binding properties of the protein. This change in the DNA binding properties of the protein is used to generate a signal indicating the presence of the ligand (target molecule).

The inventor describes here a design of biosensors which are based on coregulator-regulated nucleic acid binding factor. The overall design of these biosensors is illustrated in FIG. 20. This design is applicable to any coregulator-regulated nucleic acid binding factor therefore it serves as a general platform for operating a large number of permutations of biosensors. Detection of the target nucleic acid binding protein coregulator will be accomplished by measuring a decrease or increase in nucleic acid-protein complex induced by the target coregulator molecule. While any methodology to detect formation of a nucleic acid-protein complex could be used, the preferred method will be to use detectable labels for sequence-specific nucleic acid binding factors, which were recently developed (Heyduk, T., and Heyduk, E. *Nature Biotechnology,* in press [2002]). Using detectable labels, the presence of the target molecule (such as a nucleic acid binding factor or coregulator) will be signaled by a change of fluorescence intensity or the detection of some other detectable label. The assay thus requires very few steps to operate and is compatible with a high-throughput format. The components of the assay illustrated in FIG. 20 can be also immobilized on a solid surface (for example, on a tip of the light guide or optical fiber) to create a solid-state integrated biosensor.

Figure 21:
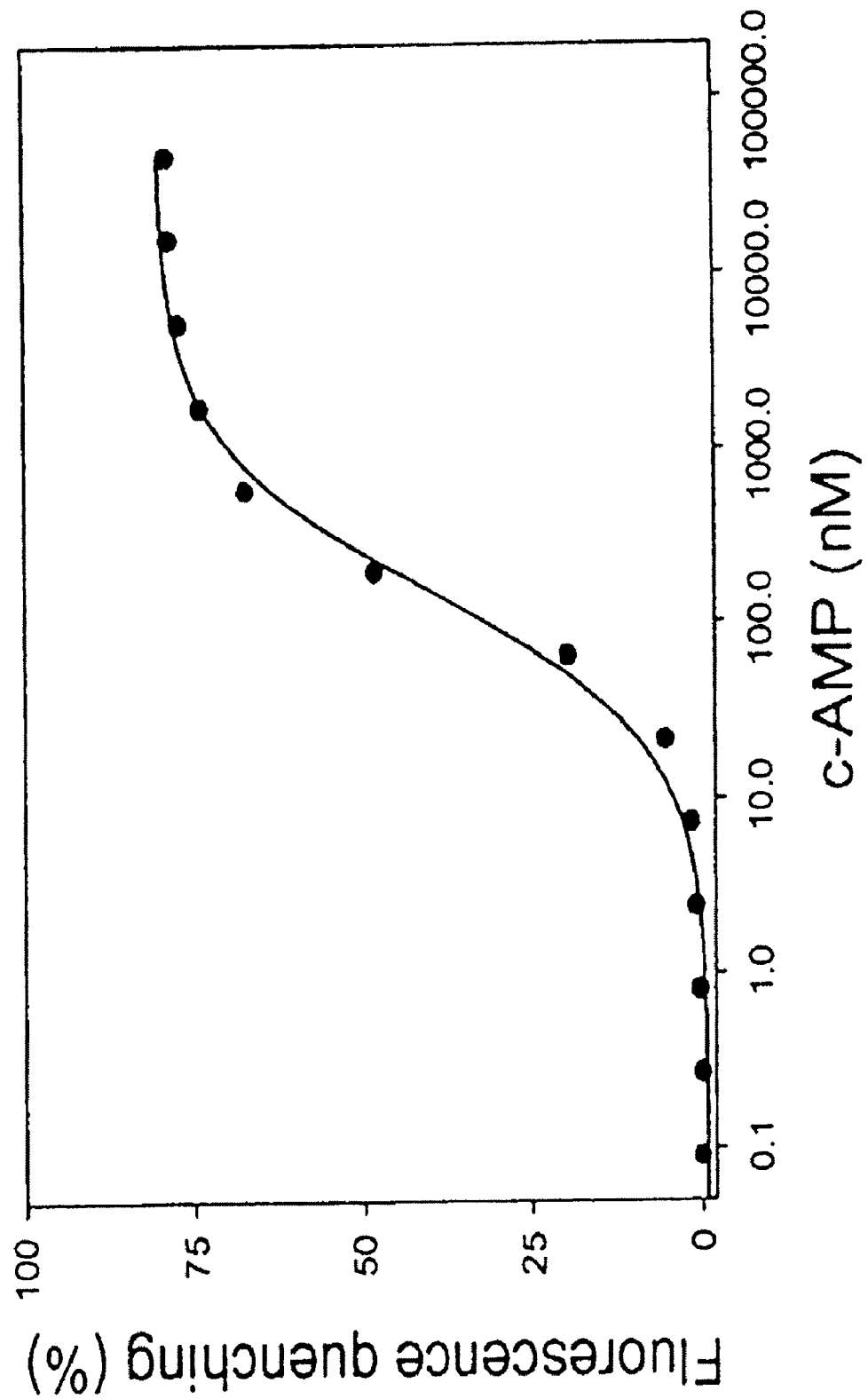
FIG. 21. demonstrates the detection of cAMP. Increasing concentrations of cAMP were added to a mixture containing 2 nM fluorescein labeled CAP-specific first nucleic acid component and 3 nM dabcyl-labeled CAP-specific second nucleic acid component. Fluorescence intensity of the test mixtures was read after 2 hrs of incubation at room temperature.
Figure 22:
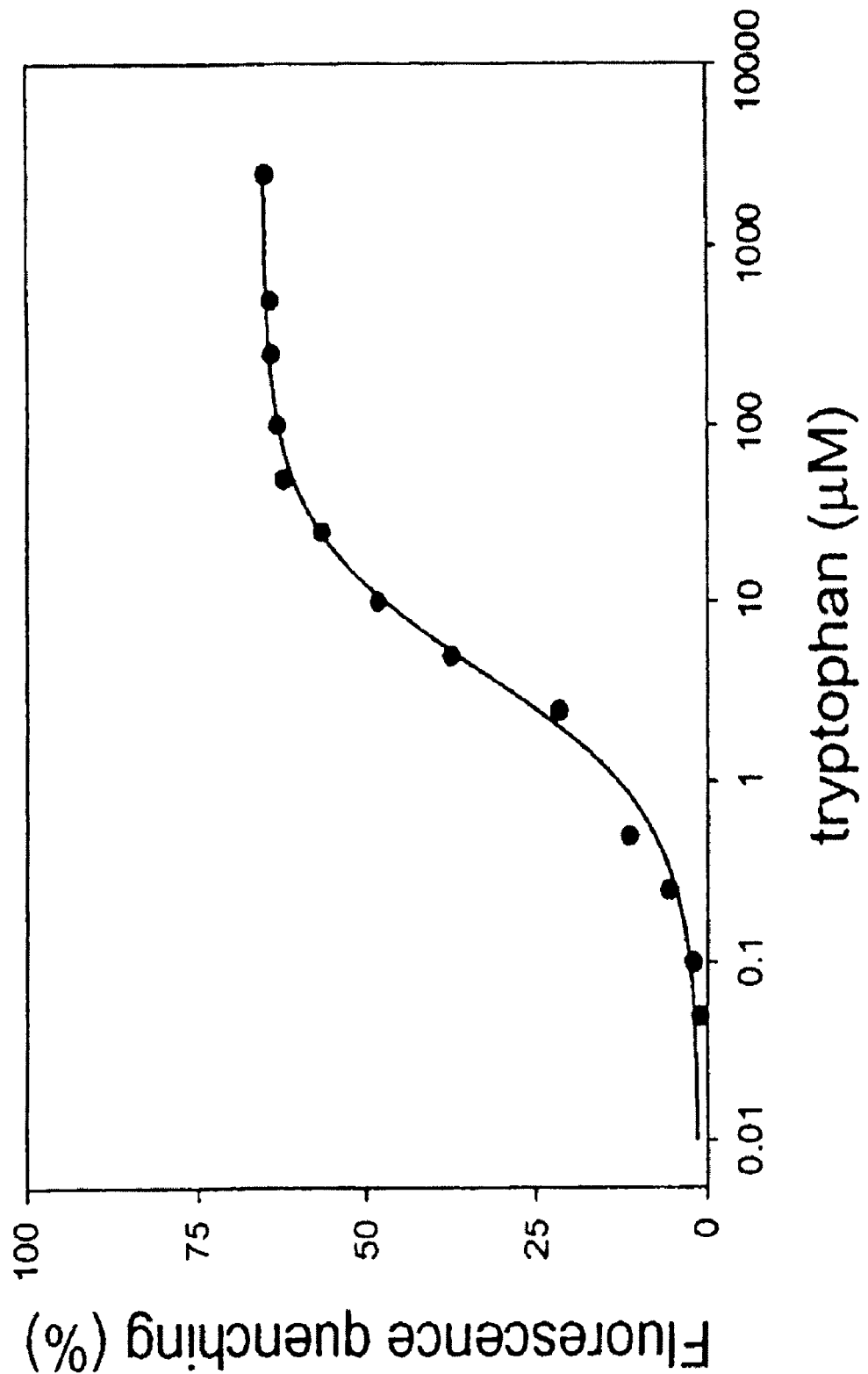
FIG. 22. demonstrates the detection of tryptophan. Increasing concentrations of tryptophan were added to a mixture containing 250 nM fluorescein labeled TrpR-specific first nucleic acid component and 300 nM dabcyl-labeled Trp-specific second nucleic acid component. Fluorescence intensity of the test mixtures was read after 2 hrs of incubation at room temperature.

The biosensor design and its general nature are illustrated by examples of biosensors recognizing cAMP, IPTG, and tryptophan. These three molecules are coregulators for three corresponding nucleic acid binding factors: CRP, Lac repressor, and Trp repressor. FIG. 21 shows the response of an exemplary cAMP biosensor to increasing amounts of cAMP. The test solution contained two nucleic acid components which comprise the CAP label (Heyduk, T., and Heyduk, E. *Nature Biotechnology,* in press [2002]) and the CAP protein. At the concentration of cAMP, where its level in the test mixture became sufficient to induce CAP protein to bind to its cognate nucleic acid binding element, a large fluorescence signal change was observed . This signal change was proportional to cAMP concentration (FIG. 21). Similar results were obtained with an analogous biosensor designed to detect tryptophan (FIG. 22). This particular biosensor comprised a mixture of TrpR protein and the two nucleic acid components corresponding to TrpR cognate nucleic acid element (Heyduk, T., and Heyduk, E. *Nature Biotechnology,* in press [2002]). As in the case of cAMP, at a certain range of tryptophan concentration, TrpR was induced to bind to its cognate nucleic acid element resulting in a large fluorescence signal change that was proportional to the amount of tryptophan added.

Figure 23:
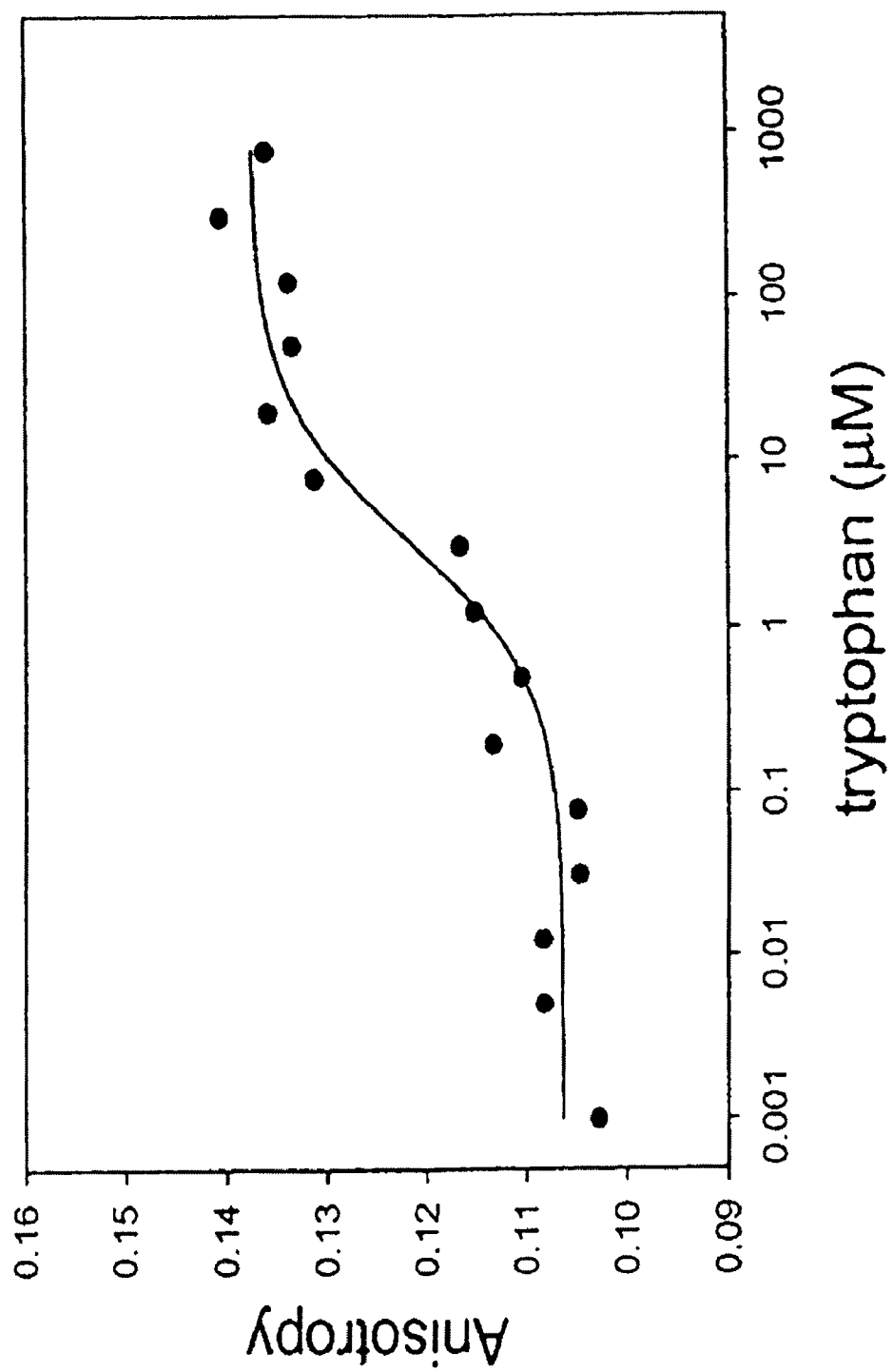
FIG. 23. demonstrates the detection of TrpR using fluorescence polarization. Increasing concentrations of tryptophan were added to a mixture containing 4 nM fluorescein-labeled 25 bp DNA duplex containing consensus TrpR binding sites. Fluorescence anisotropy of the test mixtures was read after 2 hrs of incubation at room temperature.

To illustrate that a different detection methodology for measuring the formation of nucleic acid-protein complexes could be accommodated to the biosensor design shown in FIG. 20, a biosensor for tryptophan was prepared wherein only one nucleic acid component was attached to a detectable label. According to this particular embodiment of the invention, fluorescence polarization of fluorochrome-labeled DNA component containing a TrpR cognate binding site was used to measure tryptophan-induced formation of a TrpR-nucleic acid complex (FIG. 23). A change of fluorescence polarization signal proportional to tryptophan concentration was observed showing that biosensors for any and all nucleic acid binding protein coregulators using the design according to FIG. 20 and using fluorescence polarization (or any detectable single label) as a signal for detection of the coregulator is included within the scope of the invention.

Figure 24:
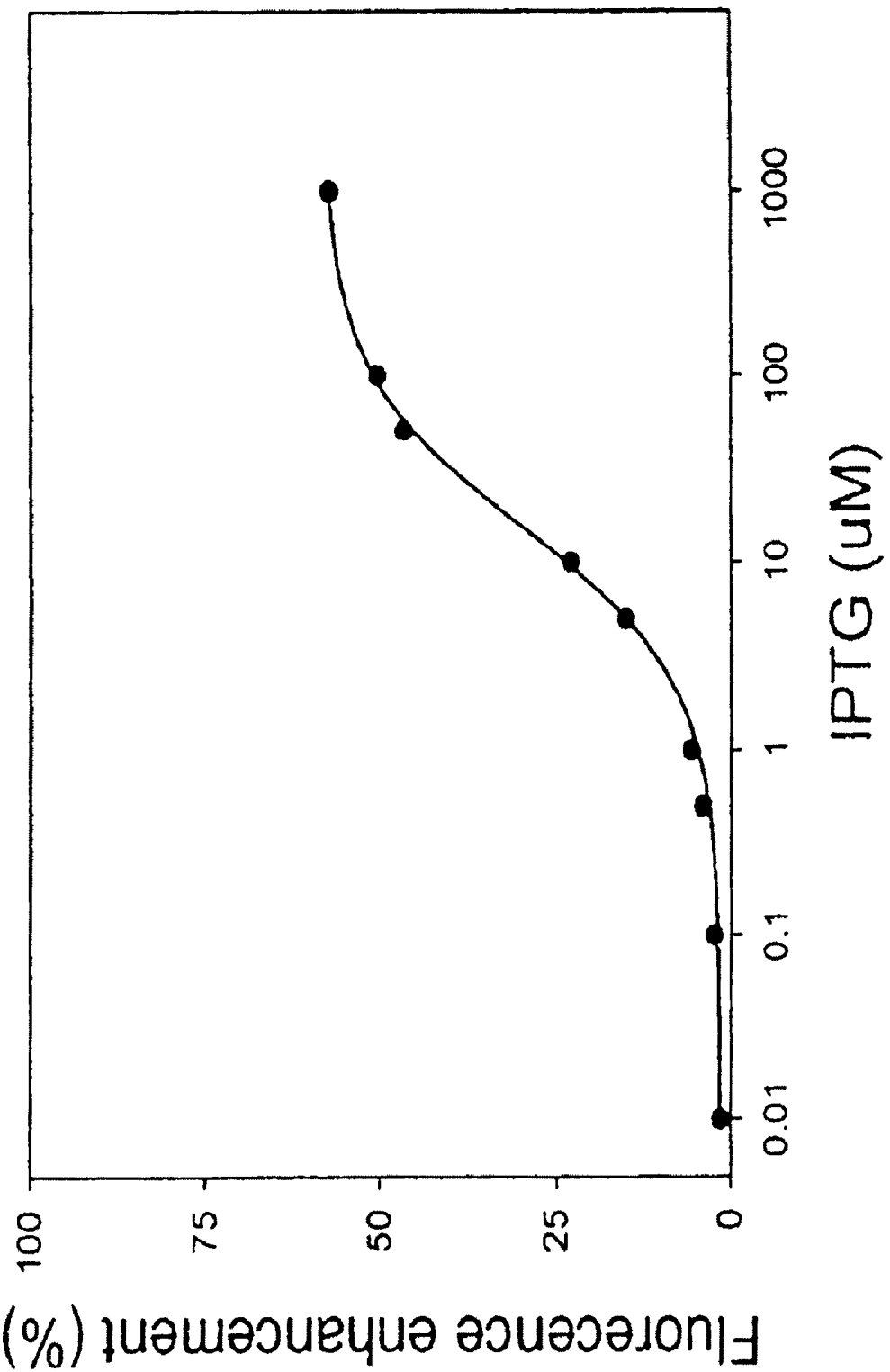
FIG. 24 describes a biosensor for detecting IPTG. Increasing concentrations of IPTG were added to a mixture containing 50 nM fluorescein-labeled LacR-specific first nucleic acid component and 60 nM dabcyl-labeled Lac-specific second nucleic acid component. Fluorescence intensity of the test mixtures was read after 2 hrs of incubation at room temperature.

FIG. 24 illustrates a biosensor design using a nucleic acid binding factor for which the coregulator reduced its affinity for a specific nucleic acid element. In this case, the coregulator will induce the dissociation of the protein-nucleic acid complex and its detection could be accomplished by coregulator-dependent disappearance of protein-nucleic acid complex. The biosensor in this case consisted of a mixture of LacR protein and the two nucleic acid components comprising the LacR cognate binding element (Heyduk, T., and Heyduk, E. Nature Biotechnology, in press [2002]). In the absence of IPTG (a coregulator for LacR) the LacR protein bound to its labeled cognate nucleic acid element resulting in quenching of the fluorescence signal. In the presence of increasing concentrations of IPTG, an IPTG-dependent increase in fluorescence signal was observed.

EXAMPLE 10

Assay Variant Wherein the First Component is Attached to Solid Support (Multiwell Plate) and the Second Component is Attached to a Detectable Label (Biotin)

To illustrate the extensive flexibility of the invention in terms of detection mode, an experiment following the general design depicted in FIG. 1E was performed. The following oligonucleotides, which when fully assembled contain a complete CAP nucleic acid binding element, were synthesized (X=amino-dT; B=biotin):

```
XAACGCAATAAATGTG             (CAP10; SEQ ID NO:25)

ATCTACTTCACATTTATTGCGTT      (CAP11; SEQ ID NO:26)

AAGTAGATCACATTTTAGGCACCB     (CAP12; SEQ ID NO:27)

GGTGCCTAAAATGTG              (CAP13; SEQ ID NO:28)
```

The CAP10 oligonucleotide was hybridized with the CAP11 oligonucleotide to generate the first nucleic acid component. The CAP 12 oligonucleotide was hybridized with the CAP13 oligonucleotide to generate the second nucleic acid component. For hybridization, appropriate oligonucleotides were (1) mixed at 10 µM concentration in 100 µl of buffer (500 mM $Na_2HPO_4$, pH 8.6, 1 mM EDTA, in the case of CAP10/CAP11 oligonucleotides; and 20 mM Tris, pH 8.0, 100 mM NaCl, 10 µM EDTA, in the case of CAP12/CAP13 oligonucleotides), (2) heated for 1 min at 95° C., and then (3) cooled to 25° C for 1 hr. The first nucleic acid component (CAP10/CAP11 half-site duplex) was covalently attached to the wells of a N-oxysuccinimide-activated 96 well plate (DNA-BIND, Corning, Acton, Mass.) by incubating 200 µl of first nucleic acid component (at 100 nM) per well in 500 mM $Na_2HPO_4$ (pH 8.6), 1 mM EDTA buffer for 1 hr followed by washing with 50 mM Tris (pH 8.0), 100 mM NaCl, 1 mM EDTA containing 0.1 mg/ml BSA. To the wells containing immobilized first component, a 10 nM or 20 nM solution of the second nucleic acid component (CAP12/CAP13 half-site duplex) was added followed by 250 nM CAP and 200 µM cAMP. After incubation for 1 hr at room temperature, the wells were washed twice with the buffer followed with the addition of streptavidin-linked horseradish peroxidase (Pierce, Rockford, Ill.) at the dilution recommended by the manufacturer. After 30 min of incubation, the wells were washed twice with buffer followed with the addition of 100 µl of Turbo-TMB™ peroxidase substrate solution (Pierce, Rockford, Ill.). The reaction was allowed to proceed for 15 min and was stopped by the addition of 100 µl of 1 M $H_2SO_4$ Control wells were treated the same way except that CAP and cAMP were omitted. The absorbance at 450 nm of the sample and control wells were read using a standard microplate reader. Table 2 summarizes the results of the experiment. At 10 nM CAP12/CAP13 an approximately 3 fold increase in absorbance signal was observed in the presence of CAP/cAMP compared to controls without CAP or cAMP, thus demonstrating the effectiveness of a multiwell and enzyme based detection format.

TABLE 2

| CAP12/CAP13 conc. (nM) | Absorbance (450 nm), no CAP | Absorbance (450 nm), + CAP |
|---|---|---|
| 10 | 0.2575 | 0.7308 |
| 20 | 0.4066 | 0.8584 |

As will be apparent to those skilled in the art in the light of the foregoing disclosures, many modifications, alterations and substitutions are possible in the practice of the present invention without departing from the spirit or scope thereof. The present invention is not limited only to the embodiments described in the foregoing, but rather by the scope of the claims which follow.

I claim:

1. A biosensor assay useful for determining the activity of a nucleic acid binding protein coregulator comprising a first nucleic acid component, a second nucleic acid component and a nucleic acid binding factor, wherein
   (a) the first nucleic acid component comprises a portion of a nucleic acid binding element and the second nucleic acid component comprises a portion of the same a nucleic acid binding element, wherein the combination of both the first and second nucleic acid components comprises the nucleic acid binding element; and
   (b) a detectable label is attached to the first nucleic acid component, the second nucleic acid component, or the nucleic acid binding factor, wherein the label is detected upon binding of the nucleic acid binding factor to the first and second nucleic acid components, to form a nucleic acid binding element, said binding being enhanced or disrupted by the nucleic acid binding protein coregulator.

2. The biosensor assay of claim 1 wherein the first nucleic acid component is attached to a solid substrate and the second nucleic acid is attached to a detectable label.

3. The biosensor assay of claim 2 wherein
   (a) the solid substrate is selected from the group consisting of multiwell plate, microarray slide, membrane, microsphere, light guide, optical fiber, conducting material, and surface of plasmon resonance chip, and
   (b) the detectable label is selected from the list consisting of a fluorochrome, chromophore, enzyme, linker molecule, biotin, electron donors, electron acceptors, dyes, metals, and radionuclide.

4. The biosensor assay of claim 3 wherein the solid substrate is a multiwell plate and the detectable label is biotin.

5. The biosensor assay of claim 1 wherein the detectable label is selected from the list consisting of a fluorochrome, chromophore, enzyme, linker molecule, biotin, electron donors, electron acceptors, dyes, metals, and radionuclide.

6. The biosensor assay of claim 5 wherein the first nucleic acid component is attached to a fluorescence donor, the second nucleic acid component is attached to a fluorescence acceptor.

7. The biosensor assay of claim 6 wherein the nucleic acid binding factor is a transcription factor selected from the group consisting of p53, TrpR, cAMP receptor protein, and Lac repressor.

8. The biosensor assay of claim 1 wherein the nucleic acid binding factor is attached to a solid matrix.

9. A method of determining the activity of a nucleic acid binding protein coregulator in a sample comprising,
   (a) combining a first nucleic acid component, a second nucleic acid component, and a nucleic acid binding factor with the sample wherein
      (i) the first nucleic acid component comprises a portion of a nucleic acid binding element and the second nucleic acid component comprises a portion of the same nucleic acid binding element, wherein the combination of both the first and second nucleic acid components comprises the nucleic acid binding element; and
      (ii) a detectable label is attached to the first nucleic acid component, the second nucleic acid component, or the nucleic acid binding factor, wherein the label is detected upon binding of the nucleic acid binding factor to the first and second nucleic acid components, to form a nucleic acid binding element, said binding being enhanced or disrupted by the nucleic acid binding protein coregulator; and
   (b) detecting the activity of the nucleic acid binding protein coregulator by a detection method.

10. The method of claim 9 wherein the first nucleic acid component is attached to a solid substrate and the second nucleic acid is attached to a detectable label.

11. The method of claim 10 wherein
    (a) the solid substrate is selected from the group consisting of multiwell plate, microarray slide, membrane, microsphere, light guide, optical fiber, conducting material, and surface of plasmon resonance chip, and
    (b) the detectable label is selected from the list consisting of a fluorochrome, chromophore, enzyme, linker molecule, biotin, electron donors, electron acceptors, dyes, metals, and radionuclide.

12. The method of claim 11 wherein the detectable label is biotin and the solid substrate is a multiwell plate.

13. The method of claim 9 wherein the detectable label is selected from the list consisting of a fluorochrome, chromophore, enzyme, linker molecule, biotin, electron donors, electron acceptors, dyes, metals, and radionuclide.

14. The method of claim 13 wherein the first nucleic acid component is attached to a fluorescence donor, the second nucleic acid component is attached to a fluorescence acceptor, and the detection method is fluorescence resonance energy transfer.

15. The method of claim 14 wherein the nucleic acid binding factor is a transcription factor selected from the group consisting of p53, TrpR, cAMP receptor protein, and Lac repressor.

16. The method of claim 13 wherein the detection method is fluorescence polarization.

17. The method of claim 9 wherein the nucleic acid binding factor is attached to a solid matrix.

18. A biosensor assay useful for determining the activity of a nucleic acid binding factor comprising a first nucleic acid component and a second nucleic acid component, wherein
    (a) the first nucleic acid component comprises a portion of a nucleic acid binding element and the second nucleic acid component comprises a portion of the same nucleic acid binding element, wherein the combination of both the first and second nucleic acid components comprises the nucleic acid binding element; and
    (b) a detectable label is attached to the first nucleic acid component or the second nucleic acid component, wherein the label is detected by a proximity-based or coincidence-based luminescence signal detection method upon binding of the nucleic acid binding factor to the first and second nucleic acid components to form a nucleic acid binding element.

19. The biosensor assay of claim 18 wherein the first nucleic acid component is attached to a solid substrate and the second nucleic acid is attached to a detectable label.

20. The biosensor assay of claim 19 wherein
    (a) the solid substrate is a selected from the group consisting of multiwell plate, microarray slide, membrane, microsphere, light guide, optical fiber, conducting material, and surface of plasmon resonance chip, and (b) the detectable label is selected from the list consisting of a fluorochrome, chromophore, enzyme, linker molecule, biotin, electron donors, electron acceptors, dyes, metals, and radionuclide.

21. The biosensor assay of claim 20 wherein the solid substrate is a multiwell plate and the detectable label is biotin.

* * * * *